(12) United States Patent
Gajewski et al.

(10) Patent No.: US 11,638,728 B2
(45) Date of Patent: May 2, 2023

(54) MICROBIOME BIOMARKERS IMMUNOTHERAPY RESPONSIVENESS: DIAGNOSTIC, PROGNOSTIC AND THERAPEUTIC USES THEREOF

(71) Applicant: The University of Chicago, Chicago, IL (US)

(72) Inventors: Thomas F. Gajewski, Chicago, IL (US); Jason Luke, Oak Park, IL (US); Riyue Bao, Chicago, IL (US); Vyara Matson, Chicago, IL (US); Jessica Fessler, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/618,700

(22) PCT Filed: Jun. 5, 2018

(86) PCT No.: PCT/US2018/036052
§ 371 (c)(1),
(2) Date: Dec. 2, 2019

(87) PCT Pub. No.: WO2018/226690
PCT Pub. Date: Dec. 13, 2018

(65) Prior Publication Data
US 2021/0177918 A1 Jun. 17, 2021

Related U.S. Application Data

(60) Provisional application No. 62/515,366, filed on Jun. 5, 2017, provisional application No. 62/577,454, filed on Oct. 26, 2017.

(51) Int. Cl.
| | | |
|---|---|---|
| A61K 35/745 | (2015.01) | |
| A61P 35/00 | (2006.01) | |
| A61K 35/747 | (2015.01) | |
| C07K 16/28 | (2006.01) | |

(52) U.S. Cl.
CPC .......... *A61K 35/745* (2013.01); *A61K 35/747* (2013.01); *A61P 35/00* (2018.01); *C07K 16/2818* (2013.01); *C07K 16/2827* (2013.01)

(58) Field of Classification Search
CPC ...................................................... A61K 39/00
USPC ....... 424/9.2, 93.1, 93.3, 93.4, 234.1, 277.1, 424/278.1
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,260,203 A | 11/1993 | Ladner et al. |

| | | | |
|---|---|---|---|
| 8,449,878 B2 | 5/2013 | Yonak et al. | |
| 2016/0235792 A1 | 8/2016 | Berry et al. | |
| 2021/0346438 A1* | 11/2021 | Zitvogel | .............. A61K 35/744 |

FOREIGN PATENT DOCUMENTS

| | | |
|---|---|---|
| WO | WO 88/01649 | 3/1988 |
| WO | WO 2016/063263 | 4/2016 |
| WO | WO 2016/196605 | 12/2016 |

OTHER PUBLICATIONS

13. Ramakrishna, Balakrishnan, "The Normal Bacterial Flora of the Human Intestine and Its Regulation", Journal of Clinical Gastroenterology, vol. 41, suppl. 1, pp. S2-S6, 2007.*
"Checking In on Cancer Checkpoint Inhibitors" https://www.cancer.gov/news-events/cancer-currents-blog/2015/gulley-checkpoint Dec. 18, 2015 retrieved on Nov. 30, 2021.*
Extended European Search Report for PCT/US2018036052, dated Feb. 17, 2021. 10 pages.
International Search Report and Written Opinion for PCT/US18/36052, dated Aug. 30, 2018. 7 pages.
Andrews, FastQC: A quality control application for high throughput sequence data. Babraham Institute. Project page: http://www.bioinformatics.babraham.ac.uk/projects/fastqc, 2016. Retrieved May 11, 2022. 6 pages.
Atarashi et al., Induction of colonic regulatory T cells by indigenous *Clostridium* species. Science. Jan. 21, 2011;331(6015):337-41.
Benjamini et al., Controlling the False Discovery Rate: a Practical and Powerful Approach to Multiple Testing. J Roy Stat Soc B Met. 1995. 57, 289-300.
Blank et al., PD-L1/B7H-1 inhibits the effector phase of tumor rejection by T cell receptor (TCR) transgenic CD8+ T cells. Cancer Res. Feb. 1, 2004;64(3):1140-5.
Bray et al., Near-optimal probabilistic RNA-seq quantification. Nat Biotechnol. May 2016;34(5):525-7.
Buffie et al., Profound alterations of intestinal microbiota following a single dose of clindamycin results in sustained susceptibility to Clostridium difficile-induced colitis. Infect Immun. Jan. 2012;80(1):62-73.
Caporaso et al., Global patterns of 16S rRNA diversity at a depth of millions of sequences per sample. Proc Natl Acad Sci U S A. Mar. 15, 2011;108 Suppl 1 (Suppl 1):4516-22.
Caporaso et al., PyNAST: a flexible tool for aligning sequences to a template alignment. Bioinformatics. Jan. 15, 2010;26(2):266-7.
Caporaso et al., QIIME allows analysis of high-throughput community sequencing data. Nat Methods. May 2010;7(5):335-6.

(Continued)

*Primary Examiner* — Oluwatosin A Ogunbiyi
(74) *Attorney, Agent, or Firm* — Casimir Jones SC; David W. Staple

(57) ABSTRACT

Provided herein are compositions and methods comprising microbiome biomarkers of responsiveness/resistance to immunotherapy (e.g., anti-PD1/PD-L1 therapy), and diagnostic, prognostic and therapeutic uses thereof. In particular, the amount, identity, presence, and/or ratio of microflora in the microbiome of a subject is used to determine the responsiveness/resistance of the subject to immunotherapy, and/or the microbiome of a subject is manipulated to enhance the responsiveness of the subject to various immunotherapies and co-therapies.

14 Claims, 29 Drawing Sheets
(19 of 29 Drawing Sheet(s) Filed in Color)
Specification includes a Sequence Listing.

(56) References Cited

OTHER PUBLICATIONS

Caporaso et al., Ultra-high-throughput microbial community analysis on the Illumina HiSeq and MiSeq platforms. ISME J. Aug. 2012;6(8):1621-4.
Chothia et al., Canonical structures for the hypervariable regions of immunoglobulins. J Mol Biol. Aug. 20, 1987;196(4):901-17.
Chothia et al., Conformations of immunoglobulin hypervariable regions. Nature. Dec. 21-28, 1989;342(6252):877-83.
Cibulskis et al., Sensitive detection of somatic point mutations in impure and heterogeneous cancer samples. Nat Biotechnol. Mar. 2013;31 (3):213-9.
Clackson et al. Making antibody fragments using phage display libraries. Nature. Aug. 15, 1991;352(6336):624-8.
Collado et al., Intestinal integrity and Akkermansia muciniphila, a mucin-degrading member of the intestinal microbiota present in infants, adults, and the elderly. Appl Environ Microbiol. Dec. 2007;73(23):7767-70.
Daillere et al., Enterococcus hirae and Barnesiella intestinihominis Facilitate Cyclophosphamide-Induced Therapeutic Immunomodulatory Effects. Immunity. Oct. 18, 2016;45(4):931-943.
Fu et al., Analysis of 6,515 exomes reveals the recent origin of most human protein-coding variants. Nature. Jan. 10, 2013;493(7431):216-20.
Gajewski et al. Gene signature in melanoma associated with clinical activity: a potential clue to unlock cancer immunotherapy. Cancer J. Jul.-Aug. 2010;16(4):399-403.
Genomes Project Consortium et al., A global reference for human genetic variation. Nature. Oct. 1, 2015;526(7571):68-74.
Geva-Zatorsky et al., Mining the Human Gut Microbiota for Immunomodulatory Organisms. Cell. Feb. 23, 2017;168(5):928-943.e11.
Hamid et al., Safety and tumor responses with lambrolizumab (anti-PD-1) in melanoma. N Engl J Med. Jul. 11, 2013;369(2):134-44.
Harlow et al., Antibodies: A Laboratory Manual. Cold Spring Harbor Laboratory, Cold Spring Harbor, N.Y. 1988. TOC only. 9 pages.
Hodi et al., Improved survival with ipilimumab in patients with metastatic melanoma. N Engl J Med. Aug. 19, 2010;363(8):711-23.
Hudson et al., Engineered antibodies. Nat. Med. 2003. 9:129-134.
Huijsdens et al., Quantification of bacteria adherent to gastrointestinal mucosa by real-time PCR. J Clin Microbiol. Dec. 2002;40(12):4423-7.
Human Microbiome Project, A framework for human microbiome research. Nature. Jun. 13, 2012;486(7402):215-21.
Iida et al., Commensal bacteria control cancer response to therapy by modulating the tumor microenvironment. Science. Nov. 22, 2013;342(6161):967-70.
Ji et al., An immune-active tumor microenvironment favors clinical response to ipilimumab. Cancer Immunol Immunother. Jul. 2012;61(7):1019-31.
Junick et al., Quantification of human fecal *Bifidobacterium* species by use of quantitative real-time PCR analysis targeting the groEL gene. Appl Environ Microbiol. Apr. 2012;78(8):2613-22.
Kassinen et al., The fecal microbiota of irritable bowel syndrome patients differs significantly from that of healthy subjects. Gastroenterology. Jul. 2007;133(1):24-33.
Kohler et al., Continuous cultures of fused cells secreting antibody of predefined specificity. Nature. Aug. 7, 1975;256(5517):495-7.
Lek et al., Analysis of protein-coding genetic variation in 60,706 humans. Nature. Aug. 18, 2016;536(7616):285-91.
Li. Aligning sequence reads, clone sequences and assembly contigs with BWA-MEM. arXiv:1303.3997v2 [q-bio.GN], 2013. 3 pages.
Louis et al., Organization of butyrate synthetic genes in human colonic bacteria: phylogenetic conservation and horizontal gene transfer. FEMS Microbiol Lett. Apr. 2007;269(2):240-7.
Malinen et al., Comparison of real-time PCR with SYBR Green I or 5'-nuclease assays and dot-blot hybridization with rDNA-targeted oligonucleotide probes in quantification of selected faecal bacteria. Microbiology (Reading). Jan. 2003;149(Pt 1):269-77.
Marks et al., By-passing immunization. Human antibodies from V-gene libraries displayed on phage. J Mol Biol. Dec. 5, 1991;222(3):581-97.
Matsuda et al., Establishment of an analytical system for the human fecal microbiota, based on reverse transcription-quantitative PCR targeting of multicopy rRNA molecules. Appl Environ Microbiol. Apr. 2009;75(7):1961-9.
Matsuki et al., Rapid identification of human intestinal bifidobacteria by 16S rRNA-targeted species- and group-specific primers. FEMS Microbiol Lett. Oct. 15, 1998;167(2):113-21.
McDonald et al., An improved Greengenes taxonomy with explicit ranks for ecological and evolutionary analyses of bacteria and archaea. ISME J. Mar. 2012;6(3):610-8.
Pitt et al., Fine-Tuning Cancer Immunotherapy: Optimizing the Gut Microbiome. Cancer Res. Aug. 15, 2016;76(16):4602-7.
Rathnayake et al., Genotyping of Enterococcus faecalis and Enterococcus faecium isolates by use of a set of eight single nucleotide polymorphisms. J Clin Microbiol. Jan. 2011;49(1):367-72.
Rinttila et al., Development of an extensive set of 16S rDNA-targeted primers for quantification of pathogenic and indigenous bacteria in faecal samples by real-time PCR. J Appl Microbiol. 2004;97(6):1166-77.
Robert et al., Pembrolizumab versus Ipilimumab in Advanced Melanoma. N Engl J Med. Jun. 25, 2015;372(26):2521-32.
Round et al., Inducible Foxp3+ regulatory T-cell development by a commensal bacterium of the intestinal microbiota. Proc Natl Acad Sci U S A. Jul. 6, 2010;107(27):12204-9.
Segata et al., Metagenomic microbial community profiling using unique clade-specific marker genes. Nat Methods. Jun. 10, 2012;9(8):811-4.
Sivan et al., Commensal Bifidobacterium promotes antitumor immunity and facilitates anti-PD-L1 efficacy. Science. Nov. 27, 2015;350(6264):1084-9.
Soneson et al., Differential analyses for RNA-seq: transcript-level estimates improve gene-level inferences. F1000Res. Dec. 30, 2015;4:1521.
Song et al., Cohabiting family members share microbiota with one another and with their dogs. Elife. Apr. 16, 2013;2:e00458. 22 pages.
Spranger et al., Up-regulation of PD-L1, IDO, and T(regs) in the melanoma tumor microenvironment is driven by CD8(+) T cells. Sci Transl Med. Aug. 28, 2013;5(200):200ra116. 21 pages.
Sun et al., Locked nucleic acid pentamers as universal PCR primers for genomic DNA amplification. PLoS One. 2008;3(11):e3701. 7 pages.
Tarasov et al., Sambamba: fast processing of NGS alignment formats. Bioinformatics. Jun. 15, 2015;31(12):2032-4.
Taur et al., The effects of intestinal tract bacterial diversity on mortality following allogeneic hematopoietic stem cell transplantation. Blood. Aug. 14, 2014;124(7):1174-82.
Tong et al., Application of quantitative real-time PCR for rapid identification of Bacteroides fragilis group and related organisms in human wound samples. Anaerobe. Apr. 2011;17(2):64-8.
Topalian et al., Safety, activity, and immune correlates of anti-PD-1 antibody in cancer. N Engl J Med. Jun. 28, 2012;366(26):2443-54.
Topalian et al., Survival, durable tumor remission, and long-term safety in patients with advanced melanoma receiving nivolumab. J Clin Oncol. Apr. 1, 2014;32(10):1020-30.
Tumeh et al., PD-1 blockade induces responses by inhibiting adaptive immune resistance. Nature. 2014. 515(7528):568-571.
Van Der Auwera et al., From FastQ data to high confidence variant calls: the Genome Analysis Toolkit best practices pipeline. Curr Protoc Bioinformatics. 2013;43(1110):11.10.1-11.10.33. 43 pages.
Vetizou et al., Anticancer immunotherapy by CTLA-4 blockade relies on the gut microbiota., Science, vol. 350, No. 6264. 2015. pp. 1079-1084.
Wang et al., ANNOVAR: functional annotation of genetic variants from high-throughput sequencing data. Nucleic Acids Res. Sep. 2010;38(16):e164. 7 pages.
Wang et al., Naive Bayesian classifier for rapid assignment of rRNA sequences into the new bacterial taxonomy. Appl Environ Microbiol. Aug. 2007;73(16):5261-7.

(56) References Cited

OTHER PUBLICATIONS

Wolchok et al., Nivolumab plus ipilimumab in advanced melanoma. N Engl J Med. Jul. 11, 2013;369(2):122-33.

Yampara-Iquise et al., Use of a Bacteroides thetaiotaomicron-specific alpha-1-6, mannanase quantitative PCR to detect human faecal pollution in water. J Appl Microbiol. Nov. 2008;105(5):1686-93.

* cited by examiner

FIG. 4B
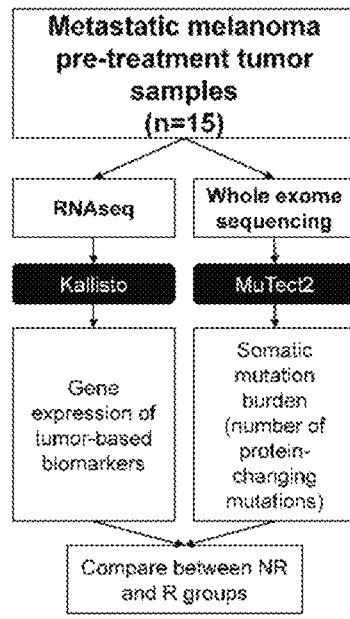
Human tumor sequencing
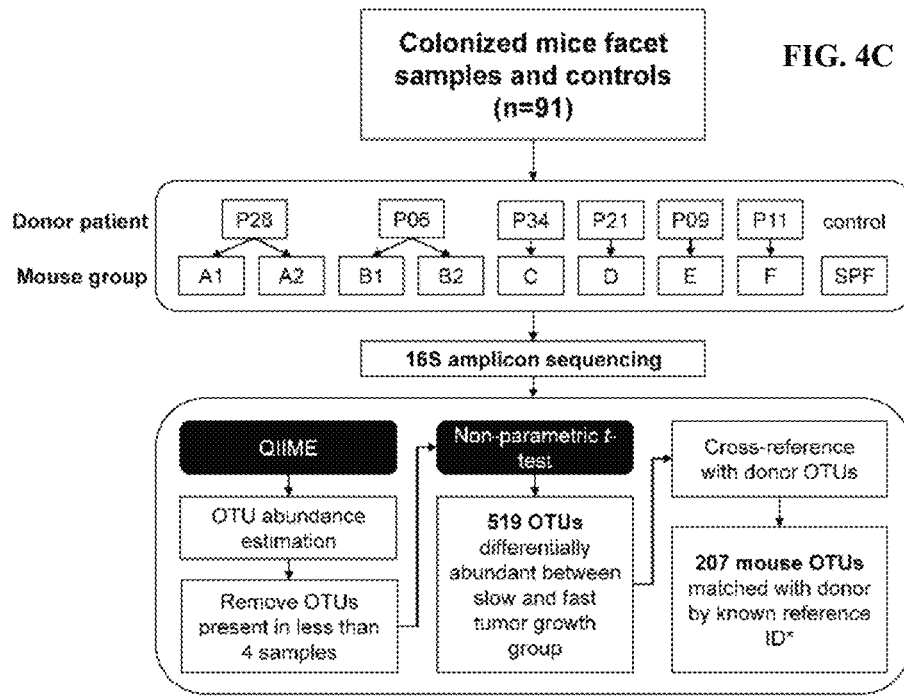
Mouse microbiota sequencing
FIG. 4C

A

*Ruminococcus obeum* (qPCR)

*Roseburia intestinalis* (qPCR)

B.

B.

SEQUENCE LISTING

<160> NUMBER OF SEQ ID NOS: 34

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
cagcacgtga aggtggggac                                                     20

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
ccttgcggtt ggcttcagat                                                     20

<210> SEQ ID NO 3
<211> LENGTH: 23
<212> TYPE: DNA
<213> ORGANISM: Artificial sequence
<220> FEATURE:
<223> OTHER INFORMATION: Synthetic

<400> SEQUENCE: 3
aagggagcgt agatggatgt tta                                                 23

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
cgagcctcaa tgtcagttgc                                                     20

<210> SEQ ID NO 5
<211> LENGTH: 31
<212> TYPE: DNA
<213> ORGANISM: Artificial sequence
<220> FEATURE:
<223> OTHER INFORMATION: Synthetic

<400> SEQUENCE: 5
cctgcctcaa ctgcactcaa gatatccagt a                                        31

<210> SEQ ID NO 6
<211> LENGTH: 23
<212> TYPE: DNA
<213> ORGANISM: Artificial sequence
<220> FEATURE:
<223> OTHER INFORMATION: Synthetic

<400> SEQUENCE: 6
ctccgccgct gatccggaag tcg                                                 23

<210> SEQ ID NO 7
<211> LENGTH: 25
<212> TYPE: DNA
<213> ORGANISM: Artificial sequence
<220> FEATURE:
<223> OTHER INFORMATION: Synthetic

<400> SEQUENCE: 7
aaccaactcg gcgatgtgga cgaca          25

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
ttccagttga tcgcatggtc                20

<210> SEQ ID NO 9
<211> LENGTH: 18
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is g or c

<400> SEQUENCE: 9
tcncgcttgc tccccgat                  18

<210> SEQ ID NO 10
<211> LENGTH: 16
<212> TYPE: DNA
<213> ORGANISM: Artificial sequence
<220> FEATURE:
<223> OTHER INFORMATION: Synthetic

<400> SEQUENCE: 10
cccgacggga ggggat                    16

<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
cttctgcagg tacagtcttg a              21

<210> SEQ ID NO 12
<211> LENGTH: 26
<212> TYPE: DNA
<213> ORGANISM: Artificial sequence
<220> FEATURE:
<223> OTHER INFORMATION: Synthetic

<400> SEQUENCE: 12
cgagaagagc tgcaaaatgc tttagc         26

<210> SEQ ID NO 13
<211> LENGTH: 19
<212> TYPE: DNA
<213> ORGANISM: Artificial sequence
<220> FEATURE:
<223> OTHER INFORMATION: Synthetic

```
<400> SEQUENCE: 13
gcgcgcttca attccttgt                                                19

<210> SEQ ID NO 14
<211> LENGTH: 17
<212> TYPE: DNA
<213> ORGANISM: Artificial sequence
<220> FEATURE:
<223> OTHER INFORMATION: Synthetic

<400> SEQUENCE: 14
cccttcagtg ccgcagt                                                  17

<210> SEQ ID NO 15
<211> LENGTH: 18
<212> TYPE: DNA
<213> ORGANISM: Artificial sequence
<220> FEATURE:
<223> OTHER INFORMATION: Synthetic

<400> SEQUENCE: 15
gtcgcaggat gtcaagac                                                 18

<210> SEQ ID NO 16
<211> LENGTH: 24
<212> TYPE: DNA
<213> ORGANISM: Artificial sequence
<220> FEATURE:
<223> OTHER INFORMATION: Synthetic

<400> SEQUENCE: 16
gcgtggcggt agatctaagt cata                                          24

<210> SEQ ID NO 17
<211> LENGTH: 21
<212> TYPE: DNA
<213> ORGANISM: Artificial sequence
<220> FEATURE:
<223> OTHER INFORMATION: Synthetic

<400> SEQUENCE: 17
ttcagctccg ccacaaaggt a                                             21

<210> SEQ ID NO 18
<211> LENGTH: 21
<212> TYPE: DNA
<213> ORGANISM: Artificial sequence
<220> FEATURE:
<223> OTHER INFORMATION: Synthetic

<400> SEQUENCE: 18
caccgaatgc ttgcaytcac c                                             21

<210> SEQ ID NO 19
<211> LENGTH: 19
<212> TYPE: DNA
<213> ORGANISM: Artificial sequence
<220> FEATURE:
<223> OTHER INFORMATION: Synthetic

<400> SEQUENCE: 19
gccgcgggtc catccaaaa                                                19

<210> SEQ ID NO 20
<211> LENGTH: 21
```

```
<212> TYPE: DNA
<213> ORGANISM: Artificial sequence
<220> FEATURE:
<223> OTHER INFORMATION: Synthetic

<400> SEQUENCE: 20
tgcctatcag aggggggataa c                                              21

<210> SEQ ID NO 21
<211> LENGTH: 21
<212> TYPE: DNA
<213> ORGANISM: Artificial sequence
<220> FEATURE:
<223> OTHER INFORMATION: Synthetic

<400> SEQUENCE: 21
gcaaatattc ccatgcggga t                                               21

<210> SEQ ID NO 22
<211> LENGTH: 28
<212> TYPE: DNA
<213> ORGANISM: Artificial sequence
<220> FEATURE:
<223> OTHER INFORMATION: Synthetic

<400> SEQUENCE: 22
cgaaagtcgg actaataccg catgaagc                                        28

<210> SEQ ID NO 23
<211> LENGTH: 19
<212> TYPE: DNA
<213> ORGANISM: Artificial sequence
<220> FEATURE:
<223> OTHER INFORMATION: Synthetic

<400> SEQUENCE: 23
agggtgcgta ggtggtgat                                                  19

<210> SEQ ID NO 24
<211> LENGTH: 18
<212> TYPE: DNA
<213> ORGANISM: Artificial sequence
<220> FEATURE:
<223> OTHER INFORMATION: Synthetic

<400> SEQUENCE: 24
ttcaccgcta caccacgc                                                   18

<210> SEQ ID NO 25
<211> LENGTH: 27
<212> TYPE: DNA
<213> ORGANISM: Artificial sequence
<220> FEATURE:
<223> OTHER INFORMATION: Synthetic

<400> SEQUENCE: 25
ttacttgagt gtgtttgagg taggcgg                                         27

<210> SEQ ID NO 26
<211> LENGTH: 20
<212> TYPE: DNA
<213> ORGANISM: Artificial sequence
<220> FEATURE:
<223> OTHER INFORMATION: Synthetic
```

```
<400> SEQUENCE: 26
ttcgcagctc agtctatcgc                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
gcaatccccg ggaagtcatt                                              20

<210> SEQ ID NO 28
<211> LENGTH: 18
<212> TYPE: DNA
<213> ORGANISM: Artificial sequence
<220> FEATURE:
<223> OTHER INFORMATION: Synthetic

<400> SEQUENCE: 28
gcagatttgg tctgtttc                                                18

<210> SEQ ID NO 29
<211> LENGTH: 19
<212> TYPE: DNA
<213> ORGANISM: Artificial sequence
<220> FEATURE:
<223> OTHER INFORMATION: Synthetic

<400> SEQUENCE: 29
cggtattagc aaccatttc                                               19

<210> SEQ ID NO 30
<211> LENGTH: 24
<212> TYPE: DNA
<213> ORGANISM: Artificial sequence
<220> FEATURE:
<223> OTHER INFORMATION: Synthetic

<400> SEQUENCE: 30
ctgtataagg caggttaccc acgc                                         24

<210> SEQ ID NO 31
<211> LENGTH: 18
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is c or t

<400> SEQUENCE: 31
ancaacctgc ccttcaga                                                18

<210> SEQ ID NO 32
<211> LENGTH: 20
<212> TYPE: DNA
<213> ORGANISM: Artificial sequence
<220> FEATURE:
<223> OTHER INFORMATION: Synthetic
```

```
<400> SEQUENCE: 32
cgtcccgatt aacagagctt                                              20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
agagtttgat cctggctcag                                              20

<210> SEQ ID NO 34
<211> LENGTH: 18
<212> TYPE: DNA
<213> ORGANISM: Artificial sequence
<220> FEATURE:
<223> OTHER INFORMATION: Synthetic

<400> SEQUENCE: 34
tgctgcctcc cgtaggag                                                18
```

MICROBIOME BIOMARKERS IMMUNOTHERAPY RESPONSIVENESS: DIAGNOSTIC, PROGNOSTIC AND THERAPEUTIC USES THEREOF

CROSS-REFERENCE TO RELATED APPLICATION

The present application is a § 371 U.S. National Entry Application of PCT/US2018/036052, filed Jun. 5, 2018, which claims priority to U.S. Provisional Patent Application Ser. No. 62/515,366 filed Jun. 5, 2017, and U.S. Provisional Patent Application Ser. No. 62/577,454, filed Oct. 26, 2017, each of which is herein incorporated by reference in its entirety.

STATEMENT OF GOVERNMENT SUPPORT

This invention was made with government support under Grant Number CA210098 awarded by the National Institutes of Health. The government has certain rights in the invention.

SEQUENCE LISTING

The text of the computer readable sequence listing filed herewith, titled "35305-253_Sequence_Listing_ST25", created Dec. 2, 2019, having a file size of 7,000 bytes, is hereby incorporated by reference in its entirety.

FIELD

Provided herein are compositions and methods comprising microbiome biomarkers of responsiveness/resistance to immunotherapy (e.g., anti-PD1/PD-L1 therapy), and diagnostic, prognostic and therapeutic uses thereof. In particular, the amount, identity, presence, and/or ratio of microflora in the microbiome of a subject is used to determine the responsiveness/resistance of the subject to immunotherapy, and/or the microbiome of a subject is manipulated to enhance the responsiveness of the subject to various immunotherapies and co-therapies.

BACKGROUND

The responsiveness of patients to cancer immunotherapies, such as anti-CTLA-4 and anti-PD-1/PD-L1 antibodies (Hodi et al. The New England Journal of Medicine 363, 711-723 (2010); Hamid et al. The New England Journal of Medicine 369, 134-144 (2013); incorporated by reference in their entireties), is enhanced in patients who show evidence of an endogenous T cell response ongoing in the tumor microenvironment at baseline (Tumeh et al. Nature 515, 568-571 (2014); Spranger et al. Science Translational Medicine 5, 200ra116 (2013); Ji et al. Cancer Immunology, Immunotherapy: CII 61, 1019-1031 (2012); Gajewski et al. Cancer Journal 16, 399-403 (2010); herein incorporated by reference in their entireties). What is needed are biomarkers for characterizing a patient's responsiveness/resistance to immunotherapy and treatments for inducing T cell inflammation in the tumor microenvironment.

SUMMARY

Provided herein are compositions and methods comprising microbiome biomarkers of responsiveness/resistance to immunotherapy (e.g., anti-PD1/PD-L1 therapy), and diagnostic, prognostic and therapeutic uses thereof. In particular, the amount, identity, presence, and/or ratio of microflora in the microbiome of a subject is used to determine the responsiveness/resistance of the subject to immunotherapy, and/or the microbiome of a subject is manipulated to enhance the responsiveness of the subject to various immunotherapies and co-therapies.

In some embodiments, provided herein are methods of treating or preventing cancer in a subject, comprising modulating levels of one or more commensal microbes within the subject to: (A) enhance an immune response by the subject, (B) inhibit the growth or spread of the cancer, (C) inhibit immune evasion by the cancer, and/or (D) enhance the efficacy of a therapeutic. In some embodiments, the levels of one or more commensal microbes are modulated within the gut of the subject. In some embodiments, modulating the levels of one or more commensal microbes comprises increasing and/or decreasing levels of bacteria strains, species, and/or families described herein. In some embodiments, the level is modulated of bacteria strains from one or more families selected from the group consisting of Coriobacteriaceae, Ruminococcaceae, Lachnospiraceae, Clostridiaceae, Bifidobacteriacae, Enterobacteriacae, and Erysipelotrichaceae. In some embodiments, the bacterial strains or species are selected from the OTU 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, OTU 325850, OTU 352933, 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae. In some embodiments, levels are modulated of a bacteria with variable importance score of 25 or greater (e.g., 25, 30, 35, 40, 45, 50, 55, 60, 65, 70, 75, 80, 85, 90, 95, or greater, or ranges therebetween (e.g., 60 or greater). In some embodiments, levels are modulated of a bacteria identified on Table 6. In some embodiments, levels are modulated of a bacteria of the species *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*.

In some embodiments, modulating the levels of one or more commensal microbes comprises administering a beneficial microbes to the subject. In some embodiments, the beneficial microbes are bacteria. In some embodiments, the bacteria are selected from the families Coriobacteriaceae, Ruminococcaceae, Lachnospiraceae, Clostridiaceae, Bifidobacteriacae, Enterobacteriacae, and Erysipelotrichaceae. In some embodiments, the bacteria are selected from the species *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*. In some embodiments, the beneficial microbes are administered as a probiotic composition or via microflora transplant from a donor.

In some embodiments, modulating the levels of one or more commensal microbes comprises administering one or more antimicrobials. In some embodiments, the antimicrobial kills detrimental microbes. In some embodiments, the antimicrobial is an antibiotic. In some embodiments, methods further comprise administration of beneficial microbes to the subject (e.g., following antibiotic administration).

In some embodiments, methods herein comprise administering to a subject a bacterial formulation comprising bacteria described herein. In some embodiments, methods further comprise administering to the subject a cancer therapy. In some embodiments, modulating levels of one or more commensal microbes within the subject (e.g., by administering a bacterial formulation, by administering an antibiotic, etc.) enhances an immune response by the subject and/or inhibits immune evasion by the cancer, and the cancer therapy is an immunotherapy. In some embodiments, the immunotherapy comprises administration of anti-CTLA-4 antibodies and/or anti-PD-L1 or anti-PD-1 antibodies. In some embodiments, modulating levels of one or more commensal microbes within the subject enhances the efficacy of a therapeutic, and the cancer therapy is said therapeutic. In some embodiments, the therapeutic comprises a chemotherapeutic. In some embodiments, methods further comprise testing the subject for immune evasion by the cancer. In some embodiments, methods further comprise surgical, radiation, and/or chemotherapeutic cancer intervention.

In some embodiments, provided herein are kits or compositions comprising a beneficial commensal microbe and a cancer therapeutic, said compositions or components of said kits formulated for therapeutic delivery to a subject.

In some embodiments, provided herein are beneficial commensal microbes for use as a medicament in the treatment of cancer, inhibition of immune evasion, and/or enhance immune response.

In some embodiments, provided herein are methods of treating or preventing cancer in a subject comprising administering to the subject a bacterial formulation comprising bacteria of the families Coriobacteriaceae, Ruminococcaceae, Lachnospiraceae, Clostridiaceae, Bifidobacteriacae, Enterobacteriacae, and/or Erysipelotrichaceae. In some embodiments, provided herein are methods of treating or preventing cancer in a subject comprising administering to the subject a bacterial formulation comprising bacteria selected from the species *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum*. In some embodiments, at least 50% of the bacteria in the bacterial formulation are of the families Coriobacteriaceae, Ruminococcaceae, Lachnospiraceae, Clostridiaceae, Bifidobacteriacae, Enterobacteriacae, and/or Erysipelotrichaceae. In some embodiments, at least 90% of the bacteria in the bacterial formulation are of the genera families Coriobacteriaceae, Ruminococcaceae, Lachnospiraceae, Clostridiaceae, Bifidobacteriacae, Enterobacteriacae, and/or Erysipelotrichaceae. In some embodiments, at least 50% of the bacteria in the bacterial formulation are selected from the species *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum*. In some embodiments, at least 90% of the bacteria in the bacterial formulation are selected from the species *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum*. In some embodiments, the bacteria are selected from the group consisting of OTU 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, 325850, OTU 352933, OTU 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae.

In some embodiments, the bacteria are selected from the group consisting of *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum*.

In some embodiments, provided herein are methods of treating cancer in a human subject comprising administering to the subject an immune checkpoint inhibitor and a bacterial formulation comprising bacteria of the species *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum*.

In some embodiments, provided herein are methods of characterizing the degree of responsiveness/non-responsiveness of a tumor within a subject to immunotherapy treatment, comprising determining the presence, absence, or level of one or more bacteria, wherein increased levels of bacteria of the species *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum* in a subject are indicative of tumor responsiveness to immunotherapy treatment, and wherein increased levels of bacteria of the species *Ruminococcus obeum* and/or *Roseburia intestinalis* in a subject are indicative of tumor non-responsiveness to immunotherapy treatment.

In some embodiments, provided herein are methods of treating a subject with cancer by administering an immunotherapy to a subject with increased levels of *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum* bacteria.

In some embodiments, provided herein are methods of treating a subject with cancer by administering an immunotherapy and a bacterial formulation comprising one or more of *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum* bacteria, wherein prior to treatment the subject has increased levels of *Ruminococcus obeum* and/or *Roseburia intestinalis* bacteria and/or decreased levels of *Enterococcus faecium*, *Collinsella aerofaciens*, *Bifidobacterium adolescentis*, *Klebsiella pneumoniae*, *Veillonella parvula*, *Parabacteroides merdae*, *Lactobacillus* sp. and/or *Bifidobacterium longum* bacteria.

In some embodiments, provided herein are methods of treating a subject by administering an immunotherapy wherein the subject has a ratio of beneficial:nonbenefical microbes greater than 1.0. In some embodiments, the ratio is equal to or greater than 1.5.

In some embodiments, the cancer is selected from the group consisting of acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, telangiectaltic sarcoma, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

In some embodiments, the subject is human. In some embodiments, the bacterial formulation is administered by oral administration, rectal administration, topical administration, inhalation or injection. In some embodiments, the bacterial formulation is a food product. In some embodiments, the bacterial formulation comprises at least about $5 \times 10^6$ CFU of bacteria. In some embodiments, the bacterial formulation is administered to the subject in two or more doses. In some embodiments, the administration of at least two of the two or more doses are separated by at least 1 day. In some embodiments, the administration of at least two of the two or more doses are separated by at least 1 week.

In some embodiments, methods further comprise administering to the subject an antibiotic. In some embodiments, the antibiotic is administered to the subject before the bacterial formulation. In some embodiments, the antibiotic is administered to the subject at least 1 day before the bacterial formulation is administered to the subject.

In some embodiments, methods further comprise administering to the subject an immune checkpoint inhibitor. In some embodiments, the immune checkpoint inhibitor is a protein or polypeptide that specifically binds to an immune checkpoint protein. In some embodiments, the immune checkpoint protein is selected from the group consisting of CTLA4, PD-1, PD-L1, PD-L2, A2AR, B7-H3, B7-H4, BTLA, KIR, LAG3, TIM-3 or VISTA. In some embodiments, the polypeptide or protein is an antibody or antigen-binding fragment thereof. In some embodiments, the immune checkpoint inhibitor is an interfering nucleic acid molecule. In some embodiments, the interfering nucleic acid molecule is a siRNA molecule, a shRNA molecule or an antisense RNA molecule. In some embodiments, the immune checkpoint inhibitor is selected from the group consisting of nivolumab, pembrolizumab, pidilizumab, AMP-224, AMP-514, STI-A1110, TSR-042, RG-7446, BMS-936559, BMS-936558, MK-3475, CT 011, MPDL3280A, MEDI-4736, MSB-0020718C, AUR-012 and STI-A1010. In some embodiments, the immune checkpoint inhibitor is administered before the bacterial formulation. In some embodiments, the immune checkpoint inhibitor is administered at least one day before the bacterial formulation. In some embodiments, the immune checkpoint is administered at about the same time as the bacterial formulation. In some embodiments, the immune checkpoint inhibitor is administered on the same day as the bacterial formulation. In some embodiments, the immune checkpoint inhibitor is administered after the bacterial formulation. In some embodiments, the immune checkpoint inhibitor is administered at least one day after the bacterial formulation. In some embodiments, the immune checkpoint inhibitor is administered by injection. In some embodiments, the injection is an intravenous, intramuscular, intratumoral or subcutaneous injection.

In some embodiments, provided herein are methods of treating cancer in a human subject comprising administering to the subject an immune checkpoint inhibitor and a bacterial formulation comprising bacteria of the families Coriobacteriaceae, Ruminococcaceae, Lachnospiraceae, Clostridiaceae, Bifidobacteriacae, Enterobacteriacae, and/or Erysipelotrichaceae. In some embodiments, the bacteria are selected from the OTU group consisting of 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, OTU 325850, OTU 352933, 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae. In some embodiments, at least 50% (e.g., 50%, 55%, 60%, 65%, 70%, 75%, 80%, 85%, 90%, 95%, 99%, or more, or ranges therebetween) of the bacteria in the bacterial formulation are of the families Coriobacteriaceae, Ruminococcaceae, Lachnospiraceae, Clostridiaceae, Bifidobacteriacae, Enterobacteriacae, and/or Erysipelotrichaceae. In some embodiments, at least 90% (e.g., 90%, 95%, 99%, 99.9%, 99.99%, or more or ranges therebetween) of the bacteria in the bacterial formulation are of the families Coriobacteriaceae, Ruminococcaceae, Lachnospiraceae, Clostridiaceae, Bifidobacteriacae, Enterobacteriacae, and/or Erysipelotrichaceae. In some embodiments, the bacteria of the families Coriobacteriaceae, Ruminococcaceae, Lachnospiraceae, Clostridiaceae, Bifidobacteriacae, Enterobacteriacae, and/or Erysipelotrichaceae comprise bacteria of the strains or species from the OTU 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, OTU 325850, OTU 352933, 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae.

In some embodiments, provided herein are methods of treating cancer in a human subject comprising administering to the subject an immune checkpoint inhibitor and a bacterial formulation comprising bacteria of the species *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*. In some embodiments, at least 50% (e.g., 50%, 55%, 60%, 65%, 70%, 75%, 80%, 85%, 90%, 95%, 99%, or more, or ranges therebetween) of the bacteria in the bacterial formulation are of the species *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*. In some embodiments, at least 90% (e.g., 90%, 95%, 99%, 99.9%, 99.99%, or more or ranges therebetween) of the bacteria in the bacterial formulation are of the species *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*.

In some embodiments, the bacterial formulation is administered by oral administration or rectal administration. In some embodiments, the bacterial formulation is administered by oral administration. In some embodiments, the bacterial formulation comprises at least $5 \times 10^6$ CFU (e.g., $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 10^{12}$ CFU, $2 \times 10^{12}$ CFU, $5 \times 10^{12}$ CFU, or more or ranges therebetween) of bacteria of the species described herein In some embodiments, the bacterial formulation is administered to the subject in two or more doses (e.g., 2, 3, 4, 5, 6, 7, 8, 9, 10, or more, or ranges therebetween). In some embodiments, the administration of doses are separated by at least 1 week. In some embodiments, methods further comprise administering to the subject an antibiotic prior to the administration of the bacterial formulation. In some embodiments, the antibiotic is administered to the subject at least 1 day before the bacterial formulation is administered to the subject. In some embodiments, the immune checkpoint inhibitor is a protein or polypeptide that binds to an immune checkpoint protein. In some embodiments, the immune checkpoint inhibitor is an antibody or antigen binding fragment thereof that binds to an immune checkpoint protein. In some embodiments, the immune checkpoint protein is CTLA4, PD-1, PD-L1, PD-L2, A2AR, B7-H3, B7-H4, BTLA, KIR, LAG3, TIM-3 or VISTA. In some embodiments, the immune checkpoint protein is PD-1 or PD-L1. In some embodiments, the immune checkpoint inhibitor is nivolumab, pembrolizumab, pidilizumab, AMP-224, AMP-514, STI-A1110, TSR-042, RG-7446, BMS-936559, BMS-936558, MK-3475, CT 011, MPDL3280A, MEDI-4736, MSB-0020718C, AUR-012 and STI-A1010. In some embodiments, the immune checkpoint inhibitor is administered by intravenous injection, intramuscular injection, intratumoral injection or subcutaneous injection.

In some embodiments, provided herein are methods of treating cancer in a human subject comprising administering to the subject a bacterial formulation comprising at least $5 \times 10^6$ CFU (e.g., $5 \times 10^6$ CFU, $1 \times 10^7$ CFU, $2 \times 10^7$ CFU, $5 \times 10^7$ CFU, $1 \times 10^8$ CFU, $2 \times 10^8$ CFU, $5 \times 10^8$ CFU, $1 \times 10^9$ CFU, $2 \times 10^9$ CFU, $5 \times 10^9$ CFU, $1 \times 10^{10}$ CFU, $2 \times 10^{10}$ CFU, $5 \times 10^{10}$ CFU, $1 \times 10^{11}$ CFU, $2 \times 10^{11}$ CFU, $5 \times 10^{11}$ CFU, $1 \times 10^{12}$ CFU, $2 \times 10^{12}$ CFU, $5 \times 10^{12}$ CFU, or more or ranges therebetween) of bacteria of there species described herein. In some embodiments, at least 90% (e.g., 90%, 95%, 99%, 99.9%, 99.99%, or more or ranges therebetween) of the bacteria in the bacterial formulation are of the species described herein. In some embodiments, the bacterial formulation is administered by oral administration or rectal administration. In some embodiments, the bacterial formulation is administered by oral administration. In some embodiments, the bacterial formulation is administered to the subject in two or more doses (e.g., 2, 3, 4, 5, 6, 7, 8, 9, 10, or more, or ranges therebetween). In some embodiments, methods further comprise administering to the subject an antibiotic before the bacterial formulation is administered to the subject. In some embodiments, methods further comprise administering to the subject an immune checkpoint inhibitor. In some embodiments, the immune checkpoint inhibitor is an antibody or antigen binding fragment thereof that binds to CTLA4, PD-1, PD-L1, PD-L2, A2AR, B7-H3, B7-H4, BTLA, KIR, LAG3, TIM-3 or VISTA. In some embodiments, the immune checkpoint inhibitor is an antibody or antigen binding fragment thereof that binds to PD-1 or PD-L1. In some embodiments, the immune checkpoint inhibitor is nivolumab, pembrolizumab, pidilizumab, AMP-224, AMP-514, STI-A1110, TSR-042, RG-7446, BMS-936559, BMS-936558, MK-3475, CT 011, MPDL3280A, MEDI-4736, MSB-0020718C, AUR-012 and STI-A1010.

In some embodiments, provided herein are methods of characterizing the degree of responsiveness/non-responsiveness of a tumor within a subject to immunotherapy treatment, comprising determining the presence, absence, or level of one or more bacteria described herein. In some embodiments, bacteria are of the families Coriobacteriaceae, Ruminococcaceae, Lachnospiraceae, Clostridiaceae, Bifidobacteriacae, Enterobacteriacae, and/or Erysipelotrichaceae, wherein the bacteria in a subject are indicative of tumor responsiveness or non-responsiveness to immunotherapy treatment. In some embodiments, bacteria of the species *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*. In some embodiments, the bacteria are selected from the bacteria listed in Table 6. In some embodiments, the bacteria comprise strains or species selected from the group consisting of 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, OTU 325850, OTU 352933, 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae. In some embodiments, methods provide a diagnosis (e.g., T-cell inflamed tumor, non-T-cell-inflammed tumor, etc), prognosis (e.g., tumor will respond (or likely to respond) to immunotherapy, tumor will not respond (or unlikely to respond) to immunotherapy), or treatment course of action (e.g., proceed with immunotherapy, proceed with co-therapy or immunotherapy and beneficial bacteria, proceed by manipulating microbiome to achieve responsive tumor microenvironment, etc). In some embodiments, such methods find use with other embodiments (e.g., cancers, treatments, etc.) described herein.

In some embodiments, provided herein are methods of predicting a clinical response of a subject to a cancer treatment comprising: (a) characterizing the make-up of the gut microflora of the subject, wherein characterizing the make-up of the gut microflora comprising determining the amounts of various beneficial bacterial and non-beneficial bacteria in the gut of the subject; (b) determining whether the subject is a likely responder of likely non-responder to the cancer treatment based on the relative amounts of the beneficial and non-beneficial bacteria in the gut of the subject. In some embodiments, methods comprise calculating a ratio of beneficial bacterial to non-beneficial bacteria in the gut of the subject. In some embodiments, metgods comprise determining that the subject is a likely responder if the ratio of beneficial bacterial to non-beneficial bacteria is above a threshold value. In some embodiments, the threshold value is 1.0 or greater (e.g., 1.0, 1.1, 1.2, 1.3, 1.4, 1.5, 1.6, 1.7, 1.8, 1.9, 2.0, 2.5, 3.0, 3.5, 4.0, 5.0, or greater, or ranges therebetween (e.g., 1.5 or greater)). In some embodiments, the cancer treatment is an immunotherapy. In some embodiments, provided herein are methods of treating a subject with cancer by comprising: (a) predicting a clinical response of a subject to a cancer treatment by the methods herein; and (b) if the subject is determined to be a likely responder to the cancer treatment, administering the cancer treatment of the subject.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4A-C. Workflow schematic indicating (A) the integration of methods for microbial identification, (B) analyses of tumor-associated biomarkers, and (C) 16S rRNA sequencing-based identification of human fecally-derived bacteria with a potential role in modulating anti-tumor immunity in a mouse melanoma model.

DEFINITIONS

Figure 1A:
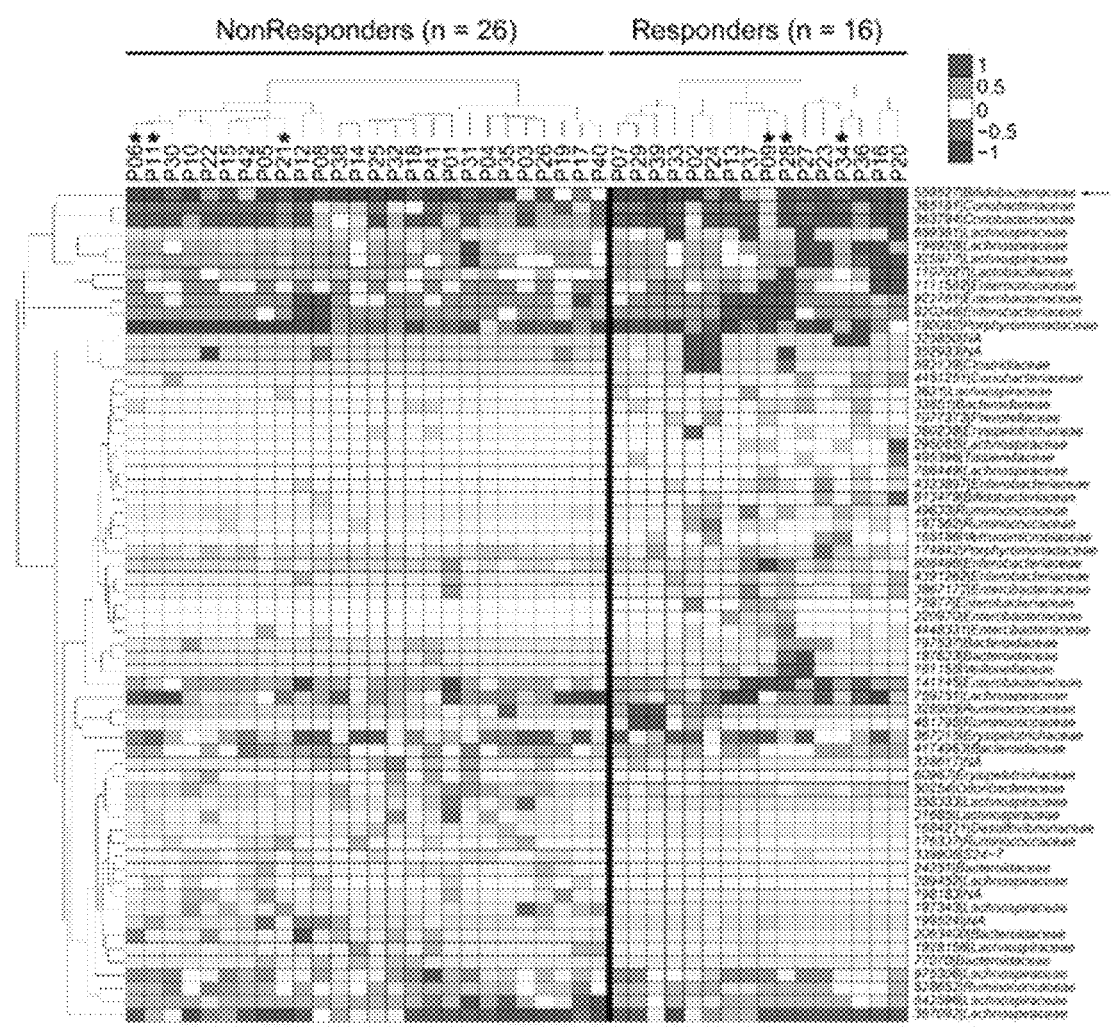
FIG. 1A-B. Distinct commensal microbial communities in anti-PD-1 responders and non-responders as assessed by 16S rRNA sequencing. (A) Relative abundance of differentially abundant taxa in responders vs. non-responders; 62 OTUs were identified as different with P<0.05 (unadjusted, non-parametric t test). An additional OTU 559527 (arrow) identified as Bifidobacteriaceae approached significance (P<0.058). Supervised hierarchical clustering of the different taxa was performed based on clinical outcome. Individual samples are organized in columns, labeled with patient identification number. Asterisks indicate samples used in further in-vivo experiments. (B) Principal component analysis of relative abundance of the 63 OTUs shown in FIG. 1A.

The terminology used herein is for the purpose of describing the particular embodiments only, and is not intended to limit the scope of the embodiments described herein. Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a microbiome biomarker" is a reference to one or more microbiome biomarkers of resistance to immunotherapy and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "microbe" refers to cellular microorganisms including bacteria, fungi, and archaea, and encompasses both individual organisms and populations comprising any number of the organisms.

As used herein, the term "tumor microenvironment" refers to the tissues, cells, molecules, and blood vessels that surround and feed a tumor cell. A tumor's microenvironment is dynamic and a tumor can change its microenvironment, and the microenvironment can affect how a tumor grows and spread.

As used herein, the terms "microbiota" and "microflora" refer to an assemblage of microorganisms localized to a distinct environment. Microflora may include, for example, populations of various bacteria, fungi, and/or archaea that inhabit a particular environment. For example, "gut microflora," "vaginal microbiota," and "oral microflora" are an assemblage of one or more species of microorganisms that are localized to, or found in, the gut, vagina, or mouth, respectively. "Normal microflora" refers to a population of microorganisms that localize in a particular environment in a normal, non-pathological state (e.g., a sample of gut microflora from a subject without cancer). "Pathologic microflora" refers to a population of various microorganisms that localize in a particular environment in pathological state and differs from normal microflora in terms of identify, absolute amount, or relative amount of the various microbes.

As used herein, the term "commensal microbe" refers to a microorganism that is non-pathogenic to a host and is part of the normal microflora of the host.

As used herein, the term "co-administration" refers to the administration of at least two agents (e.g., commensal microflora and a cancer therapy) or therapies to a subject. In some embodiments, the co-administration of two or more agents/therapies is concurrent. In other embodiments, the co-administration of two or more agents/therapies is sequential (e.g., a first agent/therapy is administered prior to a second agent/therapy).

As used herein, the term "beneficial microbe" refers to a microbe (e.g., bacterium) strain or species that inhibits the growth of cancer/tumor cells and/or facilitates treatment of cancer/tumor cells (e.g., inhibits immune evasion). Beneficial microbes may function by, for example, creating an anti-cancer/anti-tumor environment, microenvironment and/or metabolome, and/or by creating an environment, microenvironment and/or metabolome that inhibits immune evasion or other mechanisms by which cancer cells resist therapy.

As used herein, the term "detrimental microbe" refers to a microbe (e.g., bacterium) strain or species that facilitates the growth of cancer/tumor cells and/or prevents or reduces the effectiveness of treatment of cancer/tumor cells. Detrimental microbes may function by, for example, creating an environment, microenvironment and/or metabolome that facilitates immune evasion or other mechanisms by which cancer cells resist therapy and/or enhance cancer/tumor growth.

As used herein, the term "pharmaceutical agent" refers to a compound, macromolecule, or other chemical/non-biological entity that is administered to a subject to elicit a desired biological response. A pharmaceutical agent may be a "drug" or another entity which is biologically active in a human being or other mammal, locally and/or systemically. Examples of drugs are disclosed in the Merck Index and the Physicians Desk Reference, the entire disclosures of which are incorporated by reference herein for all purposes.

As used herein, the terms "microbial agent," "commensal microbial agent," and "probiotic" refer to compositions comprising a microbe or population of multiple different microbes for administration to a subject.

As used herein, the term "antimicrobial agent" is used to describe a therapeutic compound or bioactive agent which treats a microbial infection, for example, an infection caused by a bacteria, virus, protozoa or fungus. The antimicrobial agent may be an antibiotic, an antifungal agent, an antiviral or an antiprotozoal or antiparasitic agent (which may also be used to treat multicellular parasites).

As used herein, the terms "antibiotic" and "antibacterial agent" refer to a chemical agent which is active against bacteria. In common usage, an antibiotic is a substance or compound that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymixins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

As used herein, the term "antiviral agent" refers to a chemical agent which is used to treat a viral infection. Antiviral drugs are a class of medication used specifically for treating viral infections, specific antivirals are useful for treating infection by specific viruses. Antivirals typically only inhibit virus development.

As used herein, the term "antifungal agent" refers to a therapeutic compound or bioactive agent which may be used to treat a fungal infection in a patient. An antifungal drug is a medication used to treat fungal infections such as athlete's foot, ringworm, candidiasis (thrush), serious systemic infections such as cryptococcal meningitis, and related fungal infections. Antifungal agents include, for example, polyene antifungals, imidazole, triazole and thiazole antifungals, allylamines, echinocandins, griseofulvin, flycystosine, undecylenic acid, among others.

As used herein, the term "antiparasitic agent" refers to a therapeutic compound or bioactive agent that is used to treat parasitic diseases including nematodes, cestodes, trematodes, infectious protozoa, and amoebas. Exemplary antiparasitic agents include: antinematodes (e.g., mebendazole, pyrantel pamoate, thiabendazole, diethycarbazine), anticestodes (e.g., niclosamide, praziquantel), antitrematodes (e.g., praziquantel), antiamoebics (e.g., rifampin and amphotericin B), antiprotozoals (e.g., melarsoprol, eflornithine, metronidazole and tinidazole), among others.

As used herein, the term "pharmaceutical formulation" refers to at least one pharmaceutical agent and/or microbial agent in combination with one or more additional components that assist in rendering the agent(s) suitable for achieving the desired effect upon administration to a subject. The pharmaceutical formulation may include one or more additives, for example pharmaceutically acceptable excipients, carriers, penetration enhancers, coatings, stabilizers, buffers or other materials physically associated with the pharmaceutical/microbial agent to enhance the administration, release (e.g., timing of release), deliverability, bioavailability, effectiveness, etc. of the dosage form. The formulation may be, for example, a liquid, a suspension, a solid, a nanoparticle, emulsion, micelle, ointment, gel, emulsion, coating, etc. A pharmaceutical formulation may contain a single agent or multiple agents (e.g., microbial agent and pharmaceutical agent).

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition (e.g., cancer, solid tumor cancer, non-T cell-infiltrated tumor cancer, etc.).

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including Abs, cytokines, and complement) that results in selective targeting, binding to, damage to, destruction of, and/or elimination from a subject of invading pathogens, cells or tissues infected with pathogens, or cancerous or other abnormal cells.

As used herein, the term "immunoregulator" refers to an agent or a signaling pathway (or a component thereof) that regulates an immune response. "Regulating," "modifying" or "modulating" an immune response refers to any alteration of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in a cancer microenvironment.

As used herein, the term "immune evasion" refers to inhibition of a subject's immune system or a component thereof (e.g., endogenous T cell response) by a cancer or tumor cell in order to maximize or allow continued growth or spread of the cancer/tumor.

As used herein, the term "immunotherapy" refers to the treatment or prevention of a disease or condition (e.g., cancer) by a method comprising inducing, enhancing, suppressing or otherwise modifying an immune response.

As used herein, "potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "antibody" refers to a whole antibody molecule or a fragment thereof (e.g., fragments such as Fab, Fab', and F(ab')2), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VH, and three constant regions, CH1, CH2, and CH3. The VH domain is at the amino-terminus of the heavy chain, and the CH3 domain is at the carboxy-terminus. In a native antibody, a light chain comprises a variable region, VL, and a constant region, CL. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant (Ka) of at least $10^7$ M$^{-1}$ (e.g., $>10^7$ M$^{-1}$, $>10^8$ M$^{-1}$, $>10^9$ M$^{-1}$, $>10^{10}$ M$^{-1}$, $>10^{11}$ M$^{-1}$, $>10^{12}$ M$^{-1}$, $>10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')2, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the CH1 and variable region of one heavy chain. The heavy chain of a Fab molecule cannot form a disulfide bond with another heavy chain molecule. A "Fab'" fragment comprises one light chain and one heavy chain that comprises additional constant region, extending between the CH1 and CH2 domains. An interchain disulfide bond can be formed between two heavy chains of a Fab' fragment to form a "F(ab')2" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "effective dose" or "effective amount" refers to an amount of an agent, e.g., an antibody, that results in the reduction of symptoms in a patient or results in a desired biological outcome. In certain embodiments, an effective dose or effective amount is sufficient to treat or reduce symptoms of a disease or condition.

DETAILED DESCRIPTION

Provided herein are compositions and methods comprising microbiome biomarkers of responsiveness/resistance to immunotherapy (e.g., anti-PD1/PD-L1 therapy), and diagnostic, prognostic and therapeutic uses thereof. In particular, the amount, identity, presence, and/or ratio of microflora in the microbiome of a subject is used to determine the responsiveness/resistance of the subject to immunotherapy, and/or the microbiome of a subject is manipulated to enhance the responsiveness of the subject to various immunotherapies and co-therapies.

In some embodiments, the effectiveness of an endogenous immune response, immunotherapy, chemotherapeutic, or other treatment (e.g., surgery, radiation, etc.) in the treatment or prevention of reoccurrence of cancer and/or tumor is dependent upon conditions within the subject (e.g., the tumor microenvironment). In particular, the identity or characteristics (e.g., concentration or level) of the microflora within a subject affects the effectiveness of cancer treatments (e.g., generally or specific treatments) and/or the effectiveness of the subject's own immune response to cancer.

In some embodiments, the presence or increased level of one or more microbes (e.g., one or more types of bacteria) in a subject potentiates cancer/tumor growth, spread (e.g., malignancy), and/or evasion of treatment/immune response. In some embodiments, the presence or increased level of one or more microbes (e.g., one or more types of bacteria) in a subject inhibits treatment (e.g., immunotherapy, chemotherapy, etc.) and/or the subject's endogenous immune response to cancer and/or tumor cells. In some embodiments, the absence and/or decreased level of one or more microbes (e.g., one or more types of bacteria) in a subject potentiates cancer/tumor growth, spread, and/or evasion of treatment/immune response. In some embodiments, the absence or decreased level of one or more microbes (e.g., one or more types of bacteria) in a subject inhibits treatment (e.g., immunotherapy, chemotherapy, etc.) and/or the subject's endogenous immune response to cancer and/or tumor cells.

In some embodiments, the presence or increased level of one or more microbes (e.g., one or more types of bacteria) in a subject discourages cancer/tumor growth, spread, and/or evasion of treatment/immune response. In some embodiments, the presence or increased level of one or more microbes (e.g., one or more types of bacteria) in a subject facilitates treatment (e.g., immunotherapy, chemotherapy, etc.) and/or the subject's endogenous immune response to cancer and/or tumor cells. In some embodiments, the absence and/or decreased level of one or more microbes (e.g., one or more types of bacteria) in a subject discourages cancer/tumor growth, spread, and/or evasion of treatment/immune response. In some embodiments, the absence or decreased level of one or more microbes (e.g., one or more types of bacteria) in a subject facilitates treatment (e.g., immunotherapy, chemotherapy, etc.) and/or the subject's endogenous immune response to cancer and/or tumor cells.

In some embodiments, the presence of beneficial microbes (e.g., microbes that facilitate cancer treatment) in a subject creates an environment or microenvironment (e.g., metabolome) that is conducive to the treatment of cancer and/or inhibits cancer/tumor growth. In some embodiments, the presence of detrimental microbes (e.g., microbes that facilitate cancer/tumor growth and/or prevent treatment) in a subject creates an environment or microenvironment (e.g., metabolome) that is conducive to the treatment of cancer and/or inhibits cancer/tumor growth.

Experiments conducted during development of embodiments described herein demonstrate that the responsiveness/resistance of a tumor to immunotherapies can be assessed by assaying the bacteria present in the microbiome of a subject. Particular microbes identified in experiments herein (e.g., bacteria of Table 6, bacteria of the families Coriobacteriaceae, Ruminococcaceae, Lachnospiraceae, Clostridiaceae, Bifidobacteriacae, Enterobacteriacae, and/or Erysipelotrichacea, bacteria are selected from the OTU group consisting of 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, OTU 325850, OTU 352933, 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae; etc.) correlate, are indicative of, contribute to, and/or are causivite of responsiveness or resistance of tumors to immunotherapies. Characterization of the identity of microbes with a subject finds use in determining the likelihood that a tumor within the subject will respond to particular immunotherapies. In some embodiments, treatment course of action (e.g., immunotherapy, chemotherapy, microbial therapy, combinations thereof, etc.) is determined based on the methods herein.

Experiments conducted during development of embodiments described herein demonstrate that modulation of levels and/or identity of the microflora in a subject facilitates treatment of cancer/tumor within the subject, enhances the endogenous immune response, decreases immune evasion or other inhibitory mechanisms to treatment of endogenous immune response, and/or improves cancer outcomes for the subject. Modulation of microflora levels and/or identity may comprise encouraging or facilitating growth of one or more types of beneficial microbes (e.g., microbes that facilitate cancer treatment), discouraging or inhibiting growth of one or more types of detrimental microbes (e.g., microbes that facilitate cancer/tumor growth and/or prevent treatment), administering one or more types of beneficial microbes (e.g., microbes that facilitate cancer treatment) to the subject, and/or combinations thereof. Embodiments within the scope herein are not limited by the mechanisms for introducing one or more microbes (e.g., fecal transplant, probiotic administration, etc.), encouraging growth of beneficial microbes (e.g., administering agents that skew the environment within the subject toward growth conditions for the beneficial microbes), discouraging or inhibiting growth of detrimental microbes (e.g., administering agents that skew the environment within the subject away from growth conditions for the detrimental microbes, administration of antimicrobial(s), etc.), and combinations thereof.

In some embodiments, methods are provided for the treatment or prevention of cancer by the manipulation of the presence, amount, or relative ratio of commensal microflora (e.g., gut microflora). In some embodiments, the presence, amount, or relative ratio of particular bacteria, fungi, and/or archaea within a subject is manipulated. In some embodiments, the levels of one or more bacterial list in Table 6 are manipulated. For example, in some embodiments, the presence, amount, or relative ratio of one or more bacteria from the familes Coriobacteriaceae, Ruminococcaceae, Lachnospiraceae, Clostridiaceae, Bifidobacteriacae, Enterobacteriacae, and/or Erysipelotrichaceae are manipulated. In some embodiments, the presence, amount, or relative ratio of one or more of 365181 Coriobacteriaceae, 197562 Ruminococcaceae, 363794 Coriobacteriaceae, 295085 Lachnospiraceae, 659361 Lachnospiraceae, 461795 Ruminococcaceae, 592139 Clostridiaceae, 813479 Bifidobacteriacae, OTU 325850, OTU 352933, 559527 Bifidobacteriacae, 808486 Enterobacteriacae, 830346 Enterobacteriacae, 198928 Lachnospiraceae, 367215 Erysipelotrichaceae, 1973443 Lachnospiraceae, and 367092 Lachnospiraceae are manipulated.

In some embodiments, the presence and/or levels of one or more commensal microbes are manipulated in a subject suffering from cancer, at heightened risk of cancer, and/or receiving treatment for cancer. Exemplary commensal microbes include *Lactococcus* (e.g., *Lactococcus cremoris* and *Lactococcus lactis*), *Lactobacillus* (e.g., *Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbrueckii, Lactobacillus plantarum, Lactobacillus paraplantarum, Lactobacillus crispatus, Lactobacillus gasseri, Lactobacillus johnsonii* and *Lactobacillus jensenii*), *Leuconostoc, Carnobacterium, Enterococcus, Propionibacteium, Pediococcus, Bifidobacterium* (e.g., *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis, Bifidobacteriumangulatum*, etc.), *Streptococcus* (e.g., *Streptococcus thermophiles, Streptococcus salivarius, Streptococcus oralis, Streptococcus uberis, Streptococcus rattus*, etc.); *Escherichia coli, Bacillus coagulans, Bacillus lansii*, Yeast (e.g., *Saccharomyces cerevisiae, Saccharomyces boulardii*, etc.); and combinations thereof.

In experiments conducted during development of embodiments herein, baseline stool samples were analyzed from metastatic melanoma patients prior to immunotherapy treatment, through an integration of 16S rRNA sequencing, metagenomic shotgun sequencing, and quantitative PCR for selected bacteria. A significant association between commensal microbial composition and clinical response was observed. Bacterial species more abundant in responders included *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum*. Bacterial species more abundant in non-responders included *Ruminococcus obeum* and *Roseburia intestinalis*. The experiments indicate that reconstitution of germ-free subjects with fecal material from responding patients provides improved tumor control, augmented T cell responses, and/or greater efficacy of immunotherapy (e.g., anti-PD-L1 therapy). The experimental results demonstrate a mechanistic impact of the commensal microbiota on anti-tumor immunity in cancer.

In some embodiments, the presence and/or levels of one or more commensal microbes are manipulated in a subject suffering from cancer, at heightened risk of cancer, and/or receiving treatment for cancer.

In some embodiments, one or more species, genera, and/or types of microbes are administered and/or the growth thereof is facilitated. In some embodiments, the growth of one or more species, genera, and/or types of microbes is inhibited. In some embodiments, one or more species, genera, and/or types of microbes are administered and/or the growth thereof is facilitated; and the growth of one or more other species, genera, and/or types of microbes is inhibited.

In some embodiments, the level or presence of one or more beneficial microbes (e.g., microbes that inhibit cancer/ tumor growth or spread, enhance cancer/tumor treatment, etc.) is modulated by the administration of such microbes to a subject.

In some embodiments, microflora-modulation utilizes prepared probiotic compositions for administration to/by a subject. Probiotic compositions comprise one or more beneficial microbes (e.g., bacteria) formulated such that administration of the probiotic (e.g., orally, rectally, by inhalation, etc.) results in population of the subject by the beneficial microbes.

In some embodiments, probiotic compositions comprise cultured microbes that are combined and/or formulated for administration to a subject. In some embodiments, probiotics contain microbes of known genera, species, etc. and/or at known concentrations (cfus). Probiotic compositions may be in the form of a pharmaceutical-type composition (e.g., capsule, tables, liquid, aerosol, etc.) or in the form of a food supplement.

In some embodiments, probiotic microbes (e.g., bacteria) are formulated in a pharmaceutically acceptable composition for delivery to a subject. In some embodiments, probiotics are formulated with a pharmaceutically acceptable carrier suitable for a solid or semi-solid formulation. In some embodiments, probiotic microbes are formulated with a pharmaceutically acceptable carrier suitable for a liquid or gel formulation. Probiotic formulations may be formulated for enteral delivery, e.g., oral delivery, or delivery as a suppository, but can also be formulated for parenteral delivery, e.g., vaginal delivery, inhalational delivery (e.g., oral delivery, nasal delivery, and intrapulmonary delivery), and the like.

The probiotic compositions that find use in embodiments described herein may be formulated in a wide variety of oral administration dosage forms, with one or more pharmaceutically acceptable carriers. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the probiotic microbes. In tablets, the microbes are mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Other forms suitable for oral administration include liquid form preparations such as emulsions, syrups, elixirs, aqueous solutions, aqueous suspensions, or solid form preparations which are intended to be converted shortly before use to liquid form preparations. Aqueous suspensions can be prepared by dispersing the probiotic microbes in water with viscous material, such as natural or synthetic gums, resins, methylcellulose, sodium carboxymethylcellulose, and other well-known suspending agents.

The probiotic compositions (e.g., microbes (e.g., bacteria)) may be formulated for administration as suppositories. A low melting wax, such as a mixture of fatty acid glycerides or cocoa butter is first melted and the probiotic microbes are dispersed homogeneously, for example, by stirring. The molten homogeneous mixture is then poured into conveniently sized molds, allowed to cool, and to solidify.

The probiotic compositions (e.g., microbes (e.g., bacteria)) may be formulated for vaginal administration. Pessaries, tampons, creams, gels, pastes, foams or sprays, may contain agents in addition to the bacteria, such carriers, known in the art to be appropriate.

In some embodiments, probiotic compositions (e.g., microbes (e.g., bacteria)) may be formulated for delivery by inhalation. As used herein, the term "aerosol" is used in its conventional sense as referring to very fine liquid or solid particles carries by a propellant gas under pressure to a site of therapeutic application. The term "liquid formulation for delivery to respiratory tissue" and the like, as used herein, describe compositions comprising probiotic microbes with a pharmaceutically acceptable carrier in flowable liquid form. Such formulations, when used for delivery to a respiratory tissue, are generally solutions, e.g. aqueous solutions, ethanolic solutions, aqueous/ethanolic solutions, saline solutions and colloidal suspensions.

Rather than pharmaceutical-type formulation, probiotic compositions may be formulated as food additive and/or food product and incorporated into a variety of foods and beverages. Suitable foods and beverages include, but are not limited to, yogurts, ice creams, cheeses, baked products such as bread, biscuits and cakes, dairy and dairy substitute foods, soy-based food products, grain-based food products, starch-based food products, confectionery products, edible oil compositions, spreads, breakfast cereals, infant formulas, juices, power drinks, and the like.

In some embodiments, a probiotic composition is administered over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of the probiotic composition administered for the dosing time period is concentration of from about 10 to about $1 \times 10^{14}$ colony forming units (cfu) of the commensal microbial agent(s) (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.).

In some embodiments, the microbial make-up of a probiotic composition consists or consists essentially of one or more beneficial microbes (e.g., bacteria). In some embodiments, the microbial make-up of a probiotic composition consists or consists essentially of 1, 2, 3, 4, 5, 6, 7, 8, 9, 10, 15, 20, 25, 30, 40, 50, 60, 70, 80, 90, 100, or any ranges therein (e.g., 1-4, 5-10, 8-20, etc.) strains and/or species of microbes. In some embodiments, fewer than 50 microbial strains (e.g., 1, 2, 3, 4, 5, 6, 7, 8, 9, 10, 15, 20, 25, 30, 40, 50, or any ranges therein (e.g., 1-4, 5-10, 8-20, etc.) are at least 50% (e.g., 50%, 60%, 70%, 80%, 85%, 90%, 91%, 92%, 93%, 94%, 95%, 96%, 97%, 98%, 99%, 99.5%. 99.9%, 99.99%) of the microbial population (e.g., by mass, by cfu, etc.) of a probiotic composition. For example, in some embodiments, a single species or strain of bacteria selected from the families Coriobacteriaceae, Ruminococcaceae, Lachnospiraceae, Clostridiaceae, Bifidobacteriacae, Enterobacteriacae, and Erysipelotrichaceae, and/or from the species *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum*, is at least 95% of the microbial population, as measured by colony forming units, of a particular probiotic composition. As another example, in some embodiments, a single species or strain of bacteria selected from the families Coriobacteriaceae, Ruminococcaceae, Lachnospiraceae, Clostridiaceae, Bifidobacteriacae, Enterobacteriacae, and Erysipelotrichaceae, and/or from the species *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum* is at least 40% of the microbial population (e.g., 40%, 50%, 60%, 70%, 80%, 90%, or more, or ranges therebetween), as measured by mass, of a particular probiotic composition. These examples are not limiting.

In some embodiments, microflora in a subject (e.g., a subject suffering from cancer, a subject with microflora that promotes cancer growth, a subject with microflora that promotes evasion of cancer treatment (e.g., by immunotherapy), etc.) are modulated by transplantation of microbiota from a subject with favorable characteristics (e.g., a subject without cancer, a subject with microflora that inhibits cancer growth, a subject with microflora that promotes treatment of cancer (e.g., by immunotherapy), etc.) into the recipient subject.

In some embodiments, donor microflora are obtained sampling microflora from the desired region of the donor subject body (e.g., colon, oral cavity, vagina, etc.). In particular embodiments, fecal material (e.g., 100 g-500 g) is obtained from a donor. The material may be administered to a recipient subject with or without subsequent preparation steps (e.g., diluting, mixing, oxygenating, filtering, supplementing (e.g., with prebiotics, with growth media, etc.), testing (e.g., for pathogens or detrimental microbes), etc.). The donor microflora (e.g., fecal material) may be administered without preservation (e.g., administered within 12 hours (e.g., <6 hours, <4 hours, <2 hours, <1 hour, etc.)) or may be preserved (e.g., frozen, freeze dried, etc.), for example, to allow for delay (e.g., 1 day, 2, days, 1 week, 1 month, or more) before delivery to the subject.

In some embodiments, donor microflora are processed to remove one or more components. For example, parasitic of detrimental microbes may be removed or killed. Contaminants within the donor sample may be removed. In some embodiments, donor microflora is enriched for one or more specific microbes (e.g., 2-fold, 3-fold, 4 fold, 10-fold, 20-fold, or more enrichment). In some embodiments, donor microflora is enriched such that at least 1% of the microbes in the population are the desired beneficial microbes (e.g., 1%, 2%, 3%, 4%, 5%, 6%, 7%, 8%, 9%, 10%, 15%, 20%, 25%, 30%, 40%, 50%, 60%, 70%, 80%, 90%, or more). In some embodiments, donor microflora are doped with one or more cultured beneficial microbes.

In particular embodiments, transplanted microflora may be administered to the recipient subject by any suitable delivery mechanism, including but not limited to enema, colonoscope, nasogastric or nasoduodenal tube, lavage or irrigation, or orally (e.g., in the form of a capsule).

In some embodiments, a commensal microbial agent or population of microbial agents is administered (e.g., via probiotic composition or microflora transplant) over a dosing time period (e.g., <1 minute, <1 hour, <2 hours, <4 hours, <6 hours, <12 hours, <24 hours, etc.) in an amount that is sufficient to provide a desired therapeutic benefit (e.g., as a single dose, in combination with other doses, in combination with a co-administered therapeutic, etc.) In some embodiments, the dose of commensal microbial agent(s) administered for the dosing time period is concentration of from about 10 to about $1 \times 10^{14}$ colony forming units (cfu) of the commensal microbial agent(s) (e.g., 10 cfu, 100 cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, $10^{13}$ cfu, or any suitable ranges therein (e.g., from about $10^2$ cfu to about $10^{13}$ cfu, about $1 \times 10^4$ to about $1 \times 10^{11}$ cfu, about $1 \times 10^6$ to about $1 \times 10^9$ cfu, about $1 \times 10^{10}$ to about $1 \times 10^{12}$ cf, etc.), etc.).

The dose can be administered in a single unit dose administered at any time during a day. Alternatively the loading dose can be administered in two or more doses administered at a single time of day or at two or more separate times of day.

Over the course of multiple dosing periods, the dose can be tapered from an initial dose to a higher dose (or increased from an initial dose to a higher dose), on predetermined timing or by the when the subject and/or clinician based on the results of the treatment. The appropriate dosage amount will vary by, for example, an individual subject's age, weight, condition or disease, severity of disease, etc.

In some embodiments, microbes for probiotic compositions are obtained from culture. In some embodiments, strains of beneficial microbes are genetically engineered to enhance one or more of production (e.g., at scale), formulation, delivery, or the biological effect of the microbe. In some embodiments, microbes are engineered to express a detectable marker that allows tracking of the microbes within a subject, or confirmation that the microbe has integrated into a subject's microflora. In some embodiments, microbes are engineered to express a cancer therapeutic (e.g., chemotherapeutic, immunotherapeutic, antibodies, etc.), anti-inflammatory agent, of other drug.

In some embodiments, one or more prebiotics are administered to a subject as an independent treatment (e.g., to increase the level of a beneficial microbe) or in conjunction with other treatments described herein. Prebiotics are agents that increase the in vivo growth rate or activity of commensal microbes. In some embodiments, prebiotics are soluble fiber sources. In some embodiments, when prebiotics are administered (e.g., fed) to a subject they are not digested or are not fully digested by the subject's digestive enzymes, but rather support the intestinal health of the subject and provide an energy source for the beneficial microbes and enhance the growth thereof. Prebiotics include, for example, naturally occurring lecithins and/or oleic acid, and are described, for example in U.S. Pat. No. 8,449,878 which is herein incorporated by reference in its entirety.

In some embodiments, the level or presence of one or more detrimental microbes (e.g., microbes that facilitate cancer/tumor growth or spread, inhibit cancer/tumor treatment, etc.) is modulated, for example, by the administration of one or more antimicrobial agents to a subject or modulation of conditions within the subject to disfavor growth of the detrimental microbes. In some embodiments, antimicrobial agents are administered.

In some embodiments, the antimicrobial agent is an antibiotic. Exemplary antibiotics that may find use in some embodiments include, but are not limited to: amikacin, gentamicin, kanamycin, neomycin, netilmicin, streptomycin, tobramycin, paromycin, geldanamycin, herbimycin, loracarbef, ertapenem, doripenem, imipenem, meropenem, cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobirprole, vancomycin, azithromycin, clarithromycin, dirithromycin, erythromycin, roxithromycin, troleandomycin, telithromycin, spectinomycin, aztreonam, amoxicillin, ampicillin, azociling, carbenicillin, cloxacillin, dicloxacillin, flucloxacillin, mezlocillin, meticillin, nafcillin, oxacillin, peperacillin, ticarcillin, bacitracin, colistin, polymyxin B, ciprofloxacin, clavulanic acid, enoxacin, gatifloxacin, levofloxacin, lomefloxacin, moxifloxacin, nonfloxacin, ofloxacin, trovafloxacin, grepafloxacin, sparfloxacin, AL-15469A, AL-38905, OP-145, afenide, prontosil, sulfacetamide, sulfamethiazole, sulfanamide, sulfasalazine, sulfisoxazole, trimethoprim, cotrimoxazole, demeclocycline, doxycycline, minocycline, oxytetracycline, tetraycline, linezolid, arsogebanubem chloramphenicol, clindamycin, lincomycin, ethambutol, fosfomycin, fusidic acid, furazolidone, isoniazid, linezolid, metronidazole, mupirocin, nitrofurantoin, rifampicin, thamphenicol, tinidazole, amoxicillin+clavulanic acid, Maximin H5, Dermcidin, Cecropins, andropin, moricin, ceratotoxin, melittin, Magainin, dermaseptin, bombinin, brevinin-1,esculentins and buforin II, CAP 18, LL37, abaecin, apidaecins, prophenin, indolicidin, brevinins, protegrin, tachyplesins, defensins, drosomycin, alamethicin, pexiganan or MSI-78, MSI-843, MSI-594, polyphemusin, colicin, pyocin, klebicin, subtilin, epidermin, herbicolacin, brevicin, halocin, agrocin, alveicin, carnocin, curvaticin, divercin, enterocin, enterolysin, erwiniocin, glycinecin, lactococin, lacticin, leucoccin, mesentericin, pediocin, plantaricin, sakacin, sulfolobicin, vibriocin, warnerinand, nisin, or a salt or cocrystal, or prodrug or solvate thereof, or a combination thereof.

In some embodiments, the antimicrobial is an antifungal agent. Exemplary antifungals that may find use in some embodiments include, but are not limited to: amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

In some embodiments, the antimicrobial is an antiparasitic. Exemplary antiparasitics that may find use in some embodiments include, but are not limited to: amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, methods and compositions for reduction of detrimental microbe levels are co-administered (e.g., serially, concurrently, etc.) with methods and compositions for increasing beneficial microbe levels. In some embodiments, by reducing overall microbe levels or by reducing the levels of specific microbes (e.g., detrimental microbes, high population microbes, etc.), the population of beneficial microbes can more effectively be modulated (e.g., increased).

In some embodiments, in order to develop a microflora population within a subject that facilitates cancer treatment or inhibits cancer growth/spread, antimicrobial agents are first administered to eliminate or reduce the microflora within the subject, and then the microflora population is reestablished using the methods and compositions described herein (e.g., administration of beneficial microbes). In some embodiments, antimicrobials (e.g., antibiotics) that reduce the microbe (e.g., bacteria) population generally are employed. In some embodiments, antimicrobials that target detrimental microbes preferentially are employed.

In some embodiments, modulating the microflora composition is sufficient on its own to allow the endogenous immune system of a subject to respond to the presence of cancer cells and or tumor growth. However, in other embodiments, microflora composition is manipulated along with one or more other cancer therapies. In some embodiments, manipulation of the microflora composition (e.g., identity and/or level) treats cancer by a mechanism independent of one or more additional cancer treatments. In other embodiments, modulation of microflora composition facilitates (e.g., increases the effectiveness of) the cancer treatment. In some embodiments, one or more cancer treatments enhance the effectiveness of the modulation of microflora composition. Embodiments herein are not limited by the types of cancer treatments (e.g., surgery, radiation, immunotherapy, chemotherapeutic, etc.) unless specifically noted.

In some embodiments, immunotherapeutic cancer treatment encompasses blockade of immune-inhibitory receptors, for example using monoclonal antibodies (mAbs) against CTLA-4 and PD-1/PD-L1 (Wolchok, J. D. et al. The New England Journal of Medicine 369, 122-133 (2013); Topalian, S. L. et al. Journal of Clinical Oncology 32, 1020-1030 (2014); Topalian, S. L. et al. The New England Journal of Medicine 366, 2443-2454 (2012); Hodi, F. S. et al. The New England Journal of Medicine 363, 711-723 (2010); herein incorporated by reference in their entireties).

In some embodiments, the immunotherapy includes the administration of an immune checkpoint inhibitor. Immune checkpoint inhibition broadly refers to inhibiting the checkpoint markers that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3, IDO or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, BMS-936558, MK-3475, CT 011, MPDL3280A, MEDI-4736, MSB-0020718C, AUR-012 and STI-A1010. In some embodiments, the immune checkpoint inhibitor may be administered via injection (e.g., intravenously, intratumorally, subcutaneously, or into lymph nodes), but may also be administered orally, topically, or via aerosol.

In some embodiments, the compositions for and/or methods of modulating microflora in a subject overcome immune invasion of cancer cells, tumor, tumor microenvironment, etc. In some embodiments, one or more additional cancer immunotherapies are employed (e.g., concurrently or serially) to make use of the induced immune-responsiveness treated cells/tumor. Suitable immunotherapies may include, but are not limited to: cell-based therapies (e.g., dendritic cell or T cell therapy, etc.), monoclonal antibody (mAb) therapy (e.g., naked mAbs, conjugated mAbs), cytokine therapy (e.g., interferons, interleukins, etc.), adjuvant treatment (e.g., polysaccharide-K, CpG oligonucleotides), etc.

Examples of antibodies that may find use in the compositions and methods disclosed herein, particularly for use in immunotherapies include, but are not limited, to antibodies such as trastuzumab (anti-HER2/neu antibody); pertuzumab (anti-HER2 mAb); cetuximab (chimeric monoclonal antibody to epidermal growth factor receptor EGFR); panitumumab (anti-EGFR antibody); nimotuzumab (anti-EGFR antibody); zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); rituximab (chimeric murine/human anti-CD20 mAb); obinutuzumab (anti-CD20 mAb); ofatumumab (anti-CD20 mAb); tositumumab-1131 (anti-CD20 mAb); ibritumomab tiuxetan (anti-CD20 mAb); bevacizumab (anti-VEGF mAb); ramucirumab (anti-VEGFR2 mAb); ranibizumab (anti-VEGF mAb); aflibercept (extracellular domains of VEGFR1 and VEGFR2 fused to IgG1 Fc); AMG386 (angiopoietin-1 and -2 binding peptide fused to IgG1 Fc); dalotuzumab (anti-IGF-1R mAb); gemtuzumab ozogamicin (anti-CD33 mAb); alemtuzumab (anti-Campath-1/CD52 mAb); brentuximab vedotin (anti-CD30 mAb): catumaxomab (bispecific mAb that targets epithelial cell adhesion molecule and CD3); naptumomab (anti-5T4 mAb); girentuximab (anti-Carbonic anhydrase ix); or farletuzumab (anti-folate receptor). Other examples include antibodies such as Panorex™ (17-1A) (edrecolomab, murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym); Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); Gliomab-H (Monoclonals—Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab, or ImmuRAIT-CEA.

In some embodiments, an immunotherapy, utilized as a co-therapy with the microflora modulation described herein, directly or indirectly targets one of more of: a regulatory T cell, myeloid suppressor cell, or dendritic cell. In another aspect, an immunotherapy specifically targets one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-KB (RANK); Receptor activator of nuclear factor-KB (RANK) ligand (RANKL); LAG-3; glucocorticoid-induced tumor necrosis factor receptor family-related gene (GITR; TNFRSF18); indoleamine-pyrrole 2,3-dioxygenase (IDO) or Interleukin-4 receptor (IL-4R). In some embodiments, the immunotherapy acts as an agonist that increases the function of the targeted molecule. In other embodiments, the immunotherapy is an antagonist that inhibits the function of the targeted molecule.

In some embodiments, an immunotherapy, utilized as a co-therapy with the microflora modulation described herein, directly or indirectly targets one of more of a specific cytokine, cytokine receptor, co-stimulatory molecule, co-inhibitory molecule, or immunomodulatory receptor that modulates the immune system. In another aspect, one of the following molecules are targeted by co-treatment with microflora modulation: tumor necrosis factor (TNF) superfamily; tumor necrosis factor-α (TNF-α); tumor necrosis factor receptor (TNFR) superfamily; Interleukin-12 (IL-12); IL-12 receptor; 4-IBB (CD137); 4-IBB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand I (PD-L1: B7-H1); or PD-1 ligand 2 (PD-L2; B7-DC); B7 family; B7-1 (CD80); B7-2 (CD86); B7-H3; B7-H4; GITR/AITR: GITRL/AITRL; BTLA; CD70; CD27; LIGHT; HVEM: Toll-like receptor (TLR) (TLR 1, 2, 3, 4, 5, 6, 7, 8, 9, 10).

In some embodiments, the compositions for and/or methods of modulating microflora in a subject sensitize the cancer cells and/or tumor to treatment by one or more chemotherapeutic agents. In some embodiments, one or more chemotherapies are employed in addition to microflora modulation (e.g., concurrently or serially) to make use of the induced chemotherapeutic sensitivity. In other embodiments, one or more chemotherapeutics are provided as co-therapies with microflora modulation, with or without (known) synergism between the microflora modulation and the chemotherapy.

In some embodiments, exemplary anticancer agents suitable for use in compositions and methods described herein (e.g., co-administered with a β-catenin inhibitor) include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, compositions and methods herein comprise multiple modes for the treatment and/or prevention of cancer. In some embodiments, beneficial microbes are provided/administered (e.g., by a probiotic composition, fecal transplant, etc.) with prebiotics and/or other agents that facilitate the growth of the beneficial microbes. In some embodiments, beneficial microbes are provided/administered (e.g., by a probiotic composition, fecal transplant, etc.) with antimicrobial(s) (e.g., antibiotics) directed to kill or inhibit the growth of detrimental microbes. In some embodiments, prebiotics and/or other agents that facilitate the growth of the beneficial microbes are provided/administered with antimicrobial(s) (e.g., antibiotics) directed to kill or inhibit the growth of detrimental microbes. In some embodiments, beneficial microbes, prebiotics and/or other agents that facilitate the growth of the beneficial microbes, and an antimicrobial(s) (e.g., antibiotics) directed to kill or inhibit the growth of detrimental microbes are all co-administered.

In some embodiments, the co-administered agents are formulated into a single dose and/or composition. In some embodiments, the co-administered agents are in separate doses and/or compositions. In some embodiments in which separate doses and/or compositions are administered, the doses and/or compositions are administered simultaneously, consecutively, or spaced over a time span (e.g., <30 minutes, 1 hour, 2 hours, 4 hours, 6 hours, 12 hours, 1 day, 2 days, 3 days, 4 days, 5 days, 6 days, 1 week, or more, or any suitable ranges therebetween).

In some embodiments, beneficial microbes, prebiotics and/or other agents that facilitate the growth of the beneficial microbes, antimicrobial(s) (e.g., antibiotics) directed to kill or inhibit the growth of detrimental microbes, or any of the above mentioned combinations thereof are administered with a treatment for cancer. In some embodiments, in which the modulation of microflora itself provides treatment for cancer, suitable co-treatments include immunotherapy, chemotherapy, surgery (e.g., tumor removal), radiation, etc. In other embodiments, in which the modulation of microflora sensitizes a subject or the tumor microenvironment to a particular cancer therapy (e.g., an immunotherapy, a chemotherapy, etc.), the particular cancer therapy is administered (e.g., optionally in addition to one or more other cancer therapies to which the subject is not directly sensitized to by the modulation).

In some embodiments, microflora modulation is provided as a co-therapy (e.g., chemotherapy, immunotherapy, etc.) with one or more additional therapies that target and/or bind to specific cancer or tumor cell markers. Such markers may be selected from the group including but not limited to, epidermal growth factor receptor (EGFR, EGFR1, ErbB-1, HER1). ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), 1L-6 receptor, interleukin-4, IL-4 receptor, Cytokine receptors, Class I (hematopoietin family) and Class II (interferon/1L-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC127), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDXS, PTPRK, K-ras (KRAS2), N-ras (NRAS), HRAS, RBAF600, SIRT12, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGATS), HERV-K MEL, KK-LC, LAGE, LAGE-1, CTL-recognized antigen on melanoma (CAMEL), MAGE-A1 (MAGE-1). MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikrein 4, mammaglobin-A, OA1, prostate specific antigen (PSA), prostate specific membrane antigen, TRP-1/, 75. TRP-2 adipophilin, interferon inducible protein absent in melanoma 2 (AIM-2). BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, PRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), etc.

Non-limiting examples of cancers that may be treated with the compositions and methods described herein include, but are not limited to: cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the cancer is a melanoma (e.g., metastatic malignant melanoma), renal cancer (e.g. clear cell carcinoma), prostate cancer (e.g. hormone refractory prostate adenocarcinoma), pancreatic cancer (e.g., adenocarcinoma), breast cancer, colon cancer, gallbladder cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, the cancer is a solid tumor cancer.

In some embodiments, the methods provided herein relate to the treatment and/or prevention of a leukemia. The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia.

In some embodiments, the methods provided herein relate to the treatment and/or prevention of a carcinoma. The term "carcinoma" refers to a malignant growth made up of epithelial cells tending to infiltrate the surrounding tissues, and/or resist physiological and non-physiological cell death signals and gives rise to metastases. Non-limiting exemplary types of carcinomas include, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti.

In some embodiments, the methods provided herein relate to the treatment and/or prevention of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated and/or prevented using the methods described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some embodiments, the cancer treated and/or prevented is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated and/or prevented using methods described herein include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

Cancers prevented and/or treated in certain embodiments also include precancerous lesions, e.g. actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) elastosis and cervical dysplasia.

Cancers prevented and/or treated in some embodimentsinclude non-cancerous or benign tumors, e.g. of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

Some embodiments described herein are particularly useful for the treatment of tumors that do not otherwise respond to immunotherapeutic approaches. In some embodiments, such tumors are non-responsive (or have a reduced response) to T cells (e.g., prevent infiltration of one or more T cell types (e.g., $CD8^+$ T cells) or antigen presenting cells (e.g., dendritic cells (e.g., $CD103^+DCs$, etc.), etc.). In some embodiments, compositions and methods described herein find use in the treatment of cancers in which T cells are not appropriately primed against tumor-associated antigens.

In some embodiments, methods are provided for testing sample (e.g., cell, tissue, population of cells, tumor, blood, urine, saliva, etc.) from a subject for one or more biomarkers of cancer, immune evasion, cancer promoting microenvironment, malignancy-promoting microenvironment, etc. Such biomarkers may comprise nucleic acids, small molecules, proteins, peptides, etc., and may be detected using any suitable assay of technique. In some embodiments, provided herein are DNA-, RNA-, small molecule, and/or protein-based diagnostic methods that either directly or indirectly detect the biomarkers of the evasion of immune response or immunotherapy by cancer cells or tumors. The present invention also provides compositions, reagents, and kits for such diagnostic purposes.

In some embodiments, biomarkers are detected at the nucleic acid (e.g., RNA, 16s rRNA) level. For example, the presence or amount of biomarker nucleic acid (e.g., mRNA) in a sample is determined (e.g., to determine the presence or level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, nucleic acid amplification (e.g., by PCR, RT-PCR, qPCR, etc.), micorarray, Southern and Northern blotting, sequencing, etc. Non-amplified or amplified nucleic acids can be detected by any conventional means. For example, in some embodiments, nucleic acids are detected by hybridization with a detectably labeled probe and measurement of the resulting hybrids. Nucleic acid detection reagents may be labeled (e.g., fluorescently) or unlabeled, and may by free in solution or immobilized (e.g., on a bead, well, surface, chip, etc.).

In some embodiments, biomarkers are detected at the protein level. For example, the presence or amount of biomarker protein in a sample is determined (e.g., to determine the presence or level of biomarker expression or localization). In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized (e.g., on a bead, well, surface, chip, etc.).

In particular embodiments, biomarkers are microbiome biomarkers. In some embodiments, the microbiome of a subject is assayed and depending on the particular microbial population, the responsiveness/resistance of the subject to immunotherapy is characterized. In some embodiments, the presence, absence, or level of one or more bacteria determined during experiments conducted during development of embodiments herein to be indicative and/or causative of immunotherapy responsiveness/resistance (e.g., indicative and/or causative of T cell inflammation) is determined. In some embodiments, bacteria of the species *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum* indicate responsiveness (e.g., levels above a threshold). In some embodiments, bacteria of the species *Ruminococcus obeum* and *Roseburia intestinalis* indicate non-responsiveness (e.g., levels above a threshold).

In some embodiments, samples are obtained from a subject (e.g., a patient or a subject in need of treatment according to the technology provided herein) at any suitable interval of time, varying from minutes to hours apart, days to weeks apart, or even weeks to months apart. Biomarker samples may be obtained multiple times a day, week, month or year. The duration of sampling can also vary. For example, the duration of sampling may be for about a month, about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 30 years, or more. In some embodiments, the sampling is taken prior to or after administration of treatment according to the technology provided herein.

In one embodiment, the sample is taken from a subject being treated for cancer with an immunotherapy. Based on the level of bacteria in the sample, the subject may receive a second immunotherapy that is different from the first immunotherapy. Additionally, the subject may be treated with a mixture of bacteria including but not limited to *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum* prior to administration of the first or second immunotherapy.

In some embodiments, the subject's biomarker (e.g., bacteria) level is compared to a threshold wherein the threshold is determined by the average level of such biomarkers within a population of patients. In particular, the patient population size may include 50, 100, 200, 300, 400, 500, 1000, 2000, 3000, 4000, 5000 and ranges in between of patients who have responded or have not responded to an immunotherapy treatment.

In some embodiments, kits are provided comprising, for example, the probiotic or microflora transplant compositions described herein. Kits may further comprise instructions, cancer treatments, other probiotics, agents to enhance integration of microbes into the subject's microflora, etc.

EXPERIMENTAL

Example 1

Materials and Methods
Patient Fecal Sample Collection

Stool samples were collected from 42 metastatic melanoma patients prior to immunotherapy initiation. Eligible patients were provided an EasySampler Collection Kit (ALPCO) to collect stool sample at home. The stool samples were brought to the lab within 24 hours after collection. DNA was immediately isolated from 250 mg of stool and the rest of the sample was aliquoted and stored at −80° C. Of the 42 patients 38 were thereafter subjected to anti-PD-1 therapy and 4 were given anti-CTLA-4 therapy. Exclusion of the latter 4 patients did not change the downstream conclusions, so they were retained in the analysis.
Microbial DNA Isolation Patient stool samples were handled under BSL2 laminar flow hood using sterile technique. The technician wore gloves, gown, face mask and hair net to prevent contamination of the samples. Isolation of microbial DNA from patient and mouse fecal samples was performed using QIAamp PowerFecal DNA Kit and QIAmp DNA Stool Mini Kit, respectively (Qiagen, Germantown, Md.). DNA concentration was measured using a Nanodrop-nd1000 and the DNA was stored at −80° C.
16S rRNA Gene Amplicon Library Preparation and Sequencing 16S rRNA gene amplicon library preparation and sequencing was performed at the Argonne National Laboratory. PCR amplicon libraries targeting the 16S rRNA encoding gene were produced using a barcoded primer set adapted for the Illumina HiSeq2000 and MiSeq (Ref 9A; herein incorporated by reference in its entirety). DNA sequence data were then generated using Illumina paired-end sequencing at the Environmental Sample Preparation and Sequencing Facility (ESPSF) at Argonne National Laboratory. Specifically, the V4 region of the 16S rRNA gene (515F-806R) was PCR-amplified with region-specific primers that include sequencer adapter sequences used in the Illumina flowcell (refs. 9A, 10A; herein incorporated by reference in their entireties). The forward amplification primer also contains a twelve-base barcode sequence that supports pooling of up to 2,167 different samples in each lane. Each 25 μL PCR reaction contained 9.5 μL of MO BIO PCR Water (Certified DNA-Free), 12.5 μL of QuantaBio's AccuStart II PCR ToughMix (2× concentration, 1× final), 1 μL Golay barcode tagged Forward Primer (5 μM concentration, 200 pM final), 1 μL Reverse Primer (5 μM concentration, 200 pM final), and 1 μL of template DNA. The conditions for PCR were as follows: 94° C. for 3 minutes to denature the DNA, with 35 cycles at 94° C. for 45 s, 50° C. for 60 s, and 72° C. for 90 s; with a final extension of 10 min at 72° C. to ensure complete amplification. Amplicons were then quantified using PicoGreen (Invitrogen) and a plate reader (Infinite® 200 PRO, Tecan). Once quantified, volumes of each of the products were pooled into a single tube so that each amplicon was represented in equimolar amounts. This pool was then cleaned up using AMPure XP Beads (Beckman Coulter) and quantified using a fluorometer (Qubit, Invitrogen). The pool was diluted down to 2 nM, denatured, and further diluted to a final concentration of 6.75 pM with a 10% PhiX spike for sequencing on the Illumina MiSeq. Amplicons were sequenced on a 151 bp×12 bp×151 bp MiSeq run using previously described sequencing primers and procedures. The average sequencing depth for the patient samples was 51,029, ranging from 28,040 to 68,928 reads; the average sequencing depth for mouse samples was 158,728, ranging from 54,632 to 327,216 reads per sample.
Microbial 16S rRNA Gene Amplicon Analysis The microbial 16S rRNA gene amplicon sequencing data from human and mouse facet collections were processed separately using Quantitative Insights Into Microbial Ecology (QIIME) (version 1.91) (Refs. 3A, 11A; herein incorporated by reference in their entireties). Raw reads were trimmed to remove low quality bases and paired-end 3' overlapping mates were merged using SeqPrep (github.com/jstjohn/SeqPrep). The open reference OTU picking protocol was used at 97% sequence identity against the Greengenes database (08/2013 release) (Ref 12A; herein incorporated by reference in its entirety). PyNAST was used to align sequences (Ref 13A; herein incorporated by reference in its entirety) and RDP Classifier was used for taxonomic assignment (Ref 14A; herein incorporated by reference in its entirety).

Analysis of the mouse 16S dataset revealed 519 OTUs differentially abundant between the fast and slow tumor growth groups at FDR-adjusted p<0.05. Among these, 298 OTUs were assigned with known reference IDs and 221 with new reference ID. The new reference OTU IDs are not comparable between different cohorts, hence we focused on the OTUs with known reference IDs. Out of 298 OTUs, 207 OTUs were matched with human donors and used for generation of the heatmap depicted in FIG. 3B. In addition, binary Bray-Curtis dissimilarity index was computed for each donor-mouse sample pair based on presence/absence of matched OTUs. For each pair, OTUs of relative abundance >0.0001 in the donor or the mouse sample was included for the calculation.
BLASTN Methodology To investigate the identity of the OTUs differentially abundant between responders and non-responder patients, the assembled 16S rRNA gene amplicon sequences were characterized by a BLAST search against NCBI bacterial nucleotide sequence database. Using the blastn command line tool and the "megablast" program selection method, the top hits with ≥98% identity to the query sequence were returned from the nucleotide collection database restricted to bacteria, and excluding environmental or uncultured sample sequences. Results are shown in Table 2. For some OTUs there were no hits with ≥98% identity and the top 10 hits are listed with regardless of the % identity value.

Metagenomic Shotgun Sequencing

Metagenomic shotgun sequencing was performed at the Marine Biological Laboratory affiliated with the University of Chicago. The quantity of the DNA sample was measured using Picogreen (Invitrogen). DNA was then sheared using a Covaris and the libraries were constructed with the Nugen Ovation Rapid DR Multiplex System (PCR-free). The aimed insert size is between 400-600 bp. Amplified libraries were visualized on an Agilent DNA1000 chip or Caliper HiSens Bioanalyzer assay, pooled at equimolar concentrations and size selected using a Sage PippinPrep 2% cassette. The library pool was quantified using a Kapa Biosystems qPCR library quantification protocol, then sequenced on the Illumina NextSeq in a 2×150 paired-end sequencing run using dedicated read indexing. The samples were demultiplexed with bcl2fastq. An average of 80.4 million reads were generated per sample, ranging from 38.9 to 156.7 million reads.

Microbial Shotgun Metagenomics Analysis

The microbial shotgun metagenome sequencing data from human facet collections were taxonomically profiled using Metagenomic Phylogenetic Analysis (MetaPhlAn 2) (Ref 15A; herein incorporated by reference in its entirety). The average sequencing depth was 80369403 (±33712841), ranging from 38841706 to 156677784 reads per sample. Species-level taxonomic relative abundances were inferred for all samples (Ref 16A; herein incorporated by reference in its entirety). Metagenomic reads were mapped against a catalog of ~1 million clade-specific marker sequences identified from 17000 reference genomes currently spanning bacteria, archaea, eukaryotes and virus phylogenies to assign reads to microbial clades. The relative abundance of each taxonomic unit in each sample was estimated by normalizing read counts assigned to each clade by the nucleotide length of its markers and by the sum of all weighted read counts in this clade including all subclades. To compare species identified from 16S and shotgun sequencing, the profiled bacterial species were then compared to the taxonomy of OTUs generated from 16S sequencing at family level, and the statistical dependence between the relative abundance of 16S OTUs and each matched shotgun species was determined using Spearman's rank correlation tests, followed by filtering for those with positive correlation and at $P<0.05$.

Model Training and Validation

To evaluate the predictive power of 63 OTUs differentially present between NR (n=26) and R (n=16) groups, a support vector machine (SVM) model with radial basis function (RBF) kernel and estimated the variable importance of each predictor using Caret (version 6.0-76) (CRAN.R-project.org/package=caret) was built. 21 OTUs with near zero-variance, highly correlated (Spearman's $\rho>0.75$), and/or of potential linear dependencies were identified and removed using functions nearZeroVar, findCorrelation, and findLinearCombos, respectively. 42 OTUs were carried on for further analysis. The 42 patient samples were randomly split into training and test sets by 60% (n=25) to 40% ratio (n=17). The mean and standard deviation of the training set was computed and used to center and scale the training and test data separately by the preProcess function. The training set was then used to tune the parameters and select the best model using 5-fold cross validation with ROC metrics to evaluate model performance. Relative importance of each predictor was estimated by ROC curve analysis using function filterVarImp. After training, the test set was used to independently assess the performance of the final model, and metrics such as balanced accuracy, sensitivity, specificity, positive prediction value (PPV), negative prediction value (NPV), and area under the curve (AUC) were computed using the confusionMatrix function from caret package. The above model training and testing procedure was performed iteratively 100 times with 100 different random seeds to evaluate the robustness and stability of the OTU predictors in the classification of NR and R groups from the study cohort.

qPCR Validation of Metagenomic and 16S rRNA Gene Sequencing of Fecal Samples

The abundance of some of the bacterial species identified with the metagenomic and 16S rRNA gene amplicon sequencing approaches were further measured by qPCR using previously validated subgroup- or species-specific primers and probes (Refs. 17A-29A; herein incorporated by reference in their entireties) and SYBR Green or TaqMan PCR master mix (Applied Biosystems). The primers and probes were synthesized by Integrated DNA Technologies (Coralville, Iowa) and Life Technologies, respectively. qPCR was performed on StepOnePlus Real-Time PCR System (Applied Biosystems, Foster City, Calif.) and analyzed with StepOnePlus Software. The primer concentrations were as previously described (Table 5). The cycling conditions for the TaqMan-based reactions were 50° C. for 2 min, 95° C. for 10 min, 40 cycles of 95° for 15 secs, 60-65° C. for 1 min, with varying annealing temperatures depending on the primer pair. The cycling conditions for the SYBR Green-based reactions were 95° C. for 10 min, 40 cycles of 95° for 15 sec, 60-75° C. for 10-40 sec, 72° C. for 20-50 sec, with varying annealing temperatures and times depending on the primer pair. Fluorescence signal was detected at the end of each cycling stage. For some reactions, fluorescence detection was done during an additional 15 sec step at a higher temperature to minimize signal from primer dimers and minor non-target products (Ref 18A; herein incorporated by reference in its entirety). Melt curve analysis was performed to confirm amplification specificity. The results were expressed as relative abundance normalized to the total bacterial load. Specifically, to calculate the total bacterial load, qPCR was performed using previously described universal bacterial primers (Ref 30A; herein incorporated by reference in its entirety). A standard curve was generated using the PCR blunt vector (Invitrogen) containing a single copy of the 16S rRNA gene derived from a member of the Porphyromonadaceae family (Ref 31A; herein incorporated by reference in its entirety) and the total 16S rRNA gene copies per ng DNA was calculated for each sample. Relative abundance for each species was expressed as $2^{-Ct}$ normalized to the number of total 16S rRNA gene copies per ng DNA in each sample. A summation qPCR score was computed per individual sample taking into consideration the abundance of 10 validated qPCR targets (*Enterococcus faecium, Collinsella aerofaciens, Bifidobacterium adolescentis, Klebsiella pneumoniae, Veillonella* sp., *Parabacteroides merdae, Lactobacillus* sp., *Bifidobacterium longum, Ruminococcus obeum* and *Roseburia intestinalis*). First, data transformation was applied on the relative abundance to bring signal close to Gaussian distribution. The relative abundance of each species was multiplied by a constant (7.3×10^19) to bring all values larger than 1, log 10 transformed, and scaled by dividing the value by their root mean square across samples. The abundance of *Ruminococcus obeum* and *Roseburia intestinalis* (more abundant in non-responders) were multiplied by (−1). The sum of the transformed abundance of the 10 qPCR results was calculated to generate the score, and compared between groups of interest using two-sided Student's t-test.

RNAseq of Tumor Samples and Data Analysis

RNA was isolated from tumor samples using the QIAGEN AllPrep DNA/RNA FFPE kit (Qiagen, Hilden, Germany) according to the manufacturer's instructions. The quality of RNA was measured on Agilent 2100 Bioanalyzer (Agilent Technologies, Santa Clara, USA). cDNA was reverse transcribed from RNA and used for library preparation following dUTP strand-specific protocol by the University of Chicago Genomics Core Facility. Ribosome RNA was removed using the Ribo-Zero rRNA Removal Kit (Human) (Illumina, San Diego, USA). Sequence reads were generated on an Illumina HiSeq 4000 instrument at the Functional Genomics Facility. An average of 133.3 million 2×100 bp paired-end (PE) reads were generated for each sample, ranging from 93.2 to 208.0 million reads. The quality of raw reads was assessed by FastQC (Ref 32A; herein incorporated by reference in its entirety) (v0.11.5). Reads were aligned to human reference transcriptome with Gencode gene annotation (v26, GRCh38) by Kallisto (Ref 33A; herein incorporated by reference in its entirety) (v0.43.1) with the strand-specific mode, which implements kmer-based pseudoalignment algorithm for accurate quantification of transcripts from RNAseq data and is robust to errors in the reads. Transcript abundance was quantified at transcript level specifying strand-specific protocol, summarized into gene level using tximport (Ref 34A; herein incorporated by reference in its entirety) (v1.4.0), normalized by trimmed mean of M values (TMM) method, and log 2-transformed for further analysis. Selected transcripts (PD-L1 and PD-1) were compared between responders and non-responders.

Whole Exome+UTR Sequencing of Tumor Samples and Data Analysis

Tumor DNA were isolated from tumor samples using the QIAGEN AllPrep DNA/RNA FFPE kit (Qiagen, Hilden, Germany), and the integrity and quantification were evaluated on an Agilent 2100 Bioanalyzer (Agilent Technologies, Santa Clara, USA) and qubit (Thermo Fisher, Waltham, USA), respectively. 200 ng of DNA was used for whole exome+UTR capture using the Agilent SureSelect Human All Exon V6 plus UTR kit (Agilent Technologies, Santa Clara, USA). Sequence reads were generated on an Illumina NextSeq 500 instrument (Illumina, San Diego, USA) at the University of Chicago Functional Genomics Facility. An average of 62.2 million 2×100 bp paired-end (PE) reads were generated for each sample, ranging from 51.9 to 70.9 million reads.

The raw sequencing data were analyzed by an in-house pipeline constructed for WES analyses of paired or unpaired cancer genomes. The quality of raw reads is assessed by FastQC (ref 32A; herein incorporated by reference in its entirety) (v0.11.5), and preprocessed to trim adaptors and merge 3' overlapping mates using SeqPrep (v1.2). Reads were aligned to human reference genome (GRCh37) using BWA-MEM (Ref 35A; herein incorporated by reference in its entirety) (v0.7.15) with soft-clipping option activated by default. Read duplicates were marked using Sambamba (Ref 36A; herein incorporated by reference in its entirety) (v0.6.3) and alignments of mapping quality<30 were removed. Reads alignment was further refined using insertions/deletions realignment and base quality score recalibration (BQSR) using GATK (Ref 37A; herein incorporated by reference in its entirety) (v3.8.0). Callable loci were collected from the alignment using GATK CallableLoci program, and merged with Agilent V6+UTR exome capture target regions provided by the vendor. Putative somatic mutations were detected by MuTect2 (Ref 38A; herein incorporated by reference in its entirety) (v3.8.0), which identifies somatic single nucleotide variants (SNVs) and indels from high-quality bases using the tumor-only mode. Stringent filters were applied on variants that passed the default setting of the caller to further remove potential germline variants identified as those present in dbSNP database, or at allele frequency (AF)≥0.0001 in 1000 Genomes Project (G1000) (Ref 39A; herein incorporated by reference in its entirety), the NHLBI Grand Opportunity Exome Sequencing Project (ESP) (Ref 40A; herein incorporated by reference in its entirety), or the Exome Aggregation Consortium (ExAC) (Ref 42A; herein incorporated by reference in its entirety) on non-TCGA samples. Variants that passed all filters were carried on for annotation using ANNOVAR. The somatic mutation burden was calculated by the total number of mutations that were predict to cause protein sequencing change, including non-synonymous, stopgain, and stoploss SNVs, frameshift and non-frameshift indels, and variants that modify splicing sites.

Immunohistochemistry of Tumor Samples

Tissue sections were prepared from paraffin-embedded tumor samples from 5 responders and 10 non-responder patients. The slides were stained using Leica Bond RX automatic stainer. Bond™ Epitope Retrieval Solution I (Leica Biosystems, CatNo: AR9961) was applied for 20 minutes. A primary anti-CD8 antibody (clone C8/144B from Dako; 1:400 dilution) was applied for 25 minutes. The primary antibody was then detected with Bond™ Polymer Refine Detection kit (Leica Biosystems, CatNo: DS9800). The $CD8^+$ cell density was expressed as a ratio of $CD8^+$ cells/pixel to total cells/pixel using inForm Cell Analysis software (PerkinElmer).

Animals, Fecal Transfer, and Tumor Model

Specific pathogen-free (SPF) C57BL/6 mice were obtained from Taconic Biosciences (Hudson, N.Y.). SPF mice were fed Teklad irradiated 2918 diet (Envigo), or in some cases autoclaved 5K67 diet (Lab Diet, St. Louis, Mo.), and housed in the University of Chicago SPF animal facility. Germ-free (GF) C57BL/6 mice were initially purchased from Taconic biosciences, then bred and housed in flexible-film isolators in the University of Chicago Gnotobiotic Research Animal Facility and fed autoclaved 5K67 diet. Some GF mice were gifted by Dr. Eugene Chang at the University of Chicago. For all experiments, 6-8-week-old mice were used. The C57BL/6-derived melanoma cell line B16.F10.SIY (henceforth referred to as B16.SIY) was generated (Ref 43A; herein incorporated by reference in its entirety). For tumor growth experiments, some GF mice were colonized with fecal microbiota from 3 responders and 3 non-responder patients, or microbiota from SPF mice by oral gavage. 200 mg of human stool was thawed and suspended in 3 ml of PBS or mouse fecal pellets were collected fresh and suspended in 1 ml of PBS per pellet. After settling of the particulate material, each mouse was gavaged with 10 ml/kg body weight (approximately 200 μl per mouse) of the fecal supernatant. Two weeks after gavage, the colonized mice were injected subcutaneously with $1×10^6$ B16.SIY tumor cells. Some mice were injected i.p. 7, 10, 13, and 16 days after tumor inoculation with 100 μg of anti-PD-L1 monoclonal antibody (BioXCell, 10F.9G2). Tumor size was measured three times per week until the endpoint and tumor volume was determined as length×width$^2$×0.5. Microbiota composition of the colonized mice was assessed with 16S rRNA gene amplicon sequencing of DNA extracted from fecal samples collected 4 weeks after colonization. Taconic SPF mice were used as a reference control. The experimental animal procedures were approved by the University of Chicago Animal Care and Use Committee.

SIY Pentamer Analyses

For immune profiling, cells were labeled with a PE-MHC class I pentamer (Proimmune) consisting of murine H-2K$^b$ complexed to SIYRYYGL (SIY) peptide or to an irrelevant SIINFEKL peptide. Tumor cell suspensions were subsequently stained with CD3-AX700 (Ebioscience, 17A2), CD8α-Pacific Blue (Biolegend, 53-6.7), CD4-BV711 (Biolegend, RM4-5), CD44-FITC (BD, IM7), and Fixable Viability Dye-eFluor780 (Ebioscience). Once stained, cells were fixed with 1% paraformaldehyde and analyzed on LSRFortessa flow cytometer with FACSDiva software (BD). Data analysis was performed using FlowJo software (Tree Star).

IFN-γ ELISPOT

ELISPOT was carried out using anti-IFN-γ capture/detection antibody pair from BD Biosciences. ELISPOT plates (Millipore, MAIP 54510) were coated with capture antibody (CatNo: 51-2525KD) overnight at 4° C. and then blocked with DMEM+10% FBS for 2 hours at room temperature. Splenocytes were enumerated using flow cytometry, plated at 10$^6$ cells per well and stimulated with 160 nM SIY peptide or irrelevant OVA peptide as negative control, or 500 ng/ml ionomycin+50 ng/ml PMA as positive control, overnight at 37° C. The following day, IFN-γ spots were detected with biotinylated detection antibody (CatNo: 51-1818KZ), followed by streptavidin-HRP and AEC substrate kit (all from BD Biosciences). The spot number and size were quantified using an Immunospot Series 3 Analyzer and ImmunoSpot software (Cellular Technology).

Statistical Analysis

Tumor growth curves were analyzed using two-way ANOVA with Tukey's multiple comparisons post-test using GraphPad PRISM. For other comparisons between two groups, including evaluating significance in immune profiling or quantitative PCRs, unpaired, two-tailed Student's t-test or non-parametric Mann-Whitney U test was used as indicated in the figure legends. Microbial composition comparisons were performed using non-parametric t-tests. For multiple comparisons, p-value was adjusted using Benjamini-Hochberg FDR correction (Ref 44A; herein incorporated by reference in its entirety). Spearman's rank correlation coefficient ρ was used for measuring statistical dependence between relative abundance of bacteria produced by different platforms. $P<0.05$ was considered statistically significant and denoted as follows: *$P<0.05$, $P<0.01$, *$P<0.001$, ****$P<0.0001$. Statistical analysis was performed using GraphPad PRISM and R.

Results

To evaluate whether commensal bacterial composition might be associated with clinical efficacy of checkpoint blockade immunotherapy, stool samples were collected from 42 patients prior to treatment as part of a multi-dimensional biomarker analysis in metastatic melanoma. Clinical response rate was determined in a blinded fashion from biomarker results, using Response Evaluation Criteria In Solid Tumors (RECIST) version 1.1. There were 16 responders (from here on, referred to as R) and 26 non-responders (NR), giving a response rate of 38% in line with published clinical data with anti-PD-1 agents in metastatic melanoma (Refs. 1B, 2B; herein incorporated by reference in their entireties). No major differences in patient characteristics were observed in R vs. NR, except a borderline difference in prior (but not current) smoking history (Table 1).

TABLE 1

Baseline patient characteristics with Responders Vs. Non Responders

| | | Total (N = 42) | Responders | Non Responders | P-value | OR (95% CI) |
|---|---|---|---|---|---|---|
| Gender | Female | 22 | 8 | 14 | 1.00 | 0.86 (0.21, 3.56) |
| | Male | 20 | 8 | 12 | 1.00 | 1.16 (0.28, 4.84) |
| Race | White | 39 | 15 | 24 | 1.00 | 1.24 (0.06, 78.56) |
| | Other Race$^f$ | 3 | 1 | 2 | 1.00 | 0.8 (0.01, 16.73) |
| Age | <50 | 4 | 2 | 2 | 0.63 | 1.69 (0.11, 25.78) |
| | 51-70 | 28 | 12 | 16 | 0.51 | 1.85 (0.4, 10.11) |
| | 71+ | 10 | 2 | 8 | 0.27 | 0.33 (0.03, 2.03) |
| BMI* | Underweight | 1 | 0 | 1 | 1.00 | 0 (0, 63.31) |
| | Normal | 14 | 5 | 9 | 1.00 | 0.86 (0.18, 3.85) |
| | Overweight | 17 | 6 | 11 | 1.00 | 0.82 (0.18, 3.46) |
| | Obese | 10 | 5 | 5 | 0.46 | 1.88 (0.35, 10.22) |
| Smoking | Never | 25 | 7 | 18 | 0.12 | 0.36 (0.08, 1.5) |
| | Former | 13 | 8 | 5 | 0.05 | 4.04 (0.87, 21.18) |
| | Current | 4 | 1 | 3 | 1.00 | 0.52 (0.01, 7.18) |
| EtOH** | No Current Use | 18 | 7 | 11 | 1.00 | 1.06 (0.25, 4.42) |
| | Occasional | 17 | 6 | 11 | 1.00 | 0.82 (0.18, 3.46) |
| | Moderate | 6 | 2 | 4 | 1.00 | 0.79 (0.06, 6.4) |
| | Heavy | 1 | 1 | 0 | 0.38 | NE (0.04, NE) |
| ECOG PS | 0 | 25 | 9 | 16 | 0.76 | 0.81 (0.19, 3.45) |
| | 1 | 17 | 7 | 10 | 0.76 | 1.24 (0.29, 5.24) |
| Prior Therapy | None | 27 | 11 | 16 | 0.75 | 1.36 (0.31, 6.59) |
| | 1 | 10 | 4 | 6 | 1.00 | 1.11 (0.19, 5.85) |
| | >1 | 5 | 1 | 4 | 0.63 | 0.37 (0.01, 4.29) |
| LDH*** | Normal | 32 | 11 | 21 | 0.46 | 0.53 (0.1, 2.86) |
| | Elevated | 10 | 5 | 5 | 0.46 | 1.88 (0.35, 10.22) |
| Melanoma sub-type | Cutaneous | 35 | 14 | 21 | 0.69 | 1.65 (0.23, 19.6) |
| | Mucosal | 6 | 2 | 4 | 1.00 | 0.79 (0.06, 6.4) |
| | Uveal | 1 | 0 | 1 | 1.00 | 0 (0, 63.31) |

TABLE 1-continued

Baseline patient characteristics with Responders Vs. Non Responders

|  |  | Total (N = 42) | Responders | Non Responders | P-value | OR (95% CI) |
|---|---|---|---|---|---|---|
| Mutation**** | BRAF | 16 | 6 | 10 | 1.00 | 0.96 (0.21, 4.1) |
|  | RAS | 9 | 4 | 5 | 0.71 | 1.39 (0.23, 7.93) |
|  | Other | 4 | 1 | 3 | 1.00 | 0.52 (0.01, 7.18) |
|  | None | 10 | 4 | 6 | 1.00 | 1.11 (0.19, 5.85) |
|  | Unknown | 3 | 1 | 2 | 1.00 | 0.8 (0.01, 16.73) |
| M stage | M1a | 7 | 3 | 4 | 1.00 | 1.26 (0.16, 8.81) |
|  | M1b | 11 | 3 | 8 | 0.49 | 0.53 (0.08, 2.77) |
|  | M1c | 24 | 10 | 14 | 0.75 | 1.42 (0.34, 6.29) |
| Sites of metastatic disease | ≥3 | 10 | 6 | 4 | 0.14 | 3.2 (0.6, 19.19) |
|  | <3 | 32 | 10 | 22 | 0.14 | 0.31 (0.05, 1.66) |
| Prior brain metastases | Yes | 4 | 1 | 3 | 1.00 | 0.52 (0.01, 7.18) |
|  | No | 38 | 15 | 23 | 1.00 | 1.93 (0.14, 109.39) |

ECOG; Eastern Cooperative Oncology Group,
LDH; Lactate Dehydrogenase;
PS; Performance status
*BMI; Body Mass Index, Underweight (<18.5), Normal (18.5 to 24.9), Overweight (25 to 29.9), Obese (>30)
**EtOH, alcohol consumption reported; occasional (0.1-4), moderate (5-11), heavy (12+) drinks per week
***LDH institutional upper limit of normal is 245 units/liter
****Other mutations include: NF1, KIT, GNAQ, GNA11
ƒOther Race Than White include: Black, African-American, American Indian or Alaska Native, Patient Decline Information
NE = not evaluable.

Figure 4A:
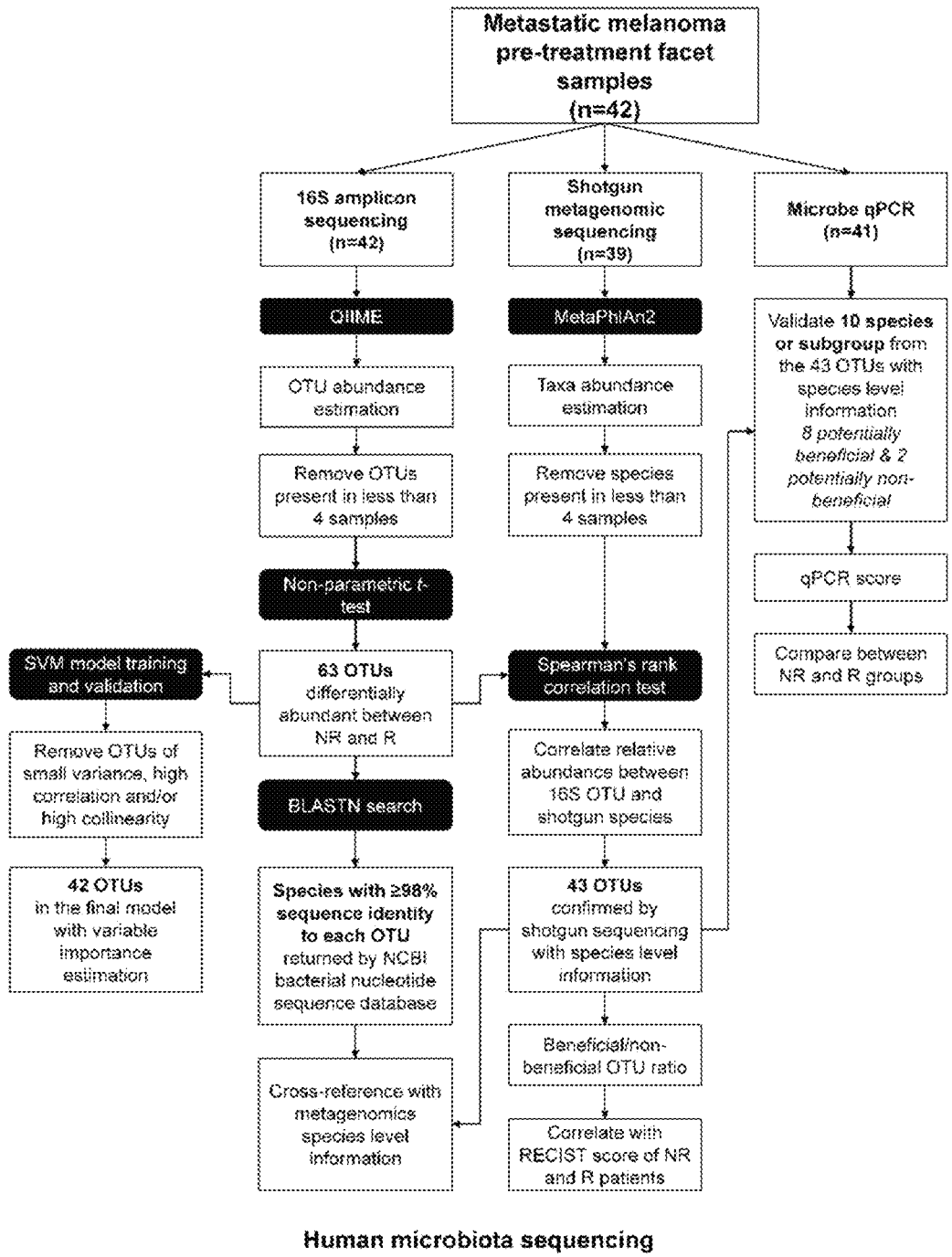
Figure 5:
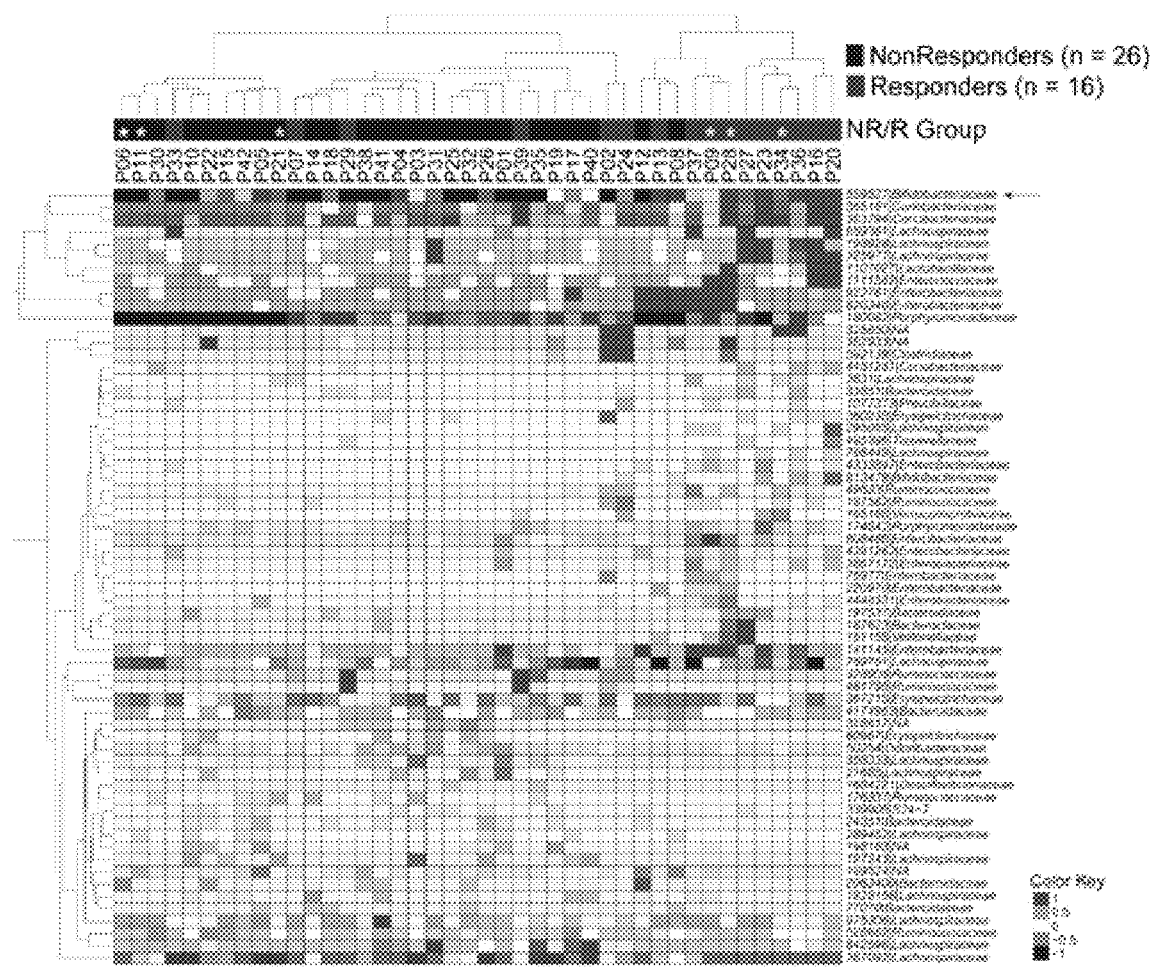
FIG. 5. Segregation of responder and non-responder samples based on relative abundance data for the 63 differentially abundant OTUs determined with 16S sequencing using unadjusted, non-parametric t test. (62 OTUs were significantly different with P<0.05; 1 OTU, Bifidobacteriaceae OTU 559527 indicated with arrow, approached significance with P<0.058). Columns depict individual patients clustered using unsupervised hierarchical clustering with Euclidean distance. Asterisks indicate samples used in further in-vivo experiments. Annotation bar above the heatmap indicates clinical response to immunotherapy. The ID of de-novo assembled OTUs (new clean-up reference OTUs picked by QIIME) were abbreviated to show only the unique identifier digits, and the full OTU IDs are provided in Table 2.

To determine whether the composition of the commensal microbiota is associated with clinical response, three methods for DNA sequence-based bacterial identification were integrated (FIG. 4A). First, using 16S rRNA sequencing, genus-level taxa present at different abundance in R vs. NR we identified (Table 2). A BLAST search of the 16S rRNA sequences against the NCBI database was utilized to reveal species-level identities. Further level of confidence in species identification was gained by matching the genus-level taxa from the 16S rRNA dataset to species-level identities revealed by metagenomic shotgun sequencing (Table 3A-B). Species-specific qPCR was employed for those candidate species having previously validated primers (Table 4A-B). Compared to the 16S rRNA analysis, the metagenomic sequencing yielded a smaller number of species differentially represented in R vs. NR, which significantly overlapped with the 16S results (Table 5). Treating these assays as a screen for maximizing the number of candidate species, the 16S rRNA sequencing method was utilized as a starting point in analysis.

TABLE 2

16S rRNA sequencing

| OTU | Test-Statistic | P value | NonResponder_mean | Responder_mean | taxonomy |
|---|---|---|---|---|---|
| 1111582 | −1.591732208 | 0.000999001 | 0.576923077 | 71.3125 | k_Bacteria; p_Firmicutes; c_Bacilli; o_Lactobacillales; f_Enterococcaceae; g_Enterococcus; s_ |
| 4333897 | −3.274533619 | 0.001998002 | 0.038461538 | 0.625 | k_Bacteria; p_Proteobacteria; c_Gammaproteobacteria; o_Enterobacteriales; f_Enterobacteriaceae; g_; s_ |
| 363794 | −1.839972439 | 0.003996004 | 4.846153846 | 56.9375 | k_Bacteria; p_Actinobacteria; c_Coriobacteriia; o_Coriobacteriales; f_Coriobacteriaceae; g_Collinsella; s_aerofaciens |
| 3867172 | −3.115289034 | 0.005994006 | 0.115384615 | 0.9375 | k_Bacteria; p_Proteobacteria; c_Gammaproteobacteria; o_Enterobacteriales; f_Enterobacteriaceae; g_; s_ |
| New.CleanUp.ReferenceOTU49633 | −2.863148132 | 0.005994006 | 0.153846154 | 0.875 | k_Bacteria; p_Firmicutes; c_Clostridia; o_Clostridiales; f_Ruminococcaceae; g_; s_ |

TABLE 2-continued

| | | 16S rRNA sequencing | | | |
|---|---|---|---|---|---|
| OTU | Test-Statistic | P value | NonResponder_mean | Responder_mean | taxonomy |
| 365181 | −1.719135039 | 0.006993007 | 3.423076923 | 37.625 | k_Bacteria; p_Actinobacteria; c_Coriobacteriia; o_Coriobacteriales; f_Coriobacteriaceae; g_Collinsella; s_aerofaciens |
| 4451251 | −2.958594851 | 0.006993007 | 0.076923077 | 0.625 | k_Bacteria; p_Actinobacteria; c_Coriobacteriia; o_Coriobacteriales; f_Coriobacteriaceae; g_Atopobium; s_ |
| 1684221 | 2.903506373 | 0.007992008 | 0.692307692 | 0.1875 | k_Bacteria; p_Proteobacteria; c_Deltaproteobacteria; o_Desulfovibrionales; f_Desulfovibrionaceae; g_Desulfovibrio; s_ |
| 813479 | −2.424212194 | 0.007992008 | 0.038461538 | 0.6875 | k_Bacteria; p_Actinobacteria; c_Actinobacteria; o_Bifidobacteriales; f_Bifidobacteriaceae; g_Bifidobacterium; s_ |
| New.CleanUp.ReferenceOTU24351 | 3.071336285 | 0.00999001 | 0.5 | 0 | k_Bacteria; p_Bacteroidetes; c_Bacteroidia; o_Bacteroidales; f_Bacteroidaceae; g_Bacteroides; s_ |
| 659361 | −2.029898573 | 0.010989011 | 0.153846154 | 20.5 | k_Bacteria; p_Firmicutes; c_Clostridia; o_Clostridiales; f_Lachnospiraceae; g_Dorea; s_ |
| 187623 | −2.236097332 | 0.011988012 | 0.192307692 | 1.1875 | k_Bacteria; p_Bacteroidetes; c_Bacteroidia; o_Bacteroidales; f_Bacteroidaceae; g_Bacteroides; s_ |
| 198183 | 2.53390364 | 0.011988012 | 0.692307692 | 0.0625 | k_Bacteria; p_Firmicutes; c_Clostridia; o_Clostridiales; f_; g_; s_ |
| 358333 | 2.414385239 | 0.011988012 | 1.038461538 | 0.125 | k_Bacteria; p_Firmicutes; c_Clostridia; o_Clostridiales; f_Lachnospiraceae; g_Blautia; s_ |
| 325977 | −2.399267823 | 0.012987013 | 1.384615385 | 9.8125 | k_Bacteria; p_Firmicutes; c_Clostridia; o_Clostridiales; f_Lachnospiraceae; g_[Ruminococcus]; s_ |
| 197562 | −2.464382476 | 0.013986014 | 0.076923077 | 0.625 | k_Bacteria; p_Firmicutes; c_Clostridia; o_Clostridiales; f_Ruminococcaceae; g_; s_ |
| 289452 | 2.602400195 | 0.013986014 | 0.307692308 | 0 | k_Bacteria; p_Firmicutes; c_Clostridia; o_Clostridiales; f_Lachnospiraceae; g_; s_ |
| 461795 | −2.046964459 | 0.014985015 | 0.076923077 | 2.0625 | k_Bacteria; p_Firmicutes; c_Clostridia; |

TABLE 2-continued

| 16S rRNA sequencing | | | | | |
|---|---|---|---|---|---|
| OTU | Test-Statistic | P value | NonResponder_mean | Responder_mean | taxonomy |
| 185186 | −2.659855246 | 0.015984016 | 0 | 0.5 | o_Clostridiales; f_Ruminococcaceae; g_Oscillospira; s_ |
| 220970 | −2.681219889 | 0.015984016 | 0 | 0.375 | k_Bacteria; p_Verrucomicrobia; c_Verrucomicrobiae; o_Verrucomicrobiales; f_Verrucomicrobiaceae; g_Akkermansia; s_muciniphila |
| 4391262 | −2.544079887 | 0.015984016 | 0.192307692 | 0.75 | k_Bacteria; p_Proteobacteria; c_Gammaproteobacteria; o_Enterobacteriales; f_Enterobacteriaceae; g_Klebsiella; s_ |
| 786449 | −2.872972025 | 0.015984016 | 0 | 0.25 | k_Bacteria; p_Proteobacteria; c_Gammaproteobacteria; o_Enterobacteriales; f_Enterobacteriaceae; g_; s_ |
| 1077373 | −2.667487558 | 0.016983017 | 0 | 0.3125 | k_Bacteria; p_Firmicutes; c_Clostridia; o_Clostridiales; f_Lachnospiraceae; g_; s_ |
| 295085 | −2.031498001 | 0.017982018 | 0 | 0.5 | k_Bacteria; p_Bacteroidetes; c_Bacteroidia; o_Bacteroidales; f_Prevotellaceae; g_Prevotella; s_ |
| 181155 | −1.44077663 | 0.01998002 | 0.076923077 | 6 | k_Bacteria; p_Firmicutes; c_Clostridia; o_Clostridiales; f_Lachnospiraceae; g_Blautia; s_ |
| 325850 | −2.480422027 | 0.01998002 | 0.076923077 | 17.125 | k_Bacteria; p_Firmicutes; c_Clostridia; o_Clostridiales; f_Veillonellaceae; g_Veillonella; s_dispar |
| 367092 | 2.416382368 | 0.01998002 | 13.88461538 | 2.625 | k_Bacteria; p_Proteobacteria; c_Alphaproteobacteria; o_RF32; f_; g_; s_ |
| New.CleanUp.ReferenceOTU75977 | −2.659855246 | 0.01998002 | 0 | 0.5 | k_Bacteria; p_Firmicutes; c_Clostridia; o_Clostridiales; f_Lachnospiraceae |
| 174842 | −2.370319725 | 0.020979021 | 0.423076923 | 1.3125 | k_Bacteria; p_Proteobacteria; c_Gammaproteobacteria; o_Enterobacteriales; f_Enterobacteriaceae; g_; s_ |
| 180082 | −2.219337047 | 0.021978022 | 109.3846154 | 253.75 | k_Bacteria; p_Bacteroidetes; c_Bacteroidia; o_Bacteroidales; f_Porphyromonadaceae; g_Parabacteroides; s_distasonis |
| | | | | | k_Bacteria; p_Bacteroidetes; c_Bacteroidia; o_Bacteroidales; f_Porphyromonadaceae; g_Parabacteroides; s_ |

TABLE 2-continued 16S rRNA sequencing

| OTU | Test-Statistic | P value | NonResponder_mean | Responder_mean | taxonomy |
|---|---|---|---|---|---|
| 808486 | −2.189498747 | 0.021978022 | 0.5 | 1.875 | k_Bacteria; p_Proteobacteria; c_Gammaproteobacteria; o_Enterobacteriales; f_Enterobacteriaceae; g_; s_ |
| 339905 | 2.407682083 | 0.022977023 | 0.384615385 | 0.0625 | k_Bacteria; p_Bacteroidetes; c_Bacteroidia; o_Bacteroidales; f_S24-7; g_; s_ |
| 592139 | −1.321911854 | 0.024975025 | 0.115384615 | 40.875 | k_Bacteria; p_Firmicutes; c_Clostridia; o_Clostridiales; f_Clostridiaceae; g_Clostridium; s_ |
| 922761 | −1.755181534 | 0.024975025 | 3.653846154 | 47.875 | k_Bacteria; p_Proteobacteria; c_Gammaproteobacteria; o_Enterobacteriales; f_Enterobacteriaceae; g_; s_ |
| New.CleanUp.ReferenceOTU3631 | −2.585685376 | 0.024975025 | 0.038461538 | 0.375 | k_Bacteria; p_Firmicutes; c_Clostridia; o_Clostridiales; f_Lachnospiraceae; g_Blautia; s_ |
| 199524 | 2.384248595 | 0.027972028 | 1.269230769 | 0.1875 | k_Bacteria; p_Firmicutes; c_Clostridia; o_Clostridiales |
| 2063400 | 2.065375831 | 0.02997003 | 0.923076923 | 0.0625 | k_Bacteria; p_Bacteroidetes; c_Bacteroidia; o_Bacteroidales; f_Bacteroidaceae; g_Bacteroides; s_ |
| 4448331 | −2.143054695 | 0.031968032 | 0.115384615 | 0.625 | k_Bacteria; p_Proteobacteria; c_Gammaproteobacteria; o_Enterobacteriales; f_Enterobacteriaceae; g_; s_ |
| 352933 | 1.836190984 | 0.032967033 | 0.807692308 | 11.6875 | k_Bacteria; p_Firmicutes; c_Clostridia; o_Clostridiales; f_; g_; s_ |
| New.CleanUp.ReferenceOTU50254 | 2.394751585 | 0.032967033 | 1.192307692 | 0.3125 | k_Bacteria; p_Bacteroidetes; c_Bacteroidia; o_Bacteroidales; f_[Odoribacteraceae]; g_Odoribacter; s_ |
| 176337 | 2.39665494 | 0.034965035 | 0.423076923 | 0 | k_Bacteria; p_Firmicutes; c_Clostridia; o_Clostridiales; f_Ruminococcaceae; g_; s_ |
| 842596 | 2.08340893 | 0.034965035 | 3.307692308 | 0.5 | k_Bacteria; p_Firmicutes; c_Clostridia; o_Clostridiales; f_Lachnospiraceae; g_Coprococcus; s_ |
| New.CleanUp.ReferenceOTU21685 | 2.172568314 | 0.034965035 | 0.653846154 | 0 | k_Bacteria; p_Firmicutes; c_Clostridia; o_Clostridiales; f_Lachnospiraceae; g_; s_ |

TABLE 2-continued

| | | 16S rRNA sequencing | | | |
|---|---|---|---|---|---|
| OTU | Test-Statistic | P value | NonResponder_mean | Responder_mean | taxonomy |
| New.CleanUp.ReferenceOTU60967 | 2.223328377 | 0.035964036 | 0.423076923 | 0 | k_Bacteria; p_Firmicutes; c_Erysipelotrichi; o_Erysipelotrichales; f_Erysipelotrichaceae; g_; s_ |
| 198928 | −1.841787835 | 0.038961039 | 1.461538462 | 7.8125 | k_Bacteria; p_Firmicutes; c_Clostridia; o_Clostridiales; f_Lachnospiraceae; g_[Ruminococcus]; s_ |
| 197343 | 2.136989115 | 0.041958042 | 0.961538462 | 0.125 | k_Bacteria; p_Firmicutes; c_Clostridia; o_Clostridiales; f_Lachnospiraceae; g_; s_ |
| 328617 | 2.04397235 | 0.041958042 | 0.807692308 | 0.1875 | k_Bacteria; p_Bacteroidetes; c_Bacteroidia; o_Bacteroidales; f_Bacteroidaceae; g_Bacteroides |
| 328905 | −1.885076484 | 0.041958042 | 0.5 | 8.125 | k_Bacteria; p_Firmicutes; c_Clostridia; o_Clostridiales; f_Ruminococcaceae; g_Oscillospira; s_ |
| 759751 | 1.863649835 | 0.041958042 | 43.19230769 | 17.125 | k_Bacteria; p_Firmicutes; c_Clostridia; o_Clostridiales; f_Lachnospiraceae; g_Dorea; s_ |
| New.CleanUp.ReferenceOTU77070 | 2.168565819 | 0.041958042 | 0.653846154 | 0.1875 | k_Bacteria; p_Bacteroidetes; c_Bacteroidia; o_Bacteroidales; f_Bacteroidaceae; g_Bacteroides; s_ |
| 4174963 | 2.083768333 | 0.043956044 | 2.307692308 | 0.875 | k_Bacteria; p_Bacteroidetes; c_Bacteroidia; o_Bacteroidales; f_Bacteroidaceae; g_Bacteroides; s_ |
| New.CleanUp.ReferenceOTU33851 | −2.345446101 | 0.043956044 | 0.115384615 | 0.5 | k_Bacteria; p_Bacteroidetes; c_Bacteroidia; o_Bacteroidales; f_Bacteroidaceae; g_Bacteroides; s_ovatus |
| 367215 | 2.128877321 | 0.044955045 | 6 | 2.625 | k_Bacteria; p_Firmicutes; c_Erysipelotrichi; o_Erysipelotrichales; f_Erysipelotrichaceae; g_Holdemania; s_ |
| 975306 | 1.868365208 | 0.044955045 | 3.615384615 | 1.125 | k_Bacteria; p_Firmicutes; c_Clostridia; o_Clostridiales; f_Lachnospiraceae; g_; s_ |
| 1928156 | 1.830574658 | 0.045954046 | 0.538461538 | 0.125 | k_Bacteria; p_Firmicutes; c_Clostridia; o_Clostridiales; f_Lachnospiraceae; g_Roseburia; s_ |
| 495396 | −2.024760012 | 0.045954046 | 0 | 0.3125 | k_Bacteria; p_Firmicutes; c_Clostridia; |

TABLE 2-continued

16S rRNA sequencing

| OTU | Test-Statistic | P value | NonResponder_mean | Responder_mean | taxonomy |
|---|---|---|---|---|---|
| 820346 | −1.654631254 | 0.046953047 | 4.692307692 | 72.125 | o_Clostridiales; f_[Tissierellaceae]; g_Anaerococcus; s_ |
| 360238 | −1.903434004 | 0.047952048 | 0.076923077 | 0.5625 | k_Bacteria; p_Proteobacteria; c_Gammaproteobacteria; o_Enterobacteriales; f_Enterobacteriaceae; g_; s_ |
| 1107027 | −1.830397468 | 0.048951049 | 0.884615385 | 8.75 | k_Bacteria; p_Firmicutes; c_Erysipelotrichi; o_Erysipelotrichales; f_Erysipelotrichaceae; g_; s_ |
| 528652 | 2.047565304 | 0.048951049 | 1.884615385 | 0.75 | k_Bacteria; p_Firmicutes; c_Bacilli; o_Lactobacillales; f_Lactobacillaceae; g_Lactobacillus; s_ruminis |
| 141145 | −2.039936818 | 0.04995005 | 1.730769231 | 5.125 | k_Bacteria; p_Firmicutes; c_Clostridia; o_Clostridiales; f_Ruminococcaceae; g_; s_ |
| 197537 | −1.994647776 | 0.04995005 | 0.346153846 | 0.9375 | k_Bacteria; p_Proteobacteria; c_Gammaproteobacteria; o_Enterobacteriales; f_Enterobacteriaceae; g_; s_ |
| 559527 | −1.651499936 | 0.057942058 | 20.80769231 | 84.6875 | k_Bacteria; p_Bacteroidetes; c_Bacteroidia; o_Bacteroidales; f_Bacteroidaceae; g_Bacteroides; s_ |
|  |  |  |  |  | k_Bacteria; p_Actinobacteria; c_Actinobacteria; o_Bifidobacteriales; f_Bifidobacteriaceae; g_Bifidobacterium; s_ |

TABLE 3A

16S rRNA data

| Family 16S | Species 16S | Direction of change | Non-parametric T test statistic | Non-parametric T test P value |
|---|---|---|---|---|
| Enterobacteriaceae | NA | UP in R | −3.274534 | 0.001998 |
| Enterobacteriaceae | NA | UP in R | −3.115289 | 0.005994 |
| Coriobacteriaceae | NA | UP in R | −2.958595 | 0.006993 |
| Lachnospiraceae | NA | UP in R | −2.872972 | 0.015984 |
| Ruminococcaceae | NA | UP in R | −2.863148 | 0.005994 |
| Enterobacteriaceae | NA | UP in R | −2.681220 | 0.015984 |
| Prevotellaceae | NA | UP in R | −2.667488 | 0.016983 |
| Verrucomicrobiaceae | Akkermansia_muciniphila | UP in R | −2.659855 | 0.015984 |
| Enterobacteriaceae | NA | UP in R | −2.659855 | 0.019980 |
| Lachnospiraceae | NA | UP in R | −2.585685 | 0.024975 |
| Enterobacteriaceae | NA | UP in R | −2.544080 | 0.015984 |
| NA | NA | UP in R | −2.480422 | 0.019980 |
| Ruminococcaceae | NA | UP in R | −2.464382 | 0.013986 |
| Bifidobacteriaceae | NA | UP in R | −2.424212 | 0.007992 |
| Lachnospiraceae | NA | UP in R | −2.399268 | 0.012987 |
| Porphyromonadaceae | Parabacteroides_distasonis | UP in R | −2.370320 | 0.020979 |
| Bacteroidaceae | Bacteroides_ovatus | UP in R | −2.345446 | 0.043956 |

TABLE 3A-continued

16S rRNA data

| Family 16S | Species 16S | Direction of change | Non-parametric T test statistic | Non-parametric T test P value |
|---|---|---|---|---|
| Bacteroidaceae | NA | UP in R | −2.236097 | 0.011988 |
| Porphyromonadaceae | NA | UP in R | −2.219337 | 0.021978 |
| Enterobacteriaceae | NA | UP in R | −2.189499 | 0.021978 |
| Enterobacteriaceae | NA | UP in R | −2.143055 | 0.031968 |
| Ruminococcaceae | NA | UP in R | −2.046964 | 0.014985 |
| Enterobacteriaceae | NA | UP in R | −2.039937 | 0.049950 |
| Lachnospiraceae | NA | UP in R | −2.031498 | 0.017982 |
| Lachnospiraceae | NA | UP in R | −2.029899 | 0.010989 |
| Tissierellaceae | NA | UP in R | −2.024760 | 0.045954 |
| Bacteroidaceae | NA | UP in R | −1.994648 | 0.049950 |
| Erysipelotrichaceae | NA | UP in R | −1.903434 | 0.047952 |
| Ruminococcaceae | NA | UP in R | −1.885076 | 0.041958 |
| Lachnospiraceae | NA | UP in R | −1.841788 | 0.038961 |
| Coriobacteriaceae | Collinsella_aerofaciens | UP in R | −1.839972 | 0.003996 |
| NA | NA | UP in R | −1.836191 | 0.032967 |
| Lactobacillaceae | Lactobacillus_ruminis | UP in R | −1.830397 | 0.048951 |
| Enterobacteriaceae | NA | UP in R | −1.755182 | 0.024975 |
| Coriobacteriaceae | Collinsella_aerofaciens | UP in R | −1.719135 | 0.006993 |
| Enterobacteriaceae | NA | UP in R | −1.654631 | 0.046953 |
| Bifidobacteriaceae | NA | UP in R | −1.651500 | 0.057942 |
| Enterococcaceae | NA | UP in R | −1.591732 | 0.000999 |
| Veillonellaceae | Veillonella_dispar | UP in R | −1.440777 | 0.019980 |
| Clostridiaceae | NA | UP in R | −1.321912 | 0.024975 |
| Lachnospiraceae | NA | UP in NR | 1.830575 | 0.045954 |
| Lachnospiraceae | NA | UP in NR | 1.863650 | 0.041958 |
| Lachnospiraceae | NA | UP in NR | 1.868365 | 0.044955 |
| Bacteroidaceae | NA | UP in NR | 2.043972 | 0.041958 |
| Ruminococcaceae | NA | UP in NR | 2.047565 | 0.048951 |
| Bacteroidaceae | NA | UP in NR | 2.065376 | 0.029970 |
| Lachnospiraceae | NA | UP in NR | 2.083409 | 0.034965 |
| Bacteroidaceae | NA | UP in NR | 2.083768 | 0.043956 |
| Erysipelotrichaceae | NA | UP in NR | 2.128877 | 0.044955 |
| Lachnospiraceae | NA | UP in NR | 2.136989 | 0.041958 |
| Bacteroidaceae | NA | UP in NR | 2.168566 | 0.041958 |
| Lachnospiraceae | NA | UP in NR | 2.172568 | 0.034965 |
| Erysipelotrichaceae | NA | UP in NR | 2.223328 | 0.035964 |
| NA | NA | UP in NR | 2.384249 | 0.027972 |
| Odoribacteraceae | NA | UP in NR | 2.394752 | 0.032967 |
| Ruminococcaceae | NA | UP in NR | 2.396655 | 0.034965 |
| S24-7 | NA | UP in NR | 2.407682 | 0.022977 |
| Lachnospiraceae | NA | UP in NR | 2.414385 | 0.011988 |
| Lachnospiraceae | NA | UP in NR | 2.416382 | 0.019980 |
| NA | NA | UP in NR | 2.533904 | 0.011988 |
| Lachnospiraceae | NA | UP in NR | 2.602400 | 0.013986 |
| Desulfovibrionaceae | NA | UP in NR | 2.903506 | 0.007992 |
| Bacteroidaceae | NA | UP in NR | 3.071336 | 0.009990 |

TABLE 3B

Shotgun sequencing data.

| Species shotgun | Spearman correlation rho | Spearman correlation P value | Confirmed by shotgun sequencing | BLAST agreement | Inclusion in the SVM model training and validation |
|---|---|---|---|---|---|
| Escherichia_coli | 0.550530 | 0.000282 | Yes | Yes | Removed |
| Escherichia_coli | 0.629962 | 0.000017 | Yes | No | Yes |
| Atopobium_parvulum | 0.576876 | 0.000121 | Yes | Yes | Removed |
| Dorea_formicigenerans | 0.334512 | 0.037394 | Yes | No | Yes |
| Faecalibacterium_prausnitzii | 0.414561 | 0.008692 | Yes | Yes | Removed |
| Klebsiella_pneumoniae | 0.533469 | 0.000470 | Yes | Yes | Yes |
| NA | NA | NA | NE | Yes | Yes |
| Akkermansia_muciniphila | 0.410041 | 0.009528 | Yes | Yes | Yes |
| Klebsiella_oxytoca | 0.413549 | 0.008873 | Yes | Yes | Removed |
| Anaerostipes_caccae | 0.311151 | 0.053845 | NE | Yes | Removed |
| Escherichia_coli | 0.646825 | 0.000009 | Yes | Yes | Removed |

TABLE 3B-continued

Shotgun sequencing data.

| Species shotgun | Spearman correlation rho | Spearman correlation P value | Confirmed by shotgun sequencing | BLAST agreement | Inclusion in the SVM model training and validation |
|---|---|---|---|---|---|
| NA | NA | NA | NE | NA | Yes |
| Faecalibacterium_prausnitzii | 0.362051 | 0.023519 | Yes | NA | Yes |
| Bifidobacterium_adolescentis | 0.566864 | 0.000168 | Yes | No | Yes |
| Lachnospiraceae_bacterium_6_1_63FAA | 0.536065 | 0.000436 | Yes | Yes | Removed |
| Parabacteroides_distasonis | 0.398512 | 0.011978 | Yes | No | Yes |
| Bacteroides_eggerthii | 0.301822 | 0.061851 | NE | No | Removed |
| Bacteroides_xylanisolvens | 0.270799 | 0.095427 | NE | NA | Yes |
| Parabacteroides_merdae | 0.899720 | 6.86E-15 | Yes | No | Yes |
| Escherichia_coli | 0.644850 | 0.000009 | Yes | No | Removed |
| Escherichia_unclassified | 0.496450 | 0.001307 | Yes | NA | Yes |
| Anaerotruncus_unclassified | 0.420373 | 0.007710 | Yes | No | Yes |
| Escherichia_coli | 0.755701 | 2.68E-08 | Yes | Yes | Removed |
| Lachnospiraceae_bacterium_8_1_57FAA | 0.250059 | 0.124705 | NE | Yes | Yes |
| Lachnospiraceae_bacterium_9_1_43BFAA | 0.455202 | 0.003594 | Yes | Yes | Yes |
| NA | NA | NA | NE | Yes | Removed |
| Bacteroides_ovatus | 0.279476 | 0.084877 | NE | Yes | Yes |
| Solobacterium_moorei | 0.311151 | 0.053845 | NE | Yes | Yes |
| Ruminococcus_callidus | 0.498926 | 0.001225 | Yes | Yes | Removed |
| Lachnospiraceae_bacterium_6_1_63FAA | 0.493379 | 0.001420 | Yes | Yes | Removed |
| Collinsella_aerofaciens | 0.909381 | 1.15E-15 | Yes | Yes | Removed |
| NA | NA | NA | NE | No | Yes |
| Lactobacillus_animalis | 0.269342 | 0.097300 | NE | Yes | Yes |
| Klebsiella_pneumoniae | 0.681088 | 0.000002 | Yes | No | Removed |
| Collinsella_aerofaciens | 0.884610 | 8.07E-14 | Yes | Yes | Yes |
| Klebsiella_pneumoniae | 0.776955 | 6.05E-09 | Yes | Yes | Yes |
| Bifidobacterium_longum | 0.827885 | 7.96E-11 | Yes | Yes | Yes |
| Enterococcus_faecium | 0.540876 | 0.000378 | Yes | Yes | Yes |
| Veillonella_parvula | 0.466233 | 0.002780 | Yes | Yes | Yes |
| Clostridium_perfringens | 0.153504 | 0.351000 | NE | No | Removed |
| Roseburia_intestinalis | 0.541337 | 0.000373 | Yes | No | Yes |
| Dorea_unclassified | 0.483302 | 0.001830 | Yes | Yes | Yes |
| Ruminococcus_obeum | 0.452795 | 0.003799 | Yes | Yes | Yes |
| NA | NA | NA | NE | NA | Yes |
| Faecalibacterium_prausnitzii | 0.419746 | 0.007811 | Yes | No | Yes |
| Bacteroides_thetaiotaomicron | 0.485656 | 0.001720 | Yes | NA | Yes |
| Marvinbryantia_formatexigens | 0.325481 | 0.043184 | Yes | NA | Yes |
| Bacteroides_vulgatus | 0.492837 | 0.001435 | Yes | Yes | Yes |
| Holdemania_filiformis | 0.684482 | 0.000002 | Yes | NA | Yes |
| Dorea_longicatena | 0.558706 | 0.000218 | Yes | Yes | Yes |
| Bacteroides_finegoldii | 0.281691 | 0.082334 | NE | NA | Removed |
| Ruminococcus_obeum | 0.510578 | 0.000897 | Yes | No | Removed |
| Holdemania_unclassified | 0.151990 | 0.355654 | NE | No | Removed |
| NA | NA | NA | NE | NA | Yes |
| NA | NA | NA | NE | Yes | Removed |
| Ruminococcus_sp_5_1_39BFAA | 0.338589 | 0.034995 | Yes | NA | Yes |
| NA | NA | NA | NE | Yes | Yes |
| Lachnospiraceae_bacterium_9_1_43BFAA | 0.378586 | 0.017475 | Yes | Yes | Yes |
| Lachnospiraceae_bacterium_5_1_63FAA | 0.680934 | 0.000002 | Yes | No | Yes |
| NA | NA | NA | NE | No | Yes |
| Roseburia_inulinivorans | 0.432282 | 0.005991 | Yes | Yes | Yes |
| NA | NA | NA | NE | No | Yes |
| Bacteroides_salyersiae | 0.355278 | 0.026453 | Yes | No | Removed |

TABLE 4A qPCR data

| Sample Name | R/NR | Up in R V. parvula | Up in R E. faecium | Up in R C. aerofaciens | Up in R B. adolescentis | Up in R B. longum | Up in R K. pneumoniae | Up in R L. ruminis subgroup | Up in R P. merdae | Up in NR R. intestinalis | Up in NR R. obeum |
|---|---|---|---|---|---|---|---|---|---|---|---|
| P01 | NR | 11,475 | 0 | 62,725 | 0 | 0 | 0 | 0 | 1,597,873 | 13 | 0 |
| P02 | R | 24,078 | 0 | 22,452 | 0 | 0 | 0 | 5.513956 | 97,020 | 516 | 482 |
| P03 | NR | 36 | 168 | 16 | 0 | 15,995 | 0 | 0 | 260,671 | 45,708 | 0 |
| P04 | NR | 2,433 | 0 | 0 | 8,003 | 102,209 | 0 | 0 | 42,860 | 3,849 | 9,634 |
| P05 | NR | 15 | 0 | 0 | 10,480 | 82,559 | 0 | 132.1112 | 0 | 13,676 | 9,072 |
| P06 | NR | 0 | 0 | 0 | 0 | 111 | 0 | 0 | 319 | 2,141 | 29,679 |

TABLE 4A-continued qPCR data

| Sample Name | R/NR | Up in R V. parvula | Up in R E. faecium | Up in R C. aerofaciens | Up in R B. adolescentis | Up in R B. longum | Up in R K. pneumoniae | Up in R L. ruminis subgroup | Up in R P. merdae | Up in NR R. intestinalis | Up in NR R. obeum |
|---|---|---|---|---|---|---|---|---|---|---|---|
| P07 | R | 1,779 | 0 | 0 | 0 | 0 | 0 | 0 | 316,456 | 2,539 | 5,416 |
| P08 | NR | 4,103 | 0 | 11,231 | 16 | 43,243 | 0 | 0 | 0 | 10,940 | 20,678 |
| P09 | NR | 945 | 0 | 0 | 0 | 0 | 0 | 78.39282 | 346,039 | 9 | 0 |
| P10 | NR | 543 | 0 | 10,150 | 0 | 0 | 0 | 0 | 15 | 23 | 2,797 |
| P11 | NR | 0 | 0 | 0 | 0 | 193 | 0 | 0 | 0 | 54,846 | 860 |
| P12 | NR | 177 | 0 | 44,697 | 0 | 0 | 5,184 | 0 | 0 | 11,575 | 2,836 |
| P13 | R | 0 | 0 | 0 | 0 | 0 | ND | 0 | 0 | 0 | ND |
| P14 | NR | 5,340 | 0 | 16,232 | 0 | 11,295 | 0 | 0 | 50,976 | 1,170 | 2,850 |
| P15 | NR | 119 | 0 | 0 | 0 | 88,445 | 0 | 34.14117 | 39 | 28 | 0 |
| P16 | R | 1,587 | 133,010 | 246,723 | 145,416 | 9,352 | 435 | 120019 | 0 | 2,647 | 925 |
| P17 | NR | 0 | 0 | 64,284 | 0 | 164,311 | 0 | 0 | 67,195 | 1,441 | 0 |
| P18 | NR | 71 | 0 | 4,493 | 0 | 0 | 0 | 0 | 126,522 | 29 | 11 |
| P19 | NR | 576 | 0 | 9,559 | 4,611 | 909 | 4 | 0 | 175,857 | 8 | 0 |
| P20 | R | 212 | 10,831 | 2,967,175 | 128,639 | 3,901,078 | 0 | 46600.89 | 17,967 | 1,581 | 0 |
| P21 | NR | 55 | 0 | 39,673 | 28,122 | 12,003 | 0 | 0 | 0 | 3,341 | 5,039 |
| P22 | NR | 209 | 0 | 0 | 0 | 42 | 0 | 58.23432 | 0 | 19 | 8,365 |
| P23 | R | 6 | 0 | 477,784 | 33,745 | 243,696 | 0 | 0 | 43,826 | 2,597 | 6,693 |
| P24 | R | 95 | 648 | 7 | 0 | 59,624 | 0 | 0 | 99,812 | 164 | 22,048 |
| P25 | NR | 0 | 0 | 62,221 | 0 | 80 | 0 | 8.494507 | 440,357 | 18,236 | 15,102 |
| P26 | NR | 914 | 0 | 64,251 | 15,483 | 37,583 | 0 | 9.874153 | 142,228 | 184 | 6,696 |
| P27 | R | 1,737 | 820 | 0 | 0 | 218,452 | 0 | 0 | 330,927 | 266 | 2,965 |
| P28 | R | 17,842 | 0 | 103,390 | 5 | 92,534 | 2,532 | 38943.37 | 64,752 | 3,582 | 5 |
| P29 | R | 8,259 | 0 | 0 | 0 | 23 | 0 | 0 | 686,549 | 62,125 | 11,876 |
| P30 | NR | 64 | 139 | 2,530 | ND | 2,788 | ND | ND | 0 | 1,253 | 14,685 |
| P31 | NR | 36 | 0 | 0 | 0 | 0 | 0 | 0 | 869,370 | 1,066 | 22,889 |
| P32 | NR | 272 | 0 | 45,490 | 0 | 46 | 0 | 0 | 1,247,815 | 19,038 | 8,921 |
| P33 | R | 3,458 | 0 | 0 | 0 | 0 | 0 | 0 | 0 | 258 | 959 |
| P34 | R | 512 | 121 | 43,590 | 1,419 | 64,464 | 0 | 8.103439 | 89,046 | 63 | 2,981 |
| P35 | NR | 58 | 0 | 79,197 | 0 | 0 | 19 | 0 | 442,665 | 61 | 10,102 |
| P36 | R | 265 | 0 | 6,651 | 5,618 | 12,852 | 0 | 0 | 384,166 | 22 | 571 |
| P37 | R | 300 | 0 | 0 | 0 | 2,794 | 638 | 0 | 67,680 | 5 | 2,590 |
| P38 | NR | 74 | 0 | 6,556 | 0 | 0 | 0 | 0 | 402,480 | 904 | 0 |
| P39 | R | 0 | 0 | 423,770 | 0 | 265 | 0 | 0 | 17,056 | 53 | 0 |
| P40 | NR | 8,479 | 0 | 91,856 | 0 | 21,494 | 278 | 8.091473 | 53,714 | 3,553 | 5,657 |
| P41 | R | 2,425 | 2,501 | 25,124 | 0 | 11,689 | 58,503 | 0 | 61,827 | 984 | 1,441 |
| P42 | NR | 1,036 | 0 | 0 | 0 | 115,017 | 0 | 718.3709 | 1,012 | 11,668 | 17,655 |

TABLE 4B qPCR primers

| Target species | Primer sequence (5'->3') | SEQ ID NO: | SYBR/TaqMan | Annealing | Extension and fluorescence detection |
|---|---|---|---|---|---|
| Akkermansia muciniphila | Forward: CAGCACGTGAAGGTGGGGAC | 1 | SYBR | 60° C./40 s | 72° C./30 s |
| | Reverse: CCTTGCGGTTGGCTTCAGAT | 2 | | | |
| Bacteroides vulgatus | Forward: AAGGGAGCGTAGATGGATGTTTA | 3 | TaqMan | 65° C./60 s | |
| | Reverse: CGAGCCTCAATGTCAGTTGC | 4 | | | |
| | Probe (FAM/TAMRA): CCTGCCTCAACTGCACTCAAGATATCCAGTA | 5 | | | |
| Bifidobacterium adolescentis | Forward: CTCCGCCGCTGATCCGGAAGTCG | 6 | SYBR | 75° C./15 s | 72° C./15 s |
| | Reverse: AACCAACTCGGCGATGTGGACGACA | 7 | | | 83° C./15 s |
| Bifidobacterium longum | Forward: TTCCAGTTGATCGCATGGTC | 8 | SYBR | 60° C./30 s | 85° C./60 s |
| | Reverse: TC(G/C)CGCTTGCTCCCCGAT | 9 | | | |
| Collinsella aerofaciens | Forward: CCCGACGGGAGGGGAT | 10 | SYBR | 60° C./40 s | 72° C./30 s |
| | Reverse: CTTCTGCAGGTACAGTCTTGA | 11 | | | |
| Enterococcus faecium | Forward: CGAGAAGAGCTGCAAAATGCTTTAGC *** | 12 | SYBR | 60° C./40 s | 72° C./30 s |
| | Reverse: GCGCGCTTCAATTCCTTGT | 13 | | | |
| Faecalibacetrium prausnitzii | Forward: CCCTTCAGTGCCGCAGT | 14 | SYBR | 61° C./40 s | 72° C./30 s |
| | Reverse: GTCGCAGGATGTCAAGAC | 15 | | | |
| Klebsiella pneumoniae | Forward: GCG TGG CGG TAG ATC TAA GTC ATA | 16 | SYBR | 58° C./10 s | 72° C./40 s |
| | Reverse: TTC AGC TCC GCC ACA AAG GTA | 17 | | | |
| Lactobacillus ruminis subgroup ** | Forward: CACCGAATGCTTGCAYTCACC | 18 | SYBR | 60° C./20 s | 72° C./50 s |
| | Reverse: GCCGCGGGTCCATCCAAAA | 19 | | | |
| Parabacteroides distasonis | Forward: TGCCTATCAGAGGGGGATAAC | 20 | TaqMan | 60° C./60 s | |
| | Reverse: GCAAATATTCCCATGCGGGAT | 21 | | | |
| | Probe (FAM/TAMRA): CGAAAGTCGGACTAATACCGCATGAAGC | 22 | | | |

TABLE 4B-continued qPCR primers

| Target species | Primer sequence (5'->3') | SEQ ID NO: | SYBR/TaqMan | Annealing | Extension and fluorescence detection |
|---|---|---|---|---|---|
| Parabacteroides merdae | Forward: AGGGTGCGTAGGTGGTGAT | 23 | TaqMan | 65/60 s | |
| | Reverse: TTCACCGCTACACCACGC | 24 | | | |
| | Probe (FAM/TAMRA): TTACTTGAGTGTGTTTGAGGTAGGCGG | 25 | | | |
| Roseburia intestinalis | Forward: TTCGCAGCTCAGTCTATCGC *** | 26 | SYBR | 55° C./30 s | 72° C./30 s |
| | Reverse: GCAATCCCCGGGAAGTCATT *** | 27 | | | |
| Ruminococcus obeum | Forward: GCAGATTTGGTCTGTTTC | 28 | TaqMan | 60° C./60 s | |
| | Reverse: CGGTATTAGCAACCATTTC | 29 | | | |
| | Probe (FAM/TAMRA): CTGTATAAGGCAGGTTACCCACGC | 30 | | | |
| Veillonella spp.* | Forward: A(C/T)CAACCTGCCCTTCAGA | 31 | SYBR | 60° C./40 s | 72° C./30 s |
| | Reverse: CGTCCCGATTAACAGAGCTT | 32 | | | |
| Universal bacterial primers | Forward: AGAGTTTGATCCTGGCTCAG | 33 | SYBR | 52° C./30 s | 72° C./60 s |
| | Reverse: TGCTGCCTCCCGTAGGAG | 34 | | | |

*Target species include V. parvula, V. dispar, V. atypica, V. ratti, V. criceti, V. rodentium, V. caviae
** This subgroup was specified based on similaritie in 16S rRNA gene sequence in the cited study. The primers amplify L. ruminis, L. animalis, L. mali, L. salivarius, L. satsumensis, L. graminis, L. panis
*** The sequence of this primer was modified from the originally reported sequence

TABLE 5

Metagenomic sequencing.

| Species shotgun | Direction of change | Non-parametric T test statistic | Non-parametric T test P value | Overlap with the 63 16S OTUs |
|---|---|---|---|---|
| Enterococcus_faecalis | Up in R | −2.392458368 | 0.014985015 | . |
| Escherichia_coli | Up in R | −2.210901572 | 0.016983017 | Yes |
| Escherichia_unclassified | Up in R | −2.14017738 | 0.032967033 | Yes |
| Bacteroides_ovatus | Up in R | −2.005216423 | 0.043956044 | NE |
| Turicibacter_sanguinis | Up in R | −1.857270068 | 0.033966034 | . |
| Collinsella_aerofaciens | Up in R | −1.833005718 | 0.017982018 | Yes |
| Clostridium_scindens | Up in R | −1.811319782 | 0.076923077 | . |
| Clostridium_nexile | Up in R | −1.801806225 | 0.007992008 | . |
| Actinomyces_graevenitzii | Up in R | −1.741014848 | 0.091908092 | . |
| Eubacterium_siraeum | Up in R | −1.729111828 | 0.091908092 | . |
| Lachnospiraceae_bacterium_7_1_58FAA | Up in R | −1.716806138 | 0.095904096 | . |
| Bifidobacterium_longum | Up in R | −1.701918723 | 0.023976024 | Yes |
| Haemophilus_parainfluenzae | Up in R | −1.669086484 | 0.071928072 | . |
| Veillonella_parvula | Up in R | −1.502989879 | 0.011988012 | Yes |
| Lachnospiraceae_bacterium_6_1_63FAA | Up in R | −1.42054428 | 0.084915085 | Yes |
| Klebsiella_oxytoca | Up in R | −1.401188635 | 0.046953047 | Yes |
| Enterococcus_faecium | Up in R | −1.378987414 | 0.000999001 | Yes |
| Campylobacter_gracilis | Up in R | −1.330045919 | 0.043956044 | . |
| Burkholderiales_bacterium_1_1_47 | Up in NR | 1.831387273 | 0.051948052 | . |
| Bacteroides_intestinalis | Up in NR | 1.864425356 | 0.064935065 | . |
| Adlercreutzia_equolifaciens | Up in NR | 1.93586273 | 0.062937063 | . |
| Holdemania_filiformis | Up in NR | 2.071359703 | 0.056943057 | Yes |
| Coprococcus_comes | Up in NR | 2.097221049 | 0.027972028 | . |

The 16S rRNA sequencing revealed 62 Operational Taxonomic Units (OTUs) of different abundance in R vs. NR (Table 2). Unsupervised hierarchical clustering based on abundance similarity of these OTUs revealed that most samples were accurately grouped according to clinical response (FIG. 2). Supervised clustering according to clinical outcome is depicted in FIG. 1A. Thirty-nine OTUs were more abundant in R and twenty-three were more abundant in NR. One Bifidobacteriaceae OTU was significantly more abundant in R and a second Bifidobacteriaceae OTU (559527) had borderline significance and was included in the analyses (total=63 OTUs). This observation recapitulates the previous results that associated Bifidobacteriaceae family members with improved immune-mediated tumor control and efficacy of anti-PD-L1 therapy in mice (Ref. 3B; herein incorporated by reference in its entirety).

Figure 1B:
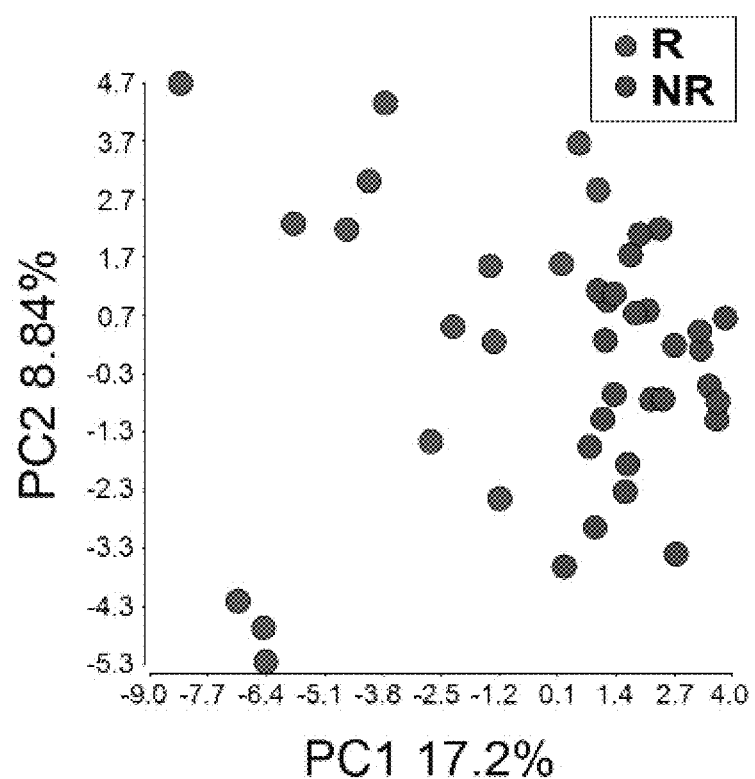
Figure 6A:
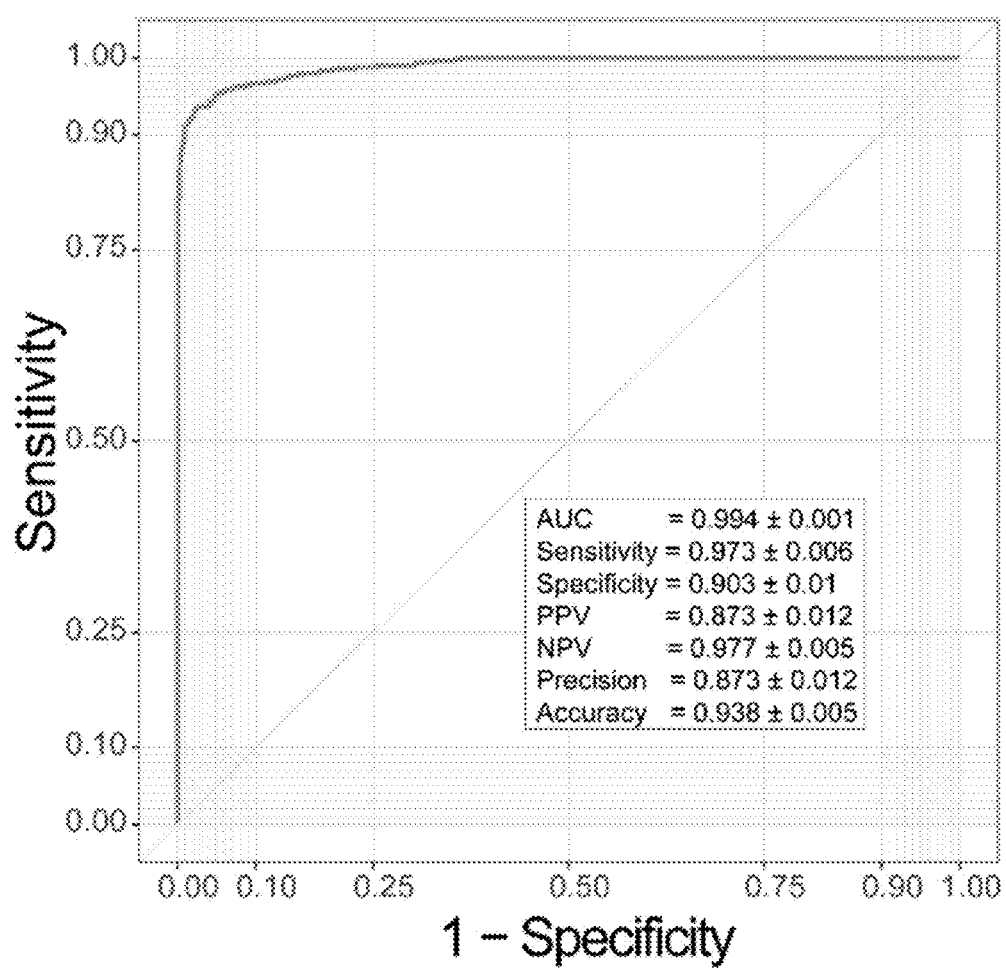
FIG. 6A-B. Performance assessment of the support vector machine (SVM) final models and relative variable importance of 42 OTU predictors. (A) Combined ROC curve produced by 100 iterative runs of model training and testing. The model performance metrics are shown as the Mean±SEM for area under curve (AUC), sensitivity, specificity, positive predictive value (PPV), negative predictive value (NPV), precision, and balanced accuracy. (B) Variable importance estimation of the predictors across 100 iterative runs. The upper panel represents a histogram of the mean variable importance of each predictor. The bottom panel shows the variable importance distribution, with each line representing one predictor, and vertical line representing the mean variable importance for each predictor. Different colors indicate different predictors.
Figure 6B:
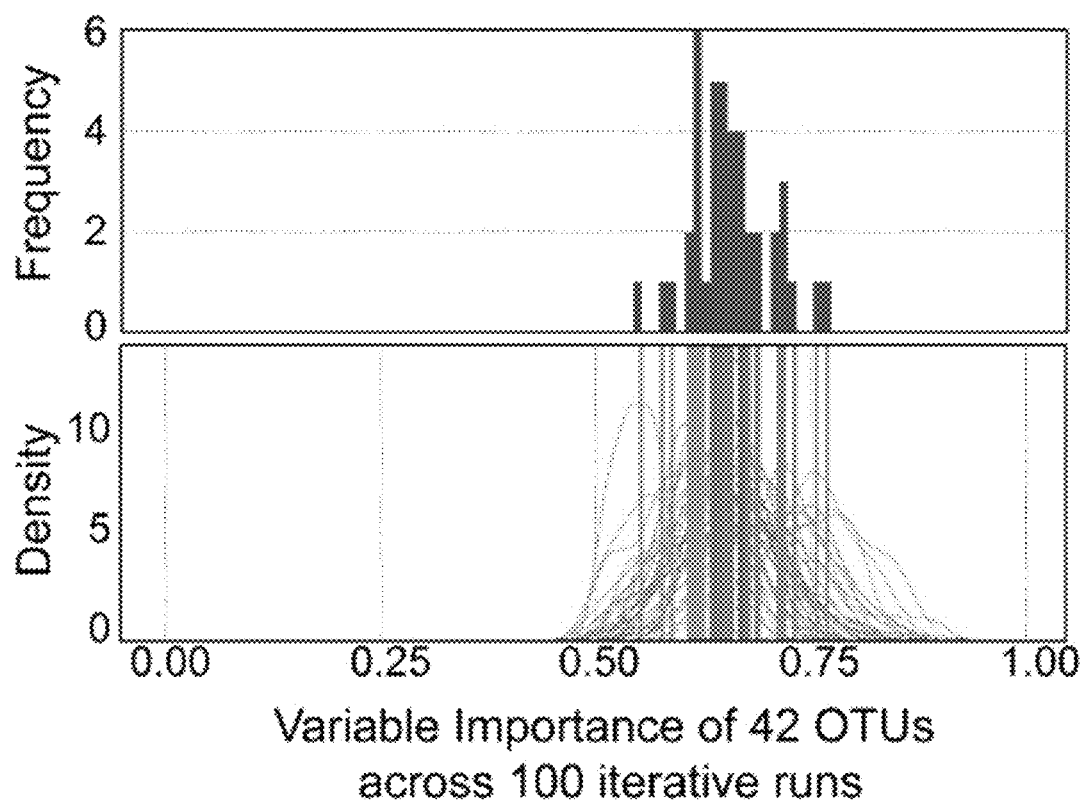
Figure 7A:
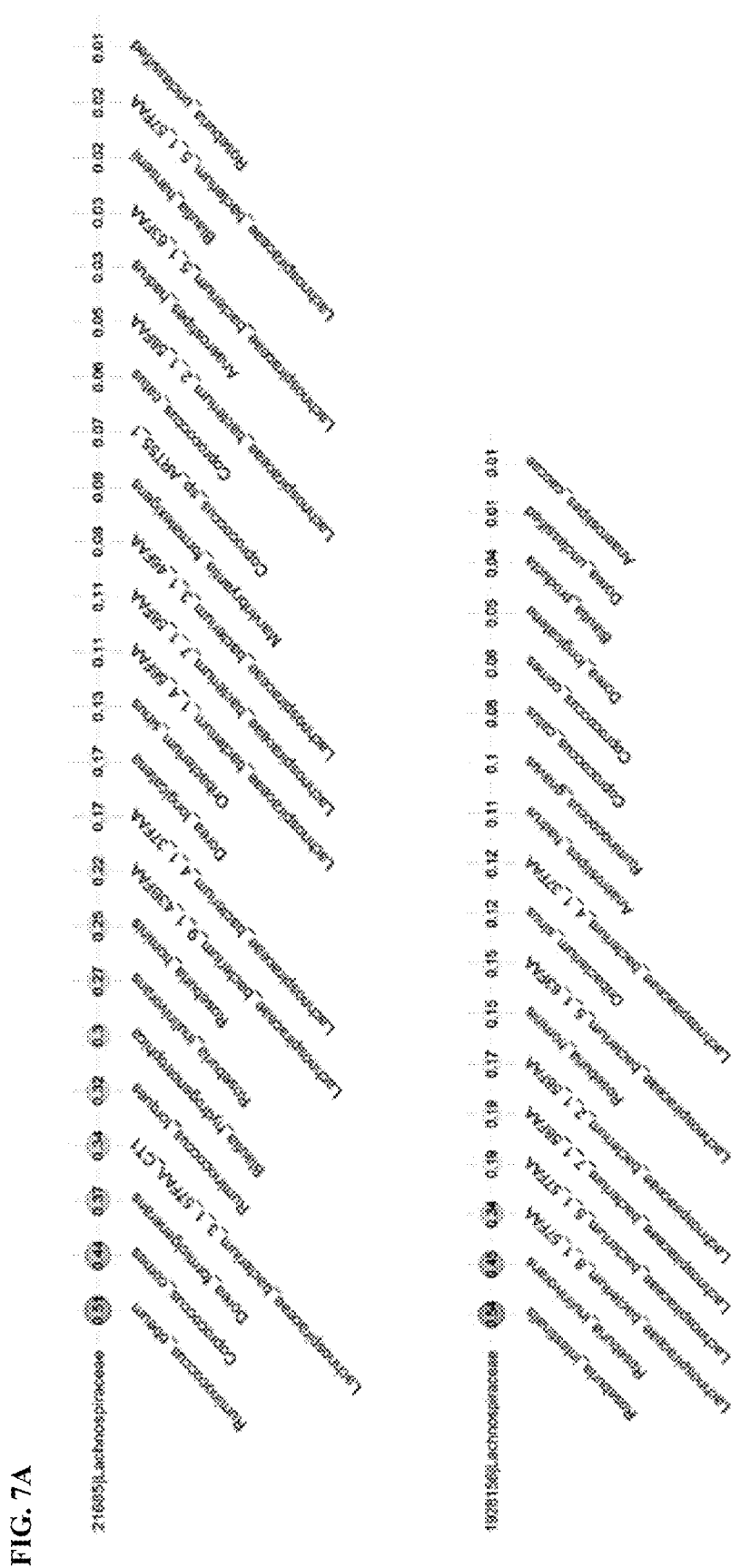
FIG. 7A-B. Ranked species-level identities of 16S OTUs predicted with shotgun sequencing. OTUs picked by 16S sequencing analysis were first matched to species identified by shotgun sequencing at the family level. Then, pairwise tie-corrected Spearman's correlation was computed for each matching pair and the species matched to each OTU were ranked based on the p value. A complete list of the 63 OTU-to-species matching between the 16S and shotgun sequencing datasets is included in Table S4.
Figure 7B:
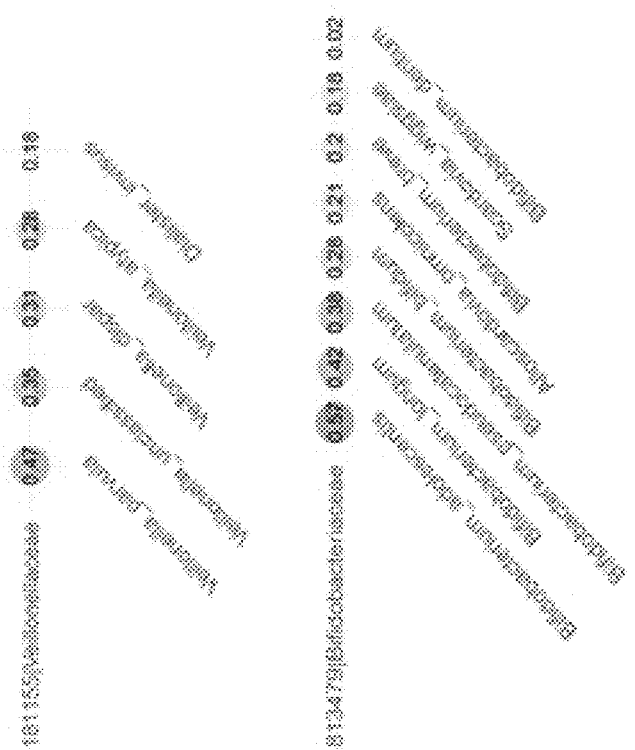
Figure 7B:
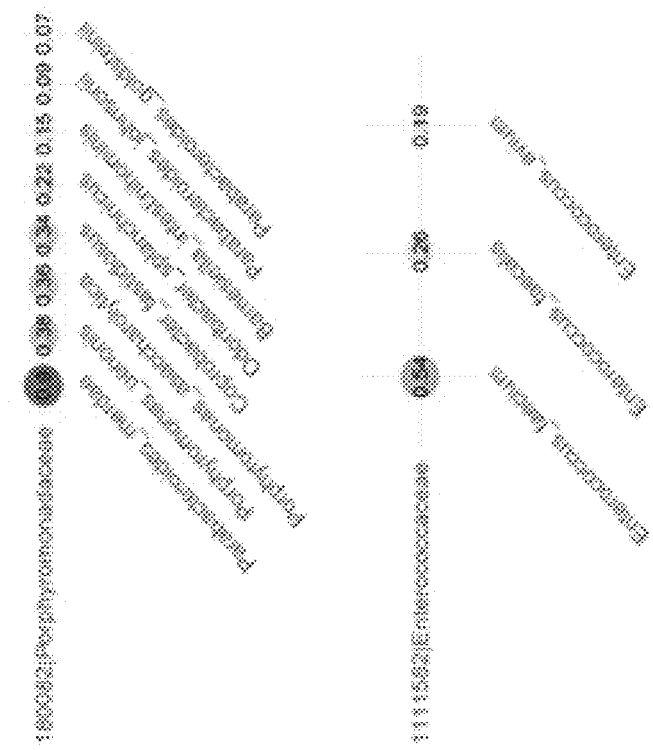
Figure 7B:

A principal component analysis (PCA) of the 63 OTUs revealed separation of R from NR (FIG. 1B). Predictive modeling was performed to assess the robustness of the data. The 63 OTUs (predictors) were evaluated to remove those of small variance, high correlation, and/or high collinearity, leaving 42 OTUs for the predictive modeling analysis (Table 3). Iterative modeling was performed by randomly splitting the samples into 60% as a training set model selection with 5-fold cross-validation, and 40% as a test set for independent assessment of model performance. A receiver-operator characteristic curve revealed an average of 87% positive and 98% negative predictive value for response as a function of 16S OTU predictors (FIG. 6A). A frequency plot of each of the 42 OTUs across these iterative runs revealed an overlapping range of importance of each of the features without any OTU dominating the model (FIG. 6B). These results indicate that stability of the data is not skewed based on disproportionate influence of a small number of elements.

Figure 2A:
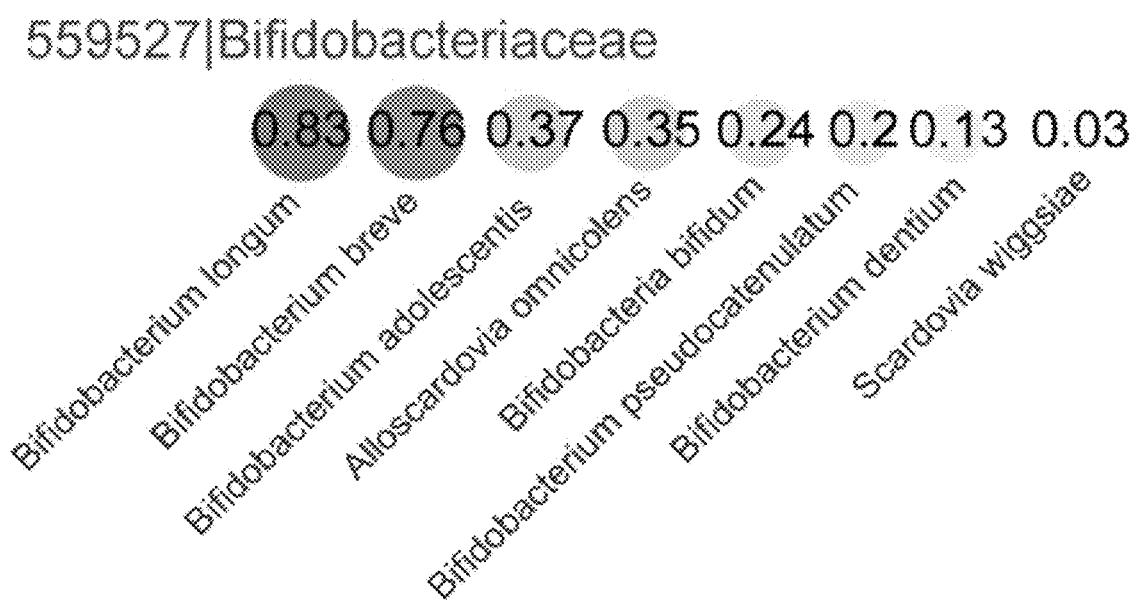
FIG. 2A-E. Integration of sequencing methods and qPCR for the identification of commensal bacterial species associated with clinical response to anti-PD-1 therapy. (A) Ranked Spearman's correlation coefficients between the relative abundances of Bifidobacteriaceae OTU 559527 from the 16S data set and species-level identities predicted by shotgun sequencing. The species profiled with shotgun sequencing were compared to the taxonomy of OTUs generated from 16S sequencing at family level. (B) Spearman's correlation between abundance of OTU 559527 from the 16S dataset and *B. longum* identified by metagenomics shotgun sequencing analysis (left) and qPCR (right). Shaded band indicates 95% CI of the values fitted by linear regression. (C) Relative abundance in responders (R) vs. non-responders (NR) of OTU 559527 (16S sequencing; left), *Bifidobacterium longum* (shotgun sequencing; middle), and *Bifidobacterium longum* (qPCR; right). (D) qPCR score representing an aggregate data for the relative abundances of 10 species correlated to OTUs with differential abundance in responders vs. non-responders. (E) Ratio of beneficial to non-beneficial OTU numbers for each patient vs. the patient's RECIST aggregate tumor measurement change. Dashed lines label RECIST %=−30 and ratio=1.5. Only the 43 16S OTUs confirmed by shotgun metagenomic sequencing were included.
Figure 2B:
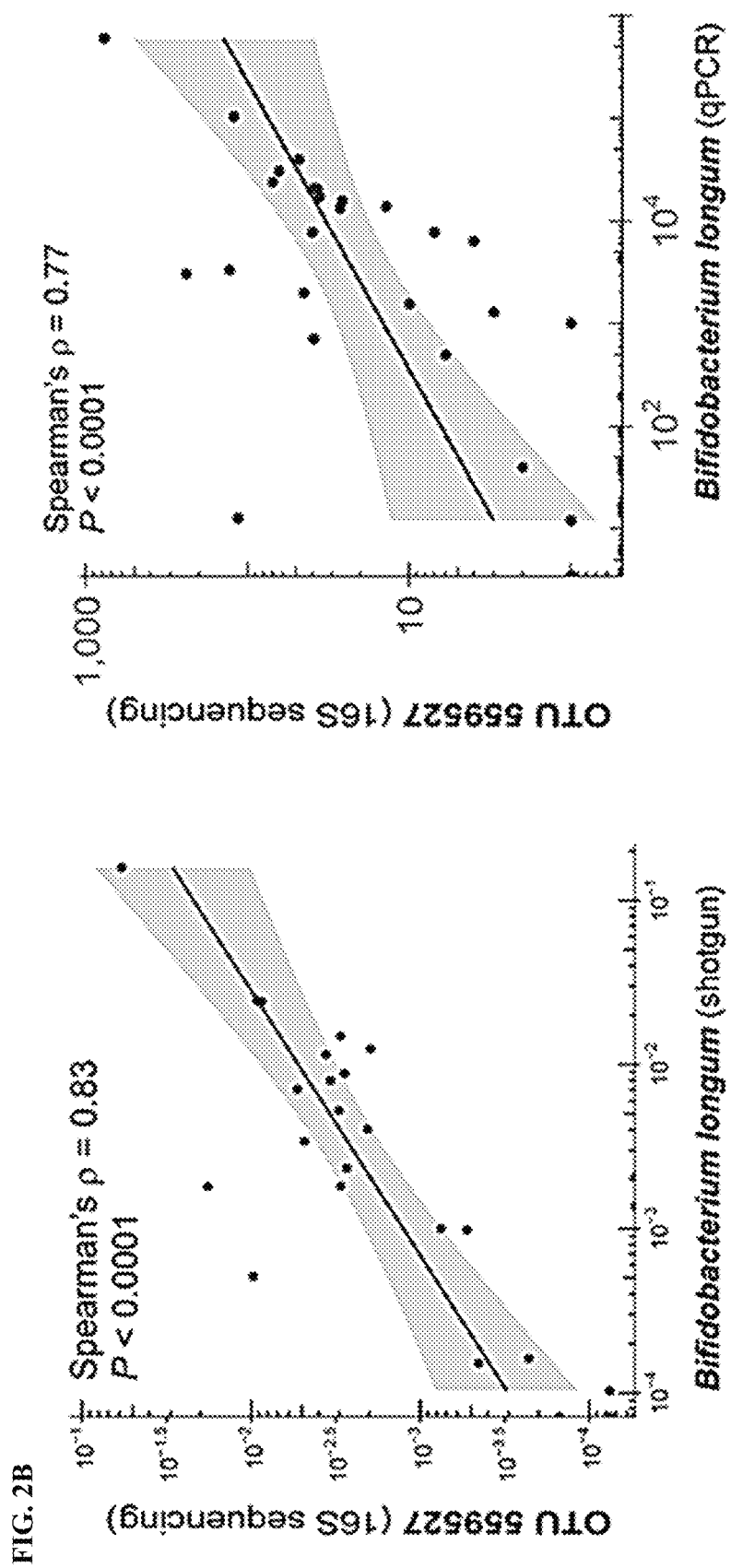
Figure 2C:
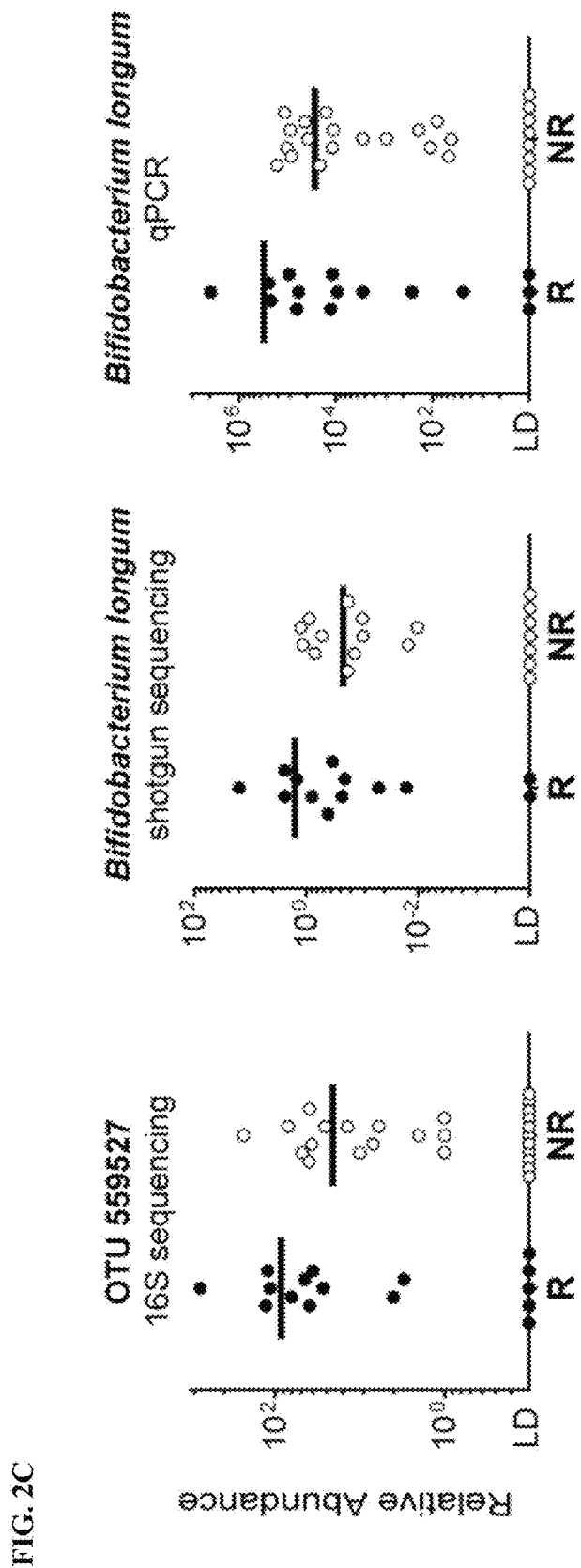
Figure 2E:
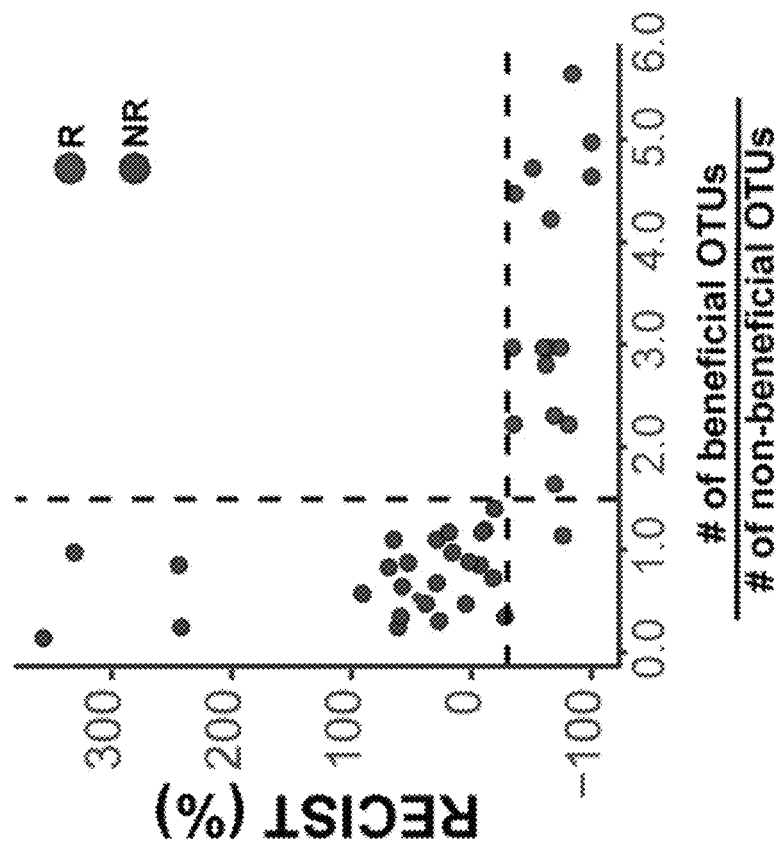
Figure 2D:
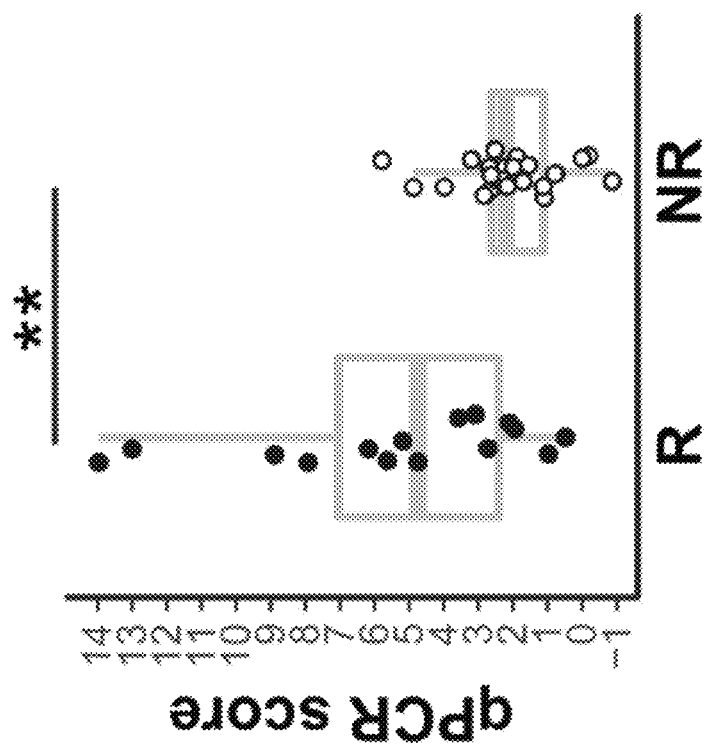
Figure 8:
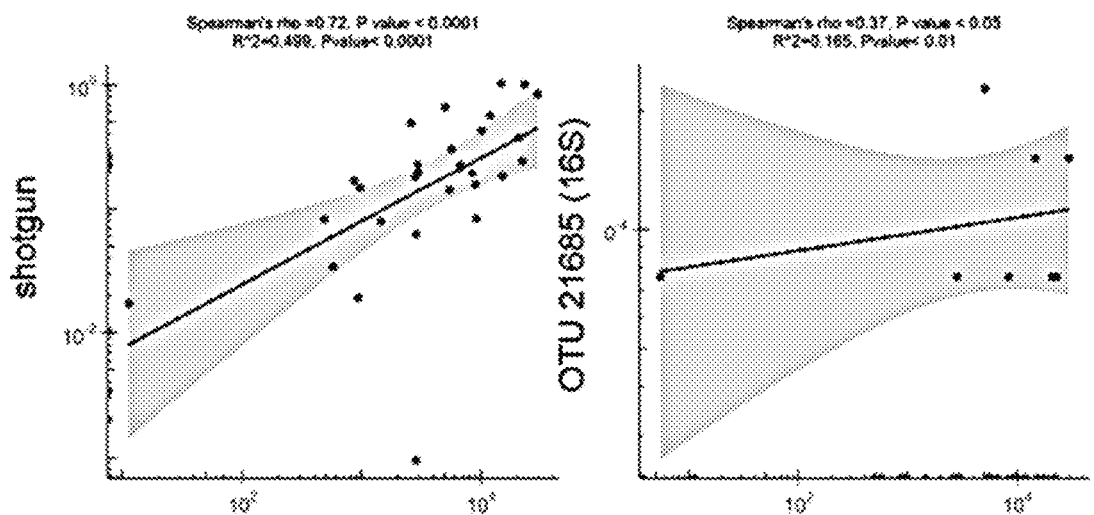
FIG. 8A-B. Use of species-specific qPCR for additional confirmation of the OTU-to-species matches determined by 16S and shotgun sequencing data comparisons. OTUs and their best-match species as measured with 16S and shotgun sequencing, respectively, were correlated by Spearman's test against the relative abundance of the corresponding species measured with qPCR. Depicted are correlations for OTUs (and their best-match species), which are more abundant in non-responders (A) or in responders (B) and are used for computation of the qPCR score. OTU 1107027 (identified as *Lactobacillus ruminis* with 16S sequencing analysis) was best matched to *Lactobacillus animalis* (from the shotgun sequencing data set) with P<0.1 (Table 3B) and was included in the qPCR score, because a primer set with a broader *Lactobacillus* sp. specificity was used (Table 4A-B).
Figure 8:
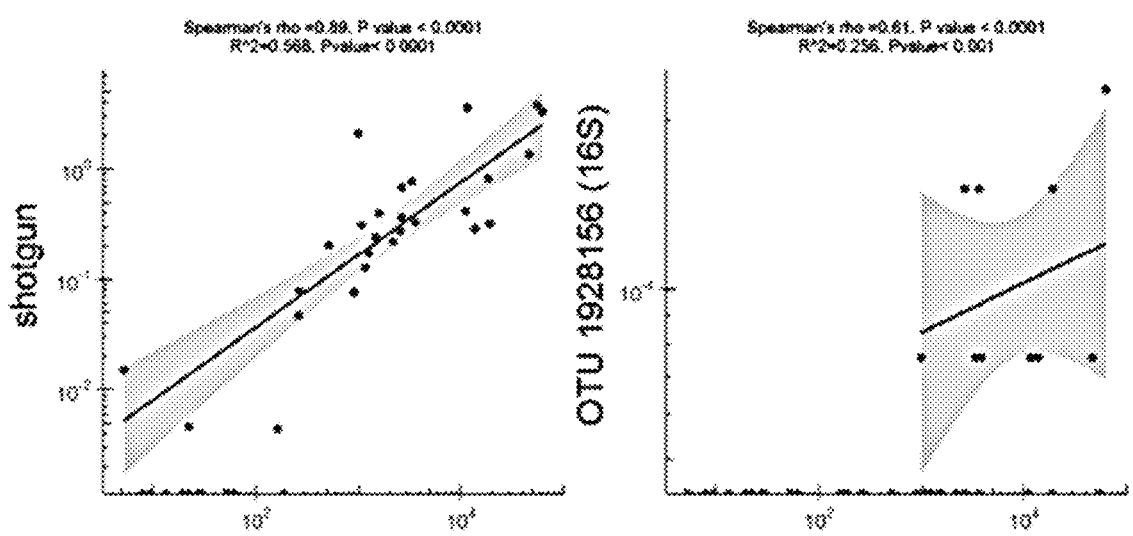
Figure 8:
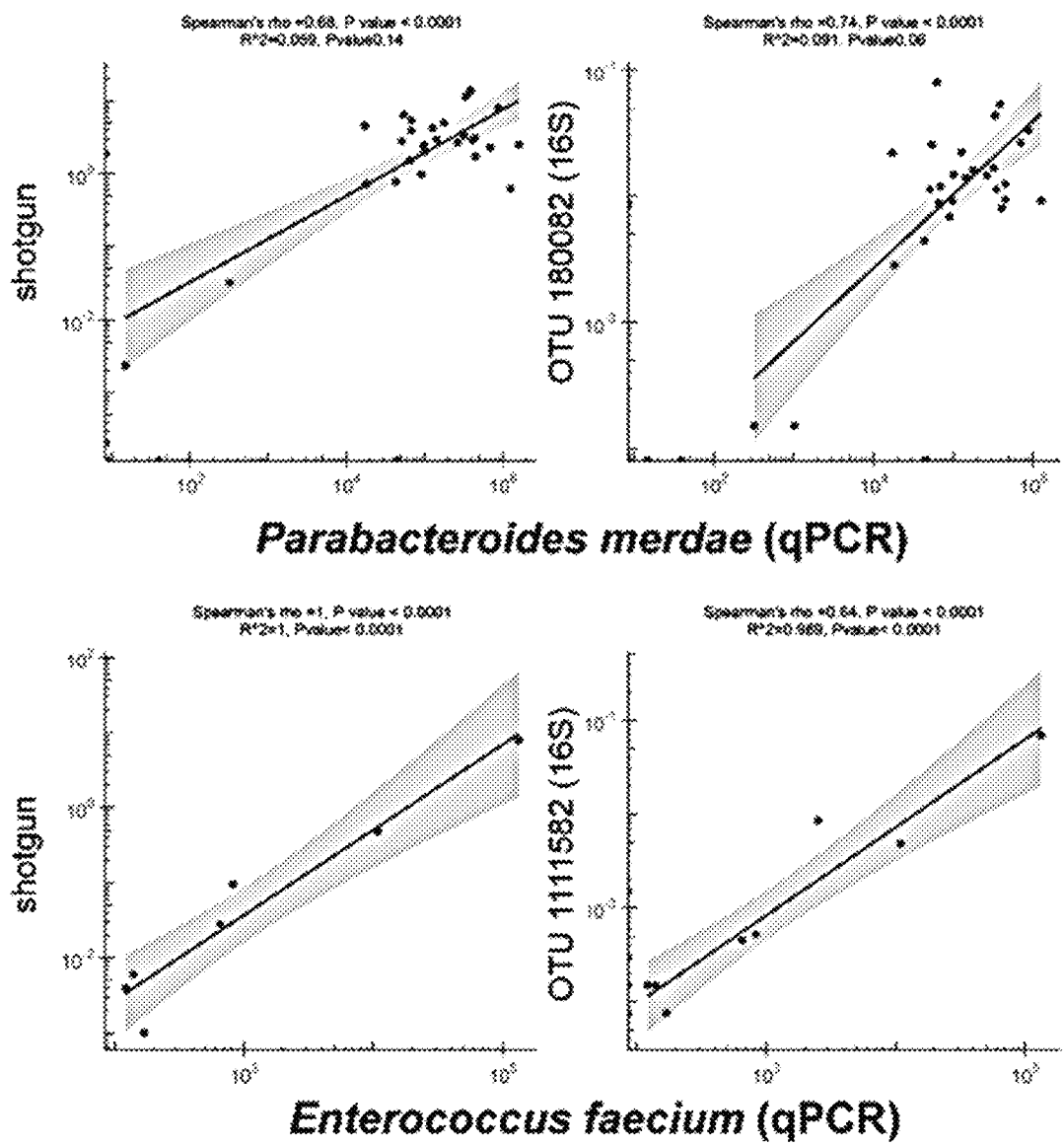
Figure 8:
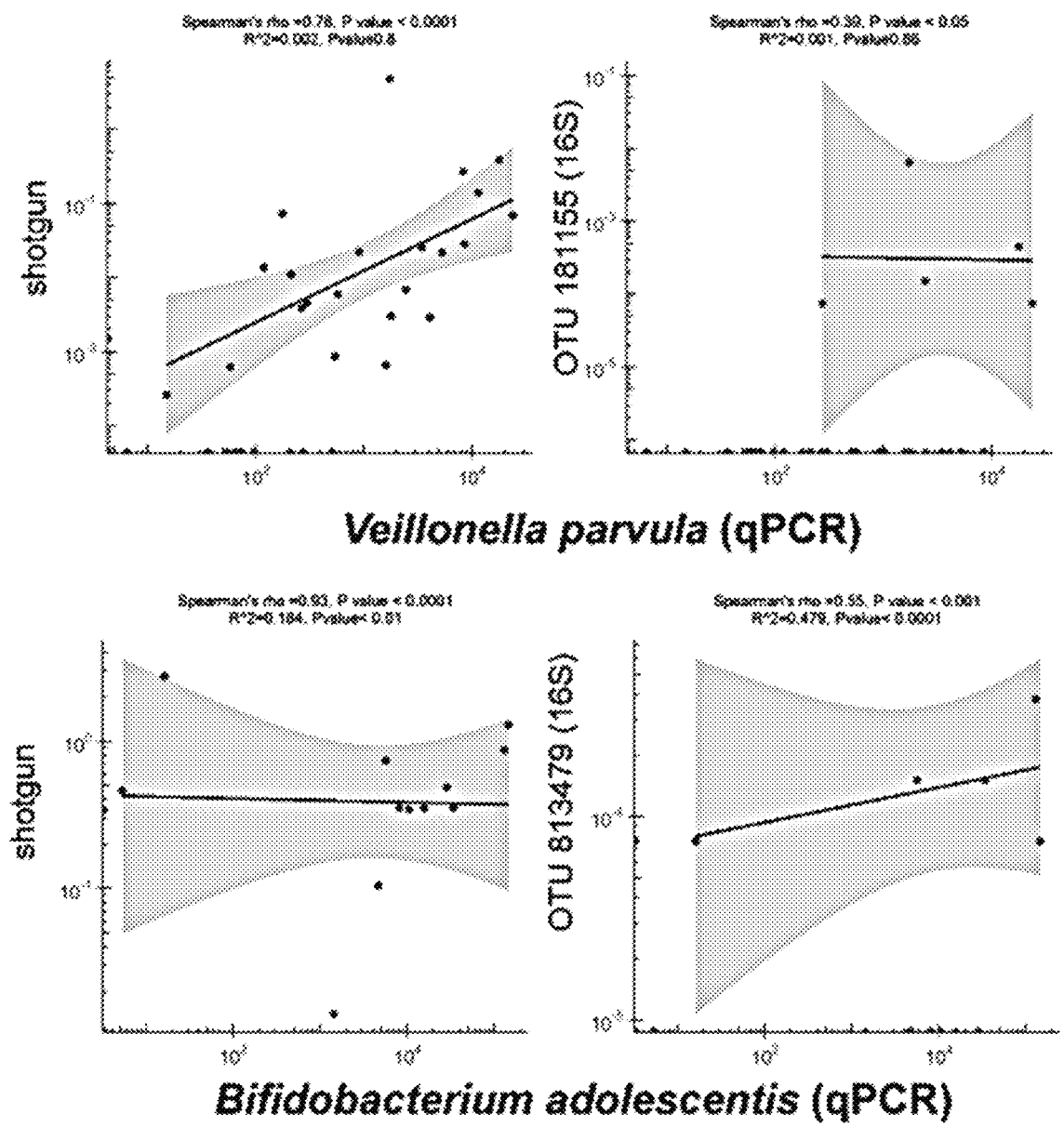
Figure 8:
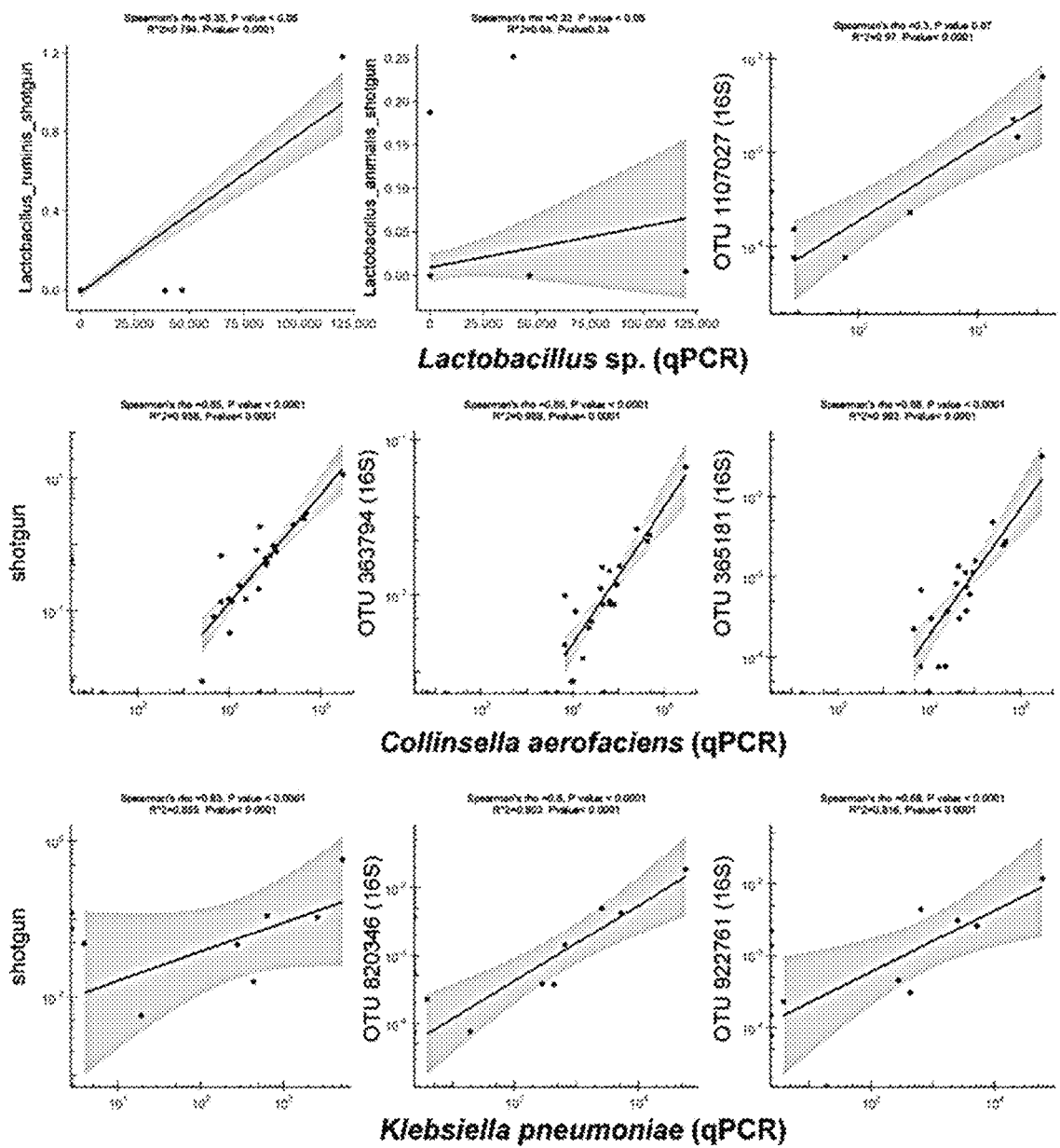
Figure 9:
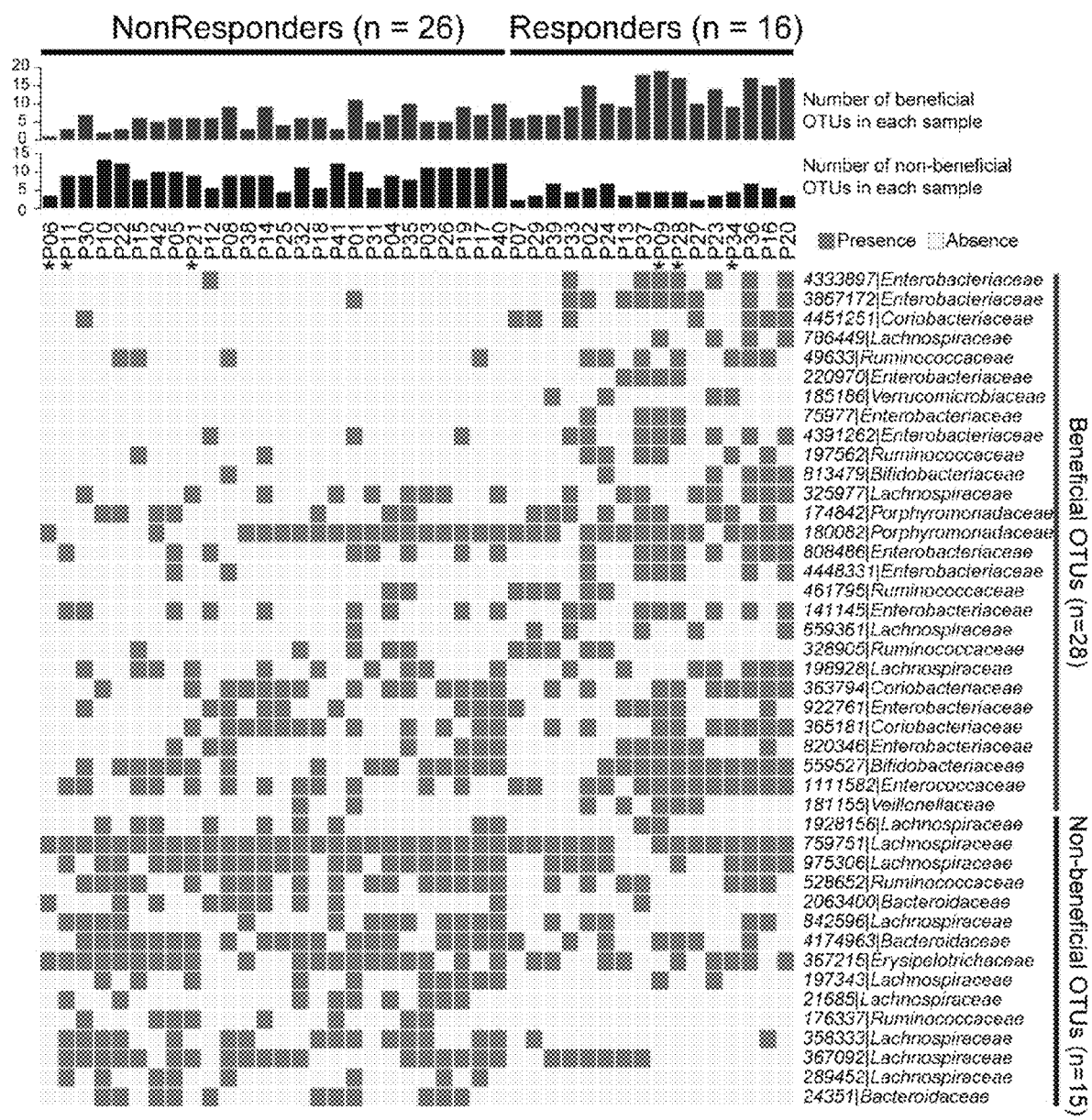
FIG. 9. Visual representation of the presence/absence-based ratio of beneficial/non-beneficial OTUs. The bar graphs represent the total number of potentially beneficial OTUs (more abundant in responders; depicted in red) and potentially non-beneficial OTUs (more abundant in non-responders; depicted in blue) in each patient. The grid map represents presence (green) or absence (white) of beneficial and non-beneficial OTUs in each patient sample. Columns depict individual patients grouped based on clinical response to immunotherapy in the same order as in FIG. 1A. Rows indicate the 43 OTUs from 16S sequencing that were confirmed by shotgun sequencing (Table. 3). Asterisks indicate samples used in further in-vivo experiments. The ID of de novo assembled OTUs (new clean-up reference OTUs picked by QIIME) were abbreviated to show only the unique identifier digits, and the full OTU IDs are provided in Table 2.
Figure 10:
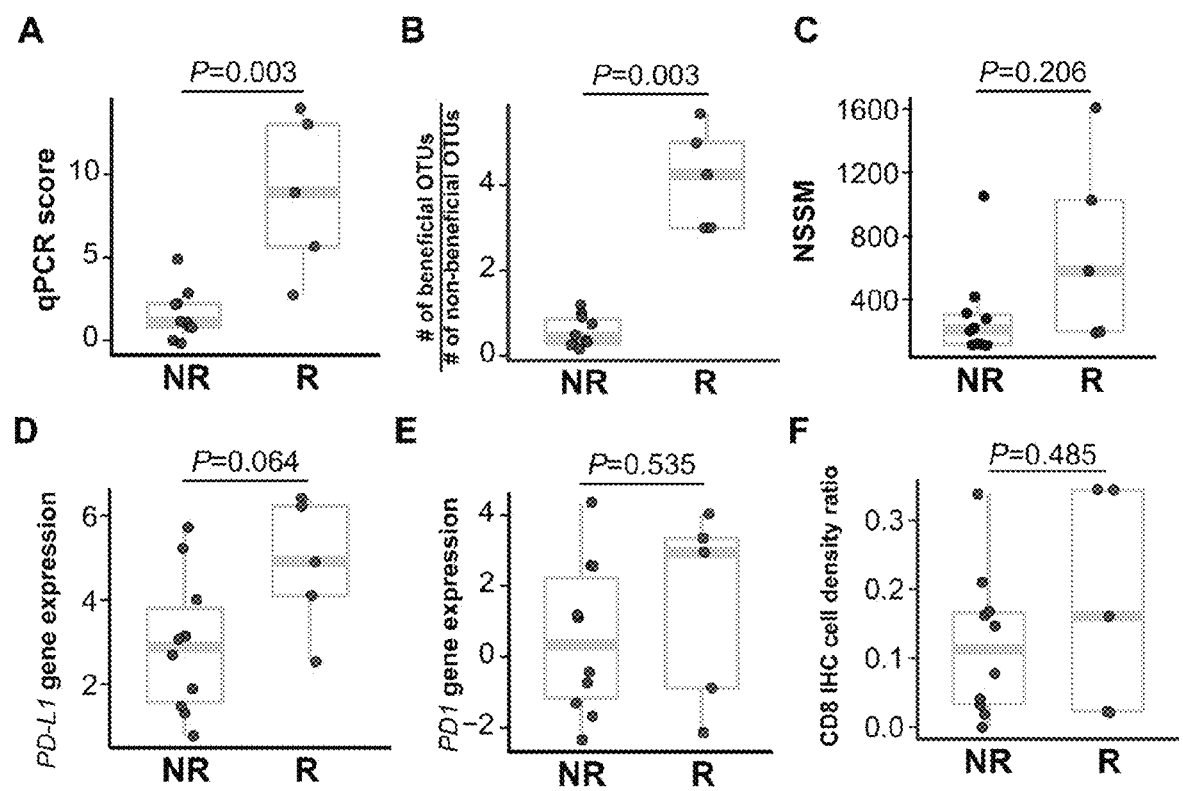
FIG. 10A-F. The qPCR score and the beneficial/non-beneficial OTU ratio as candidate predictors of clinical response to immunotherapy. The qPCR score (A) and the ratio of beneficial-to-non-beneficial OTUs (B) were more distinct between non-responders (NR) and responders (R), compared to the non-synonymous somatic mutational (NSSM) load (C), expression levels of PD-L1 (D) and PD-1 (E), as determined by whole transcriptome sequencing of tumor samples, and intra-tumoral CD8 T cell infiltration (F) as determined with immunohistochemistry of tumor samples. This analysis was limited to subset of 5 responders and 10 non-responders from the original 42 patient cohort, whose samples passed quality control for RNA sequencing. Wilcoxon-Mann-Whitney test (non-parametric) was used for comparing qPCR score, OTU ratio, and NSSM in NR and R groups, which does not assume data follow normal distribution. Student's t-test was used for the rest of the markers.
Figure 11:
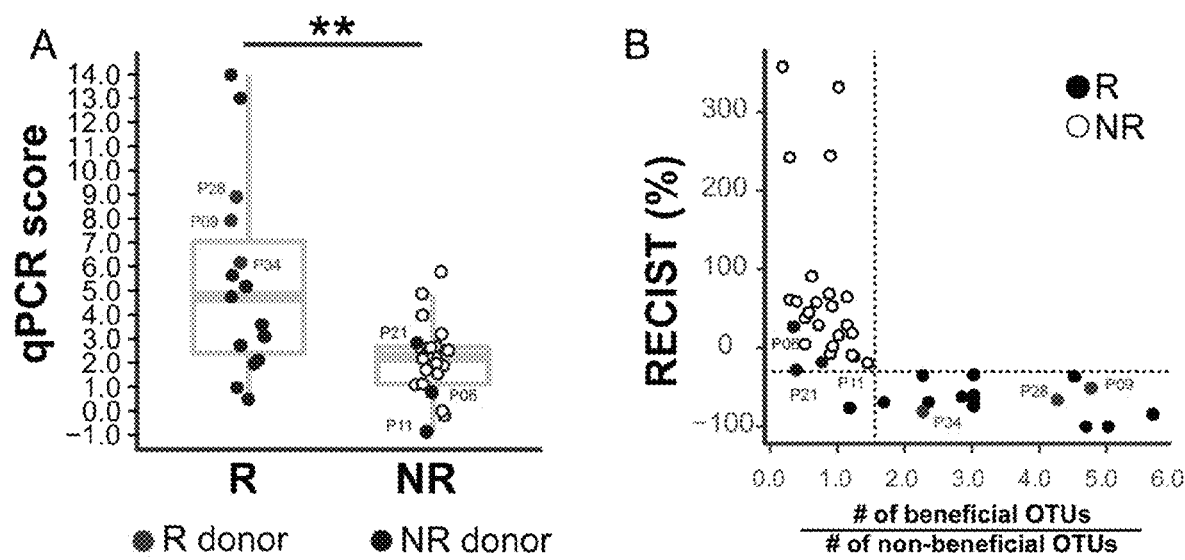
FIG. 11A-B. Donor samples used in mouse colonization experiments are representative of the responder and non-responder patient groups with respect to qPCR score (A) and ratio of beneficial to non-beneficial OTUs (B) as in FIG. 2.

A BLAST search of the 63 OTUs against the NCBI database of bacterial sequences returned multiple species corresponding to each OTU with ≥98% identity. To gain more accurate species-level characterization, the same samples were subjected to metagenomic shotgun sequencing. Illumina paired-end reads were assigned to microbial clades and analyzed for closest matches to the 63 OTUs identified by 16S sequencing. Potential species matches were identified for 43 of the original 63 OTUs (Table 3). Species-specific qPCR assays were performed as an additional approach to assess the identity of species, for which sufficiently validated qPCR primers were available (Table 4A-B). Thus, integration of the three methods led to the selection of 10 species differentially enriched in R vs. NR. Eight of these were more abundant in R: *Enterococcus faecium, Collinsella aerofaciens, Bifidobacterium adolescentis, Klebsiella pneumoniae, Veillonella parvula, Parabacteroides merdae, Lactobacillus sp.* and *Bifidobacterium longum*, whereas 2 were more abundant in NR: *Ruminococcus obeum* and *Roseburia intestinalis*. As an example, the integrative analysis for *B. longum* (OTU 559627) is depicted in FIG. 2A-C. Similar correlation analyses for the remaining 9 species are depicted in FIGS. 7 and 8. PCR results for these 10 species were integrated into a summation PCR score for each patient, which was significantly higher in responders (P=0.004; FIG. 2D). The list of species is likely an underestimate of the total number of entities showing differential abundance in R vs. NR, because of the stringency of this composite analysis. For example, *Akkermansia muciniphila* was detected in 4 patients by 16S sequencing and all were responders, but statistical analysis of the entire cohort did not reach significance. As an alternative way to represent the aggregate data towards development of a candidate predictive biomarker, the total numbers of potentially "beneficial" and "non-beneficial" OTUs were scored for each patient (FIG. 9), and a ratio was calculated). When plotted against the absolute change in tumor size as assessed by RECIST, a clean correlation was observed such that patients with a ratio over 1.5 all showed clinical response (FIG. 2E). These results suggest that the commensal microbiota composition might be useful as a biomarker to predict response to checkpoint blockade therapy, which motivated comparison to other candidate predictive biomarkers. Archived pre-treatment tumor specimens that passed quality control were available for 15 patients (5 R, 10 NR). Microbial composition remained significantly different in R vs. NR for this subset (FIGS. 10A and B). Exome sequencing followed by enumeration of non-synonymous somatic mutations (NSSM) showed a trend of higher frequency in R, as did levels of PD-L1 and PD-1 mRNA (FIG. 10C-E) and enumeration of baseline CD8$^+$ T cells by immunohistochemistry (FIG. 10F). While these statistical trends not meeting significance were likely limited by sample size, it is noteworthy that the microbiota parameters still markedly separated responders and non-responders.

Figure 3A:
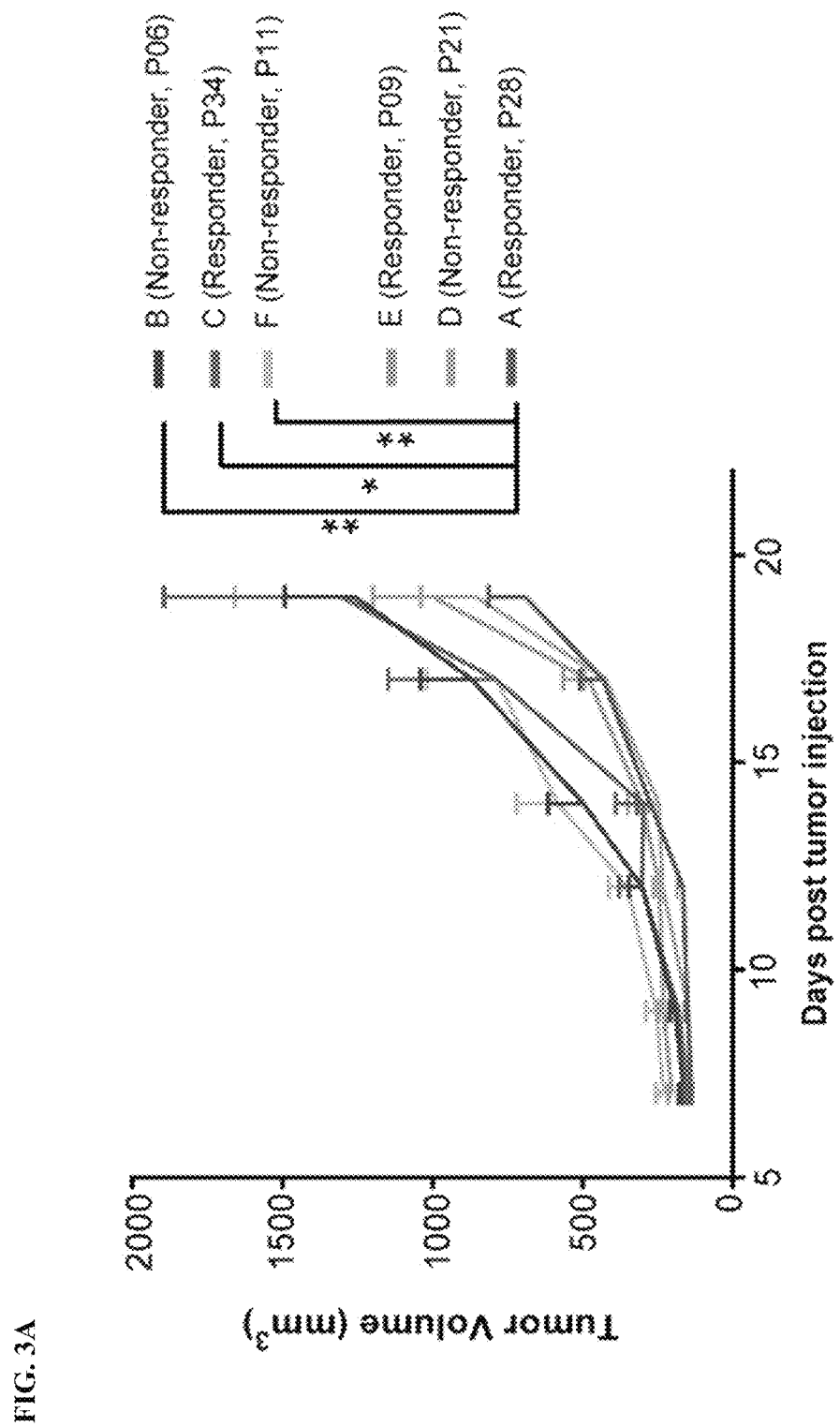
FIG. 3A-G. Human commensal communities modulate anti-tumor immunity in a mouse melanoma model. Germ-free mice were gavaged with fecal material from 3 responder (P28, P34, P09) and 3 non-responder (P06, P21, P11) patient donors. (A) B16.SIY melanoma was injected subcutaneously 2 weeks post-gavage; tumor growth data is from one (groups C, D, E, and F) or two experiments (groups A and B) with 7-11 mice per group per experiment. Error bars represent Mean+SEM. (B) Relative abundance of 207 OTUs from patient donors that colonized in mice, and were differentially abundant between slow and fast tumor growth groups. Columns depict individual mice arranged in groups A through F. Groups A, B, A2, and B2 are from 2 independent duplicate experiments. Rows indicate individual OTUs with exact reference ID match between human and mouse 16S rRNA data sets. (C) In groups A and B, 20 days after B16.SIY injection, ex-vivo activation of splenocytes by SIY peptide was measured with IFN-γ ELISPOT 3 weeks after tumor injection. Tumor-infiltrating SIY-specific CD8$^+$ T cells (D) and FoxP3$^+$ regulatory T cells (E) were enumerated with flow cytometry. (F) Efficacy of anti-PD-L1 therapy was determined in groups A and B. Data are from one experiment with 7-8 mice per group. (G) Relative abundance in mouse groups A and B of key species validated for qPCR scoring. Six out the ten species are shown that gave positive PCR signals. Tumor growth curves were analyzed with two-way ANOVA using Tukey's multiple comparisons post-test, flow cytometry data was analyzed using unpaired, two-tailed Student's t-test, and qPCR data was analyzed using non-parametric Mann-Whitney U test. P<0.05 was considered statistically significant; *P<0.05, P<0.01, *P<0.001, ****P<0.0001.
Figure 12:
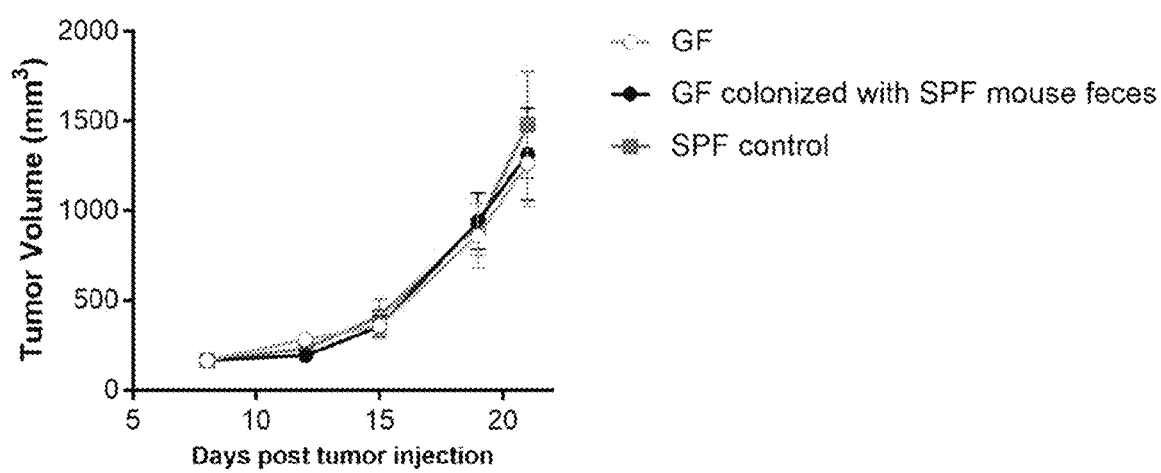
FIG. 12. Germ-free mice and Taconic SPF mice show similar tumor growth rates. Standard specific pathogen-free (SPF) mice were purchased from Taconic. Germ-free (GF) mice, originally purchased from Taconic were bred in the University of Chicago gnotobiotic facility. The GF mice were divided into two groups, and housed in two separate isolators in the same room. One group (black line; n=11) was colonized by oral gavage with fecal material from the SPF mice. The other group remained GF (grey line; n=10). Standard Taconic SPF mice were housed in ventilated cages in a standard barrier facility. All mice were maintained on the same diet. Two weeks later, the mice were injected with B16.SIY melanoma and tumor growth was measured.

The strong correlation between commensal bacteria and clinical response to immunotherapy indicates a causal effect, in light of data demonstrating an immune-potentiating impact of the microbiome in mouse tumor models (Refs. 3B, 5B, 6B; herein incorporated by reference in their entireties). To investigate the capability of human commensal microbes to potentiate anti-tumor T cell responses, germ-free (GF) mice were employed as recipients. In setting up this model, it was found that tumor growth in GF mice was similar to that in Taconic SPF mice and in GF mice colonized with Taconic feces (FIG. 12), indicating reduced spontaneous immune-mediated tumor control in GF mice as had been seen in Taconic compared to Jackson mice previously (ref. 3B; herein incorporated by reference in its entirety). Improved tumor control had been achieved previously with transfer of Jackson fecal material, suggesting that GF mice are suitable hosts for human-derived microbiota with an opportunity to similarly detect improved anti-tumor immunity. Fecal material was transferred from 3 R and 3 NR (indicated in FIGS. 1A, 5, 9, and 11) into cohorts of GF mice, followed by implantation of B16.SIY melanoma cells. The human microbiota-colonized mouse groups segregated into 2 phenotypes with respect to tumor growth rate—a faster growing group and a slower growing group (FIG. 3A). Two of three mouse cohorts reconstituted with R fecal material had slower tumor growth, and two of the three cohorts reconstituted from NR showed faster tumor growth. Thus, the ability of the human microbiota to support improved tumor control in mice usually, but not always, paralleled the clinical response to anti-PD-1 seen in the donor patient. Achieving slower tumor growth with fecal transplant alone is similar to previous mouse studies, in which transfer of feces from Jackson into Taconic mice was sufficient for a partial therapeutic effect (Ref. 3; herein incorporated by reference in its entirety).

Figure 3B:
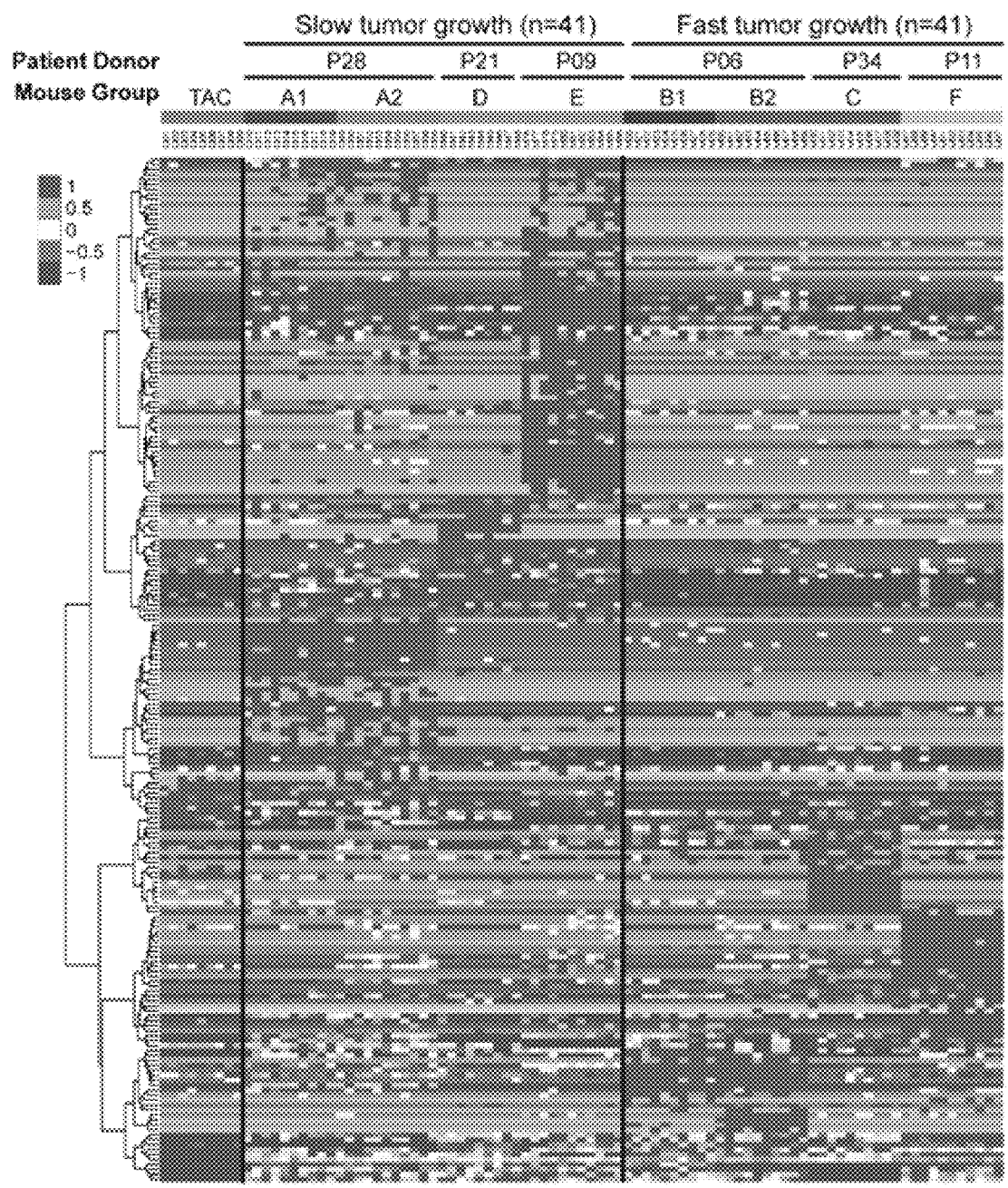
Figure 13:
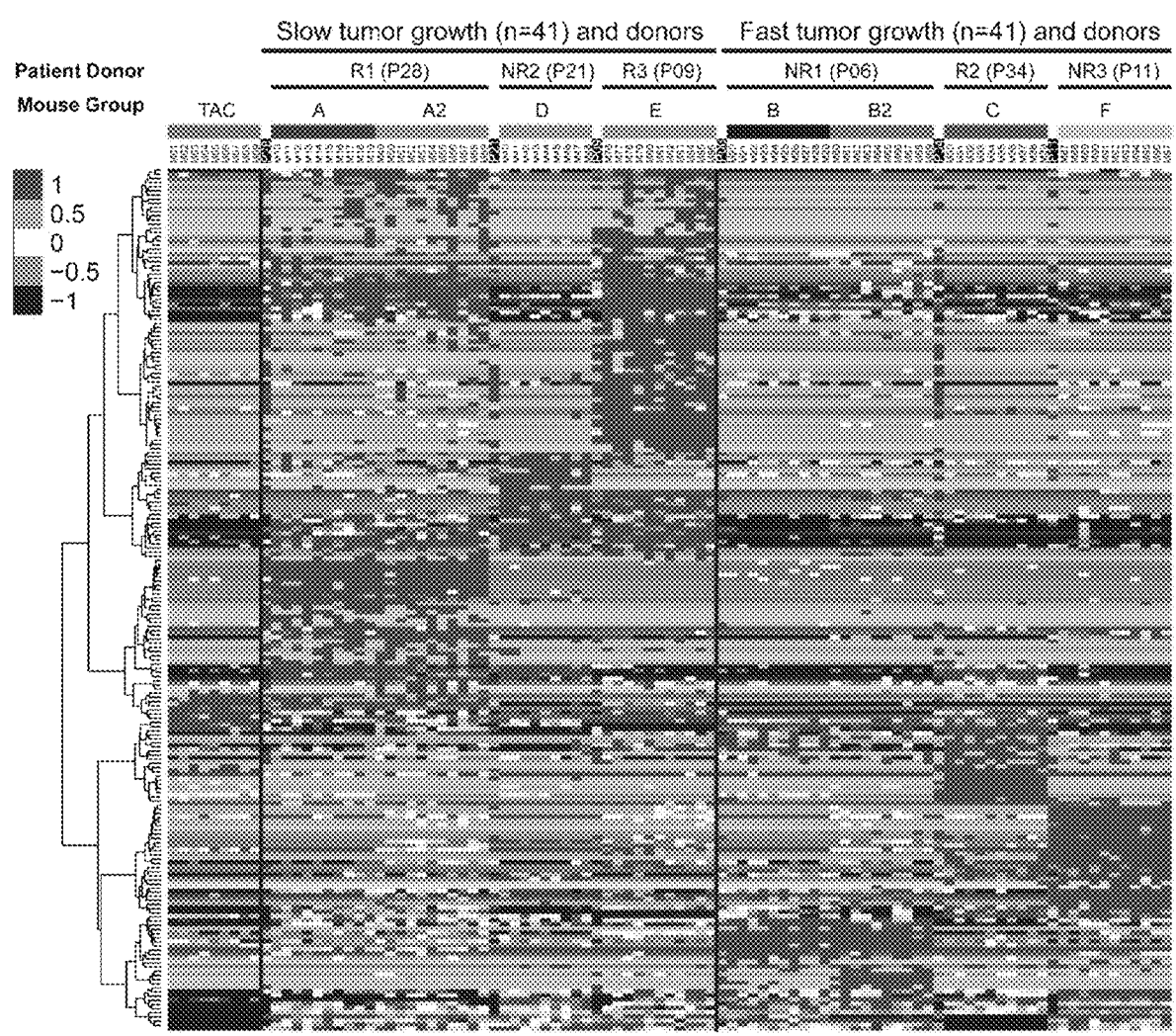
FIG. 13. Relative abundance of 207 OTUs from patient donors that colonized in mice, and were differentially abundant between slow and fast tumor growth groups. Columns depict individual mice arranged in groups A through F, with donor patient samples added at the beginning of each group. Rows indicate individual OTUs with exact reference ID match between human and mouse 16S rRNA data sets.
Figure 14:
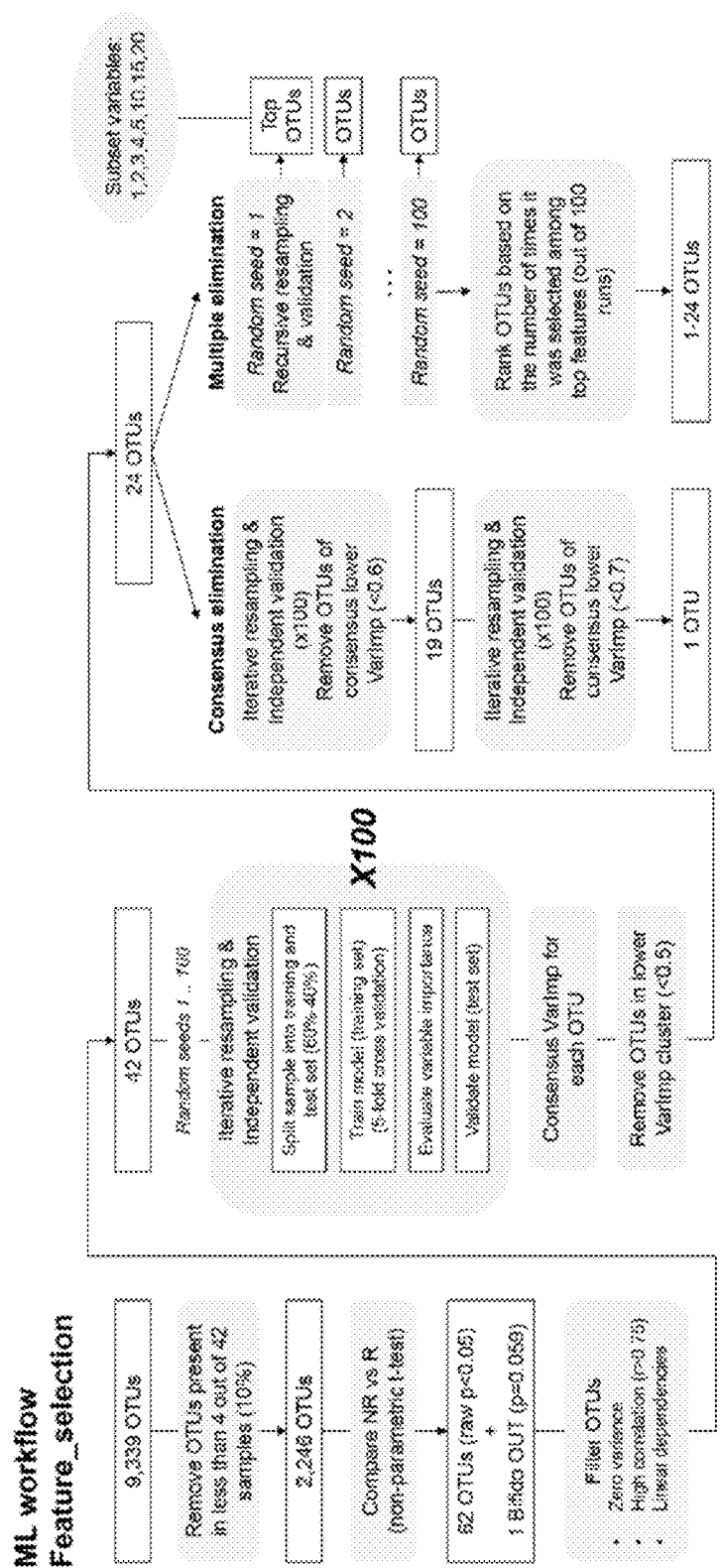
FIG. 14. Exemplary data-driven feature (e.g., OTUs) selection workflow. Experiments were conducted during development of embodiments herein to select important features (e.g., OTUs) in a data-driven manner. The goal was to build a model with the least number of features possible (to reduce the likelihood of overfitting), at the cost of none or limited performance decrease. Models were validated using independent test set, to evaluate performance and to identify potential overfitting problems. 100 random seeds were tested to verify: (i) the stability of variable importance (e.g., that it is not tied to certain "lucky" or "unlucky" seeds), (ii) the stability of model performance (e.g., that it is not tied to a "good" or "bad" resampling; evaluation metric='ROC'), and (iii) consistent performance. Features were selected by iterative resampling and validation. First, consensus elimation is used, running multiple runs (e.g., 100 runs), changing random seeds for different resampling. In each run, model training & validation are performed, variable importance is estimated. After all runs are finished, features are eliminated based on consensus variable importance across the runs.
Figure 15:
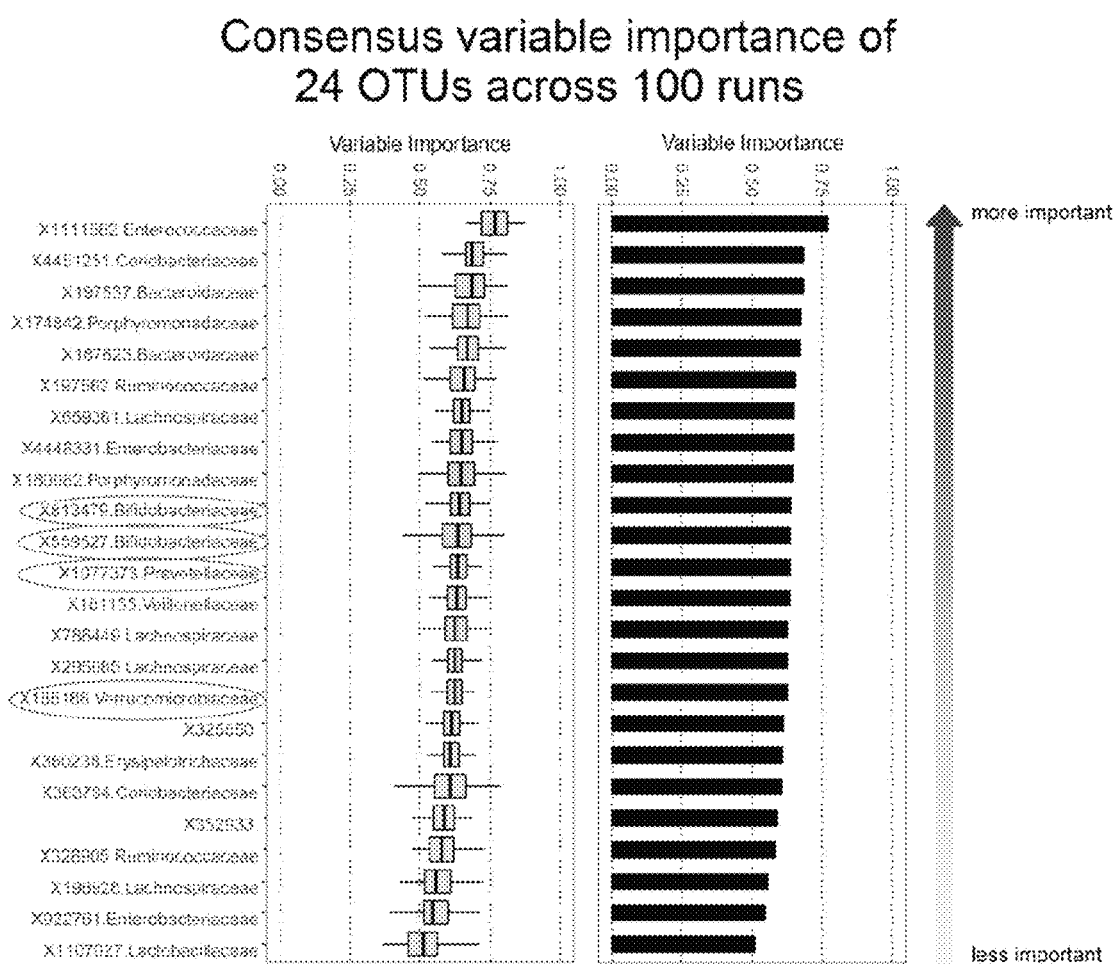
FIG. 15. Consensus variable important of 24 OTUs across 100 runs.

Patterns of bacteria that successfully reconstituted mice and fidelity to the original human donor were assessed with 16S rRNA sequencing. There were significant differences in microbiota composition between the slow and fast tumor growth phenotypes, which were both distinct from Taconic mice (FIG. 3B). Groups C and D, which did not show the same pattern of tumor control as the original human donors, showed a large degree of difference of microbiota composition from the original human donors (FIG. 13). In agreement, a Bray-Curtis dissimilarity index for each donor/recipient pair was highest, at 0.7, for cohorts C and D vs. 0.5-0.6 for the rest of the groups.

Figure 3C:
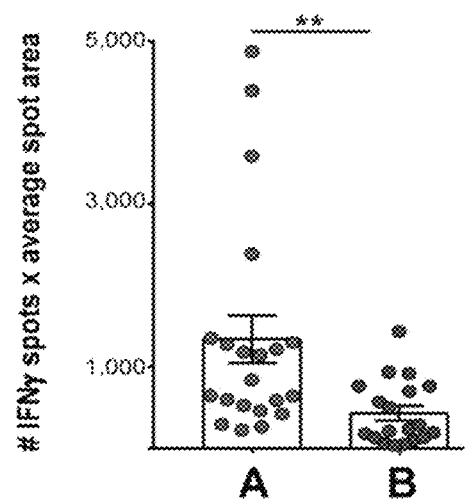
Figure 3D:
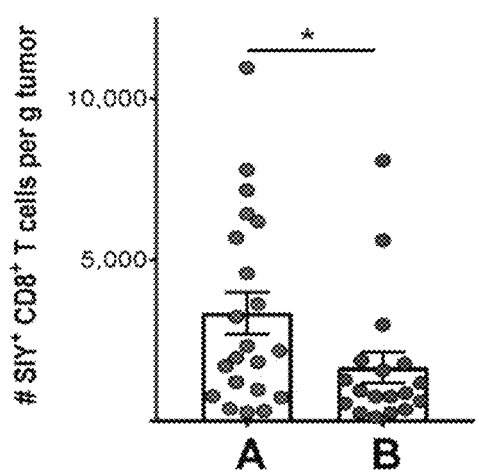
Figure 3E:
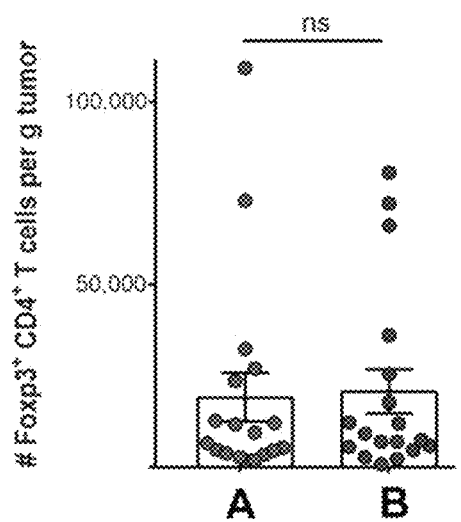
Figure 3G:
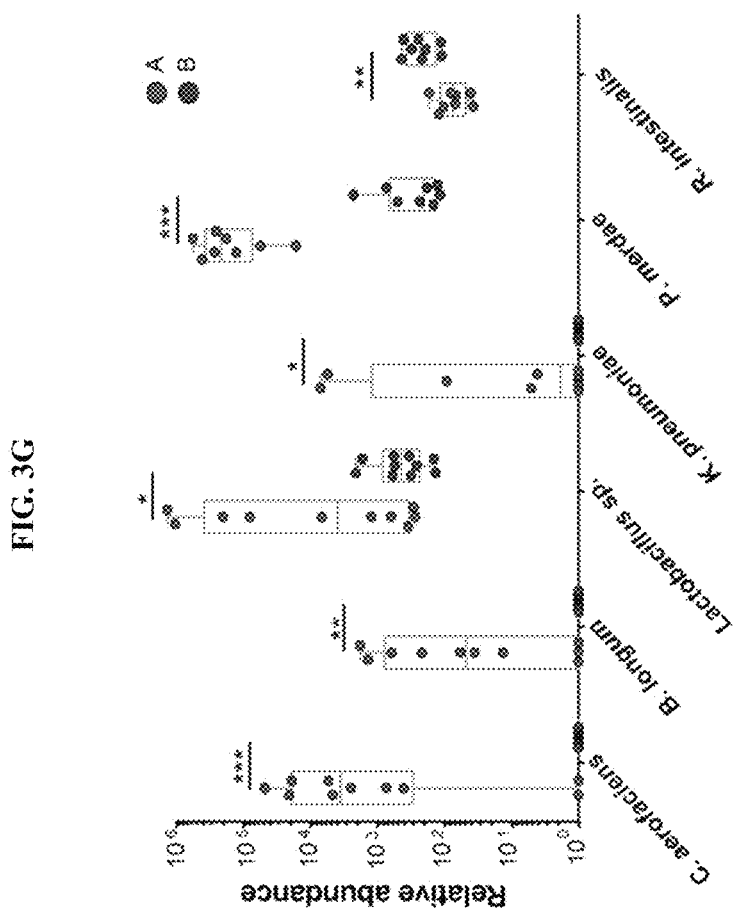
Figure 3F:
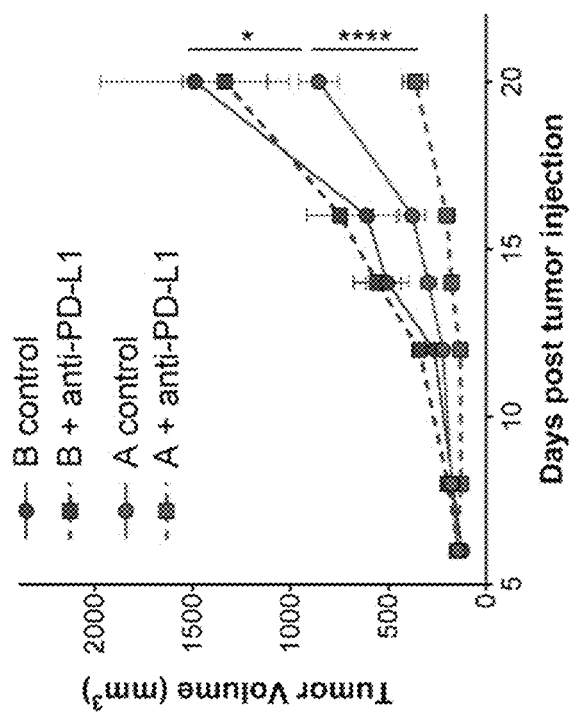

Mouse groups A and B were used for further mechanistic studies. There was a high level of consistency between repeated experiments, both with respect to tumor growth rate and microbial colonization (A vs. A2 and B vs. B2 comparisons in FIG. 3B). To determine whether the difference in tumor control could be attributed to host immunity, IFN-γ ELISPOT of ex-vivo SIY-stimulated splenocytes was performed and indicated an increased frequency of activated T cells from R microbiota-reconstituted mice 3 weeks after inoculation with B16.SIY melanoma cells (FIG. 3C). Analysis of the tumor microenvironment also showed a significantly greater number of SIY-specific CD8$^+$ T cells, but not of FoxP3$^+$CD4$^+$ regulatory T cells, in these mice (FIGS. 3D and E), consistent with increased priming of tumor antigen-specific CD8$^+$ T cells. Anti-PD-L1 was markedly therapeutic in mice colonized with R microbiota, yet completely ineffective in NR-derived mice (FIG. 3F), demonstrating a profound impact of the commensal microbiota on immunotherapy efficacy in vivo. qPCR interrogation of fecal DNA from these mice recapitulated the results from the analysis of patients. Of the 10 PCR reactions validated in patients, 6 gave a signal in reconstituted mice, with the same pattern of being enriched in R or NR recipient mice as was seen in the original patients (FIG. 3G).

The experiments conducted during development of embodiments herein indicate that the composition of the commensal microbiota in patients is associated with therapeutic efficacy of anti-PD-1 mAb. While *Bifidobacterium longum* was one commensal identified in the current study that had also been found in mouse models to be associated with improved immune-mediated tumor control (Ref. 3B; herein incorporated by reference in its entirety), it is likely that multiple specific bacteria may contribute to improved anti-tumor immunity in patients. In addition to the panel of bacteria over-represented in responders, several OTUs were over-represented in non-responders, and prior work in mice has indicated that some commensals have the potential to be immune-inhibitory, for example through the induction of FoxP3+ regulatory T cells (Refs. 7B, 8B; herein incorporated by reference in their entireties) In addition, in the current cohort, a ratio of "beneficial" OTUs to "non-beneficial" OTUs was the strongest predictor of clinical response, indicating that a higher frequency of beneficial bacteria combined with a lower frequency of bacteria of negative impact may combine for the most favorable clinical outcome.

Several of the bacterial species identified in the current study to be differentially abundant in responding vs. non-responding patients have been examined previously for mechanistic impact on host immune responses in germ-free mice in vivo (Ref. 9B; herein incorporated by reference in its entirety). Monocolonization with several species found to be at increased frequency in our responders, including *Enterococcus faecium, Collinsella aerofaciens, Bifidobacterium adolescentis*, and *Parabacteroides merdae*, were reported to result in a decreased frequency of peripherally-derived colonic regulatory T cells compared to other bacterial species. An increased frequency of the Batf3-lineage DCs and greater Th1 responses were also found with bacteria currently identified to be more abundant in responders (Ref. 9B; herein incorporated by reference in its entirety). Decreased Tregs, increased Batf3 DCs, and augmented Th1 responses would all be expected to improve immune-mediated tumor control.

Example 2

Data were generated by 16S rRNA sequencing of patient stool samples (pre-treatment). The reads were assigned to microbe taxa using open-reference OTU picking protocol from QIIME package. About 10,000 OTUs were generated; after filtering those not present in more than 10% of the samples, 2000 OTUs remained. The abundance of OTUs in each sample was estimated, normalized and compared between non-responder (NR) and responder (R) groups. 62 significant OTUs were identified to be differentially present in NR vs R ($p<0.05$), plus one *Bifidobacterium* OTU with $p=0.59$ were include this for subsequent analysis. OTUs identified by the 16S sequencing are listed in Table 6.

TABLE 6

Responder/non-responder bacteria identified by 16S sequencing OTUs.

| Family | Subject Seq-ID | Source |
|---|---|---|
| Enterococcaceae | gi|1158620683|gb|KY129997.1| | *Enterococcus faecium* strain LM13 16S ribosomal RNA gene, partial sequence |
| Enterococcaceae | gi|1158620682|gb|KY129996.1| | *Enterococcus faecium* strain LM5 16S ribosomal RNA gene, partial sequence |
| Enterococcaceae | gi|1158620681|gb|KY129995.1| | *Enterococcus faecium* strain LM2 16S ribosomal RNA gene, partial sequence |
| Enterococcaceae | gi|1153161578|gb|KY697085.1| | *Enterococcus faecalis* strain Cp5 16S ribosomal RNA gene, partial sequence |
| Enterococcaceae | gi|1153161577|gb|KY697084.1| | *Enterococcus faecalis* strain Cp4 16S ribosomal RNA gene, partial sequence |
| Enterococcaceae | gi|1153161576|gb|KY697083.1| | *Enterococcus faecalis* strain Cp3 16S ribosomal RNA gene, partial sequence |
| Enterococcaceae | gi|1153161575|gb|KY697082.1| | *Enterococcus faecalis* strain Cp2 16S ribosomal RNA gene, partial sequence |
| Enterococcaceae | gi|1153161574|gb|KY697081.1| | *Enterococcus faecalis* strain Cp1 16S ribosomal RNA gene, partial sequence |
| Enterococcaceae | gi|1158645201|gb|CP019992.1| | *Enterococcus faecium* isolate 2014-VREF-268, complete genome |
| Enterococcaceae | gi|1158642123|gb|CP019988.1| | *Enterococcus faecium* isolate 2014-VREF-63, complete genome |
| Enterococcaceae | gi|1154289756|gb|CP019970.1| | *Enterococcus faecium* isolate 2014-VREF-114, complete genome |
| Enterococcaceae | gi|1154289756|gb|CP019970.1| | *Enterococcus faecium* isolate 2014-VREF-114, complete genome |
| Enterococcaceae | gi|1150406800|gb|CP019208.1| | *Enterococcus faecium* strain 2014-VREF-41, complete genome |
| Enterococcaceae | gi|1149032865|gb|KY486862.1| | *Enterococcus faecium* strain C52 16S ribosomal RNA gene, partial sequence |
| Enterococcaceae | gi|1149032864|gb|KY486861.1| | *Enterococcus faecium* strain C7 16S ribosomal RNA gene, partial sequence |
| Enterococcaceae | gi|1149032863|gb|KY486860.1| | *Enterococcus faecium* strain C100 16S ribosomal RNA gene, partial sequence |
| Enterococcaceae | gi|1149032562|gb|KX575840.1| | *Enterococcus faecalis* strain DES-1 16S ribosomal RNA gene, partial sequence |
| Enterococcaceae | gi|1148879018|gb|KY630672.1| | *Enterococcus faecalis* strain UFVCC1189 16S ribosomal RNA gene, partial sequence |
| Enterococcaceae | gi|1148879014|gb|KY630668.1| | *Enterococcus faecalis* strain UFVCC1181 16S ribosomal RNA gene, partial sequence |
| Enterococcaceae | gi|1148879008|gb|KY630662.1| | *Enterococcus faecalis* strain UFVCC1180 16S ribosomal RNA gene, partial sequence |

TABLE 6-continued

Responder/non-responder bacteria identified by 16S sequencing OTUs.

| Family | Subject Seq-ID | Source |
| --- | --- | --- |
| Enterococcaceae | gi\|1148303219\|gb\|KX832370.1\| | *Enterococcus faecium* strain 27321 16S ribosomal RNA gene, partial sequence |
| Coriobacteriaceae | gi\|1005392054\|gb\|KU851139.1\| | *Atopobium parvulum* strain R42.12 16S ribosomal RNA gene, partial sequence |
| Coriobacteriaceae | gi\|1139267198\|emb\|LT681140.1\| | *Shuttleworthia satelles* partial 16S rRNA gene, isolate 523N_6554 |
| Coriobacteriaceae | gi\|158263915\|gb\|EU186380.1\| | *Atopobium* sp. DMCT15023 16S ribosomal RNA gene, partial sequence |
| Coriobacteriaceae | gi\|1139287456\|emb\|LT699560.1\| | *Prevotella melaninogenica* partial 16S rRNA gene, isolate R161T_24978 |
| Coriobacteriaceae | gi\|1139268302\|emb\|LT682126.1\| | *Prevotella melaninogenica* partial 16S rRNA gene, isolate 244T_7541 |
| Coriobacteriaceae | gi\|788262483\|gb\|KP192308.1\| | *Atopobium deltae* strain DNF00019 16S ribosomal RNA gene, partial sequence |
| Coriobacteriaceae | gi\|784501155\|dbj\|LC037224.1\| | *Atopobium fossor* gene for 16S ribosomal RNA, partial sequence, strain: JCM 9981 |
| Coriobacteriaceae | gi\|775465093\|dbj\|LC036309.1\| | *Atopobium minutum* gene for 16S ribosomal RNA, partial sequence, strain: JCM 1118 |
| Coriobacteriaceae | gi\|1173202442\|emb\|LT598591.2\| | *Olsenella* sp. Marseille-P3256 partial 16S rRNA gene, strain Marseille-P3256 |
| Coriobacteriaceae | gi\|1182956107\|ref\|NR_146815.1\| | *Olegusella massiliensis* strain KHD7 16S ribosomal RNA, partial sequence |
| Coriobacteriaceae | gi\|1179666524\|dbj\|LC258149.1\| | *Olsenella profusa* gene for 16S ribosomal RNA, partial sequence, strain: JCM 14553 |
| Coriobacteriaceae | gi\|1152067376\|emb\|LT797539.1\| | *Olsenella* sp. Marseille-P3359 partial 16S rRNA gene, strain Marseille-P3359 |
| Coriobacteriaceae | gi\|33089980\|gb\|AY269023.1\| | *Atopobium vaginae* clone FX102-1 16S ribosomal RNA gene, partial sequence |
| Coriobacteriaceae | gi\|1005651670\|gb\|KU726641.1\| | *Atopobium vaginae* strain DNF00180 16S ribosomal RNA gene, partial sequence |
| Coriobacteriaceae | gi\|647404812\|emb\|LK021119.1\| | Bacterium OL-1 partial 16S rRNA gene, isolate OL-1 |
| Coriobacteriaceae | gi\|33089990\|gb\|AY269033.1\| | *Atopobium vaginae* clone FX162-5 16S ribosomal RNA gene, partial sequence |
| Coriobacteriaceae | gi\|33089988\|gb\|AY269031.1\| | *Atopobium vaginae* clone FX119-5 16S ribosomal RNA gene, partial sequence |
| Coriobacteriaceae | gi\|33089986\|gb\|AY269029.1\| | *Atopobium vaginae* clone FX184-1 16S ribosomal RNA gene, partial sequence |
| Coriobacteriaceae | gi\|33089984\|gb\|AY269027.1\| | *Atopobium vaginae* clone FX135-1 16S ribosomal RNA gene, partial sequence |
| Coriobacteriaceae | gi\|33089981\|gb\|AY269024.1\| | *Atopobium vaginae* clone FX103-1 16S ribosomal RNA gene, partial sequence |
| Bacteroidaceae | gi\|1167601288\|gb\|KX658684.1\| | *Bacteroides xylanisolvens* strain A3 16S ribosomal RNA gene, partial sequence |
| Bacteroidaceae | gi\|1181557329\|gb\|KY950632.1\| | *Bacteroides acidifaciens* strain V 16S ribosomal RNA gene, partial sequence |
| Bacteroidaceae | gi\|1173512652\|gb\|CP015401.2\| | *Bacteroides caecimuris* strain I48, complete genome |
| Bacteroidaceae | gi\|1153695773\|gb\|KY703634.1\| | *Anaerostipes* sp. strain KFT8 16S ribosomal RNA gene, partial sequence |
| Bacteroidaceae | gi\|1154066557\|emb\|LT598566.3\| | *Bacteroides* sp. Marseille-P3132 partial 16S rRNA gene, strain Marseille-P3132 |
| Bacteroidaceae | gi\|1074125775\|emb\|LT622246.1\| | *Bacteroides ovatus* V975 genome assembly, chromosome: I |
| Bacteroidaceae | gi\|988570982\|gb\|KR364742.1\| | *Bacteroides* sp. JJM0207-12 16S ribosomal RNA gene, partial sequence |
| Bacteroidaceae | gi\|988570981\|gb\|KR364741.1\| | *Bacteroides caecimuris* strain I48 16S ribosomal RNA gene, partial sequence |
| Bacteroidaceae | gi\|988570980\|gb\|KR364740.1\| | *Bacteroides acidifaciens* strain JJM0207-2 16S ribosomal RNA gene, partial sequence |
| Bacteroidaceae | gi\|745311129\|gb\|KP202688.1\| | *Bacteroides* sp. G25 16S ribosomal RNA gene, partial sequence |
| Bacteroidaceae | gi\|728055098\|gb\|KM396275.1\| | *Bacteroides ovatus* strain G19 16S ribosomal RNA gene, partial sequence |
| Bacteroidaceae | gi\|723001884\|dbj\|AB908394.1\| | *Bacteroides ovatus* gene for 16S ribosomal RNA, partial sequence, strain: EFEL003 |
| Bacteroidaceae | gi\|676402736\|gb\|KM043747.1\| | Bacterium P1C8 16S ribosomal RNA gene, partial sequence |

TABLE 6-continued

Responder/non-responder bacteria identified by 16S sequencing OTUs.

| Family | Subject Seq-ID | Source |
| --- | --- | --- |
| Bacteroidaceae | gi\|672228637\|dbj\|AB908392.1\| | *Bacteroides xylanisolvens* gene for 16S ribosomal RNA, partial sequence, strain: EFEL001 |
| Bacteroidaceae | gi\|159159338\|gb\|EU136694.1\| | *Bacteroides acidifaciens* strain JCM10556 16S ribosomal RNA gene, partial sequence |
| Bacteroidaceae | gi\|636560121\|ref\|NR_116181.1\| | *Bacteroides ovatus* strain JCM5824 16S ribosomal RNA gene, partial sequence<>*Bacteroides ovatus* strain JCM5824 16S ribosomal RNA gene, partial sequence |
| Bacteroidaceae | gi\|636559244\|ref\|NR_115301.1\| | *Bacteroides ovatus* strain CIP 103756 16S ribosomal RNA gene, partial sequence<>*Bacteroides ovatus* 16S ribosomal RNA gene, partial sequence |
| Bacteroidaceae | gi\|148791577\|gb\|EF608211.1\| | *Bacteroides* sp. EBA5-17 16S ribosomal RNA gene, partial sequence |
| Bacteroidaceae | gi\|343201773\|ref\|NR_042499.1\| | *Bacteroides xylanisolvens* strain XB1A 16S ribosomal RNA gene, partial sequence<>*Bacteroides xylanisolvens* partial 16S rRNA gene, type strain XB1AT |
| Bacteroidaceae | gi\|46370580\|gb\|AY538687.1\| | Bacteroidaceae bacterium Smarlab 3301643 16S ribosomal RNA gene, partial sequence |
| Porphyromonadaceae | gi\|1181557324\|gb\|KY950627.1\| | *Parabacteroides distasonis* strain Q 16S ribosomal RNA gene, partial sequence |
| Porphyromonadaceae | gi\|1153695770\|gb\|KY703631.1\| | *Parabacteroides* sp. strain CT06 16S ribosomal RNA gene, partial sequence |
| Porphyromonadaceae | gi\|1153695769\|gb\|KY703630.1\| | *Parabacteroides* sp. strain AT13 16S ribosomal RNA gene, partial sequence |
| Porphyromonadaceae | gi\|159159325\|gb\|EU136681.1\| | *Parabacteroides distasonis* strain JCM5825 16S ribosomal RNA gene, partial sequence |
| Porphyromonadaceae | gi\|149935098\|gb\|CP000140.1\| | *Parabacteroides distasonis* ATCC 8503, complete genome |
| Porphyromonadaceae | gi\|89191772\|dbj\|AB238923.1\| | *Parabacteroides distasonis* gene for 16S ribosomal RNA, partial sequence, strain: JCM 13400 |
| Porphyromonadaceae | gi\|343200655\|ref\|NR_041342.1\| | *Parabacteroides distasonis* strain JCM 5825 16S ribosomal RNA gene, partial sequence<>*Parabacteroides distasonis* gene for 16S ribosomal RNA, partial sequence, strain: JCM 5825 |
| Porphyromonadaceae | gi\|173915\|gb\|M86695.1\|BNRRR16S | *Bacteroides distasonis* 16S ribosomal RNA<>*Parabacteroides* sp. MC_17 partial 16S rRNA gene, strain DSM-20701, isolate MC_17 |
| Porphyromonadaceae | gi\|988571022\|gb\|KR364782.1\| | *Parabacteroides distasonis* strain SAB-131-CoC-3 16S ribosomal RNA gene, partial sequence |
| Porphyromonadaceae | gi\|89191775\|dbj\|AB238926.1\| | *Parabacteroides distasonis* gene for 16S ribosomal RNA, partial sequence, strain: JCM 13403<>*Parabacteroides distasonis* gene for 16S ribosomal RNA, partial sequence, strain: JCM 13404 |
| Porphyromonadaceae | gi\|89191774\|dbj\|AB238925.1\| | *Parabacteroides distasonis* gene for 16S ribosomal RNA, partial sequence, strain: JCM 13402 |
| Porphyromonadaceae | gi\|89191773\|dbj\|AB238924.1\| | *Parabacteroides distasonis* gene for 16S ribosomal RNA, partial sequence, strain: JCM 13401 |
| Porphyromonadaceae | gi\|1154838059\|emb\|LT598573.4\| | *Parabacteroides* sp. Marseille-P3236 partial 16S rRNA gene, strain Marseille-P3136 |
| Porphyromonadaceae | gi\|1046811522\|gb\|KX462878.1\| | *Parabacteroides* sp. strain B3181 16S ribosomal RNA gene, partial sequence |
| Porphyromonadaceae | gi\|1024389103\|emb\|LT558809.1\| | *Bacillus nealsonii* partial 16S rRNA gene, strain Marseille-P2085 |
| Porphyromonadaceae | gi\|1008904221\|emb\|LT223609.1\| | *Parabacteroides faecis* partial 16S rRNA gene, strain Marseille-IHU_AA00074 |
| Porphyromonadaceae | gi\|1142726810\|emb\|LT725663.1\| | *Parabacteroides* sp. Marseille-P3668 partial 16S rRNA gene, strain Marseille-P3668 |

TABLE 6-continued

Responder/non-responder bacteria identified by 16S sequencing OTUs.

| Family | Subject Seq-ID | Source |
| --- | --- | --- |
| Porphyromonadaceae | gi|159159329|gb|EU136685.1| | *Parabacteroides merdae* strain JCM9497 16S ribosomal RNA gene, partial sequence |
| Porphyromonadaceae | gi|343200777|ref|NR_041464.1| | *Parabacteroides johnsonii* strain M-165 16S ribosomal RNA gene, partial sequence<>*Parabacteroides johnsonii* gene for 16S ribosomal RNA, partial sequence |
| Porphyromonadaceae | gi|89191778|dbj|AB238929.1| | *Parabacteroides merdae* gene for 16S ribosomal RNA, partial sequence, strain: JCM 13405 |
| Bacteroidaceae | gi|1167601288|gb|KX658684.1| | *Bacteroides xylanisolvens* strain A3 16S ribosomal RNA gene, partial sequence |
| Bacteroidaceae | gi|1074125775|emb|LT622246.1| | *Bacteroides ovatus* V975 genome assembly, chromosome: 1 |
| Bacteroidaceae | gi|1074125775|emb|LT622246.1| | *Bacteroides ovatus* V975 genome assembly, chromosome: I |
| Bacteroidaceae | gi|988570982|gb|KR364742.1| | *Bacteroides* sp. JJM0207-12 16S ribosomal RNA gene, partial sequence |
| Bacteroidaceae | gi|745311129|gb|KP202688.1| | *Bacteroides* sp. G25 16S ribosomal RNA gene, partial sequence |
| Bacteroidaceae | gi|672228637|dbj|AB908392.1| | *Bacteroides xylanisolvens* gene for 16S ribosomal RNA, partial sequence, strain: EFEL001 |
| Bacteroidaceae | gi|148791577|gb|EF608211.1| | *Bacteroides* sp. EBA5-17 16S ribosomal RNA gene, partial sequence |
| Bacteroidaceae | gi|343201773|ref|NR_042499.1| | *Bacteroides xylanisolvens* strain XB1A 16S ribosomal RNA gene, partial sequence<>*Bacteroides xylanisolvens* partial 16S rRNA gene, type strain XB1AT |
| Bacteroidaceae | gi|46370580|gb|AY538687.1| | Bacteroidaceae bacterium Smarlab 3301643 16S ribosomal RNA gene, partial sequence |
| Bacteroidaceae | gi|1173512652|gb|CP015401.2| | *Bacteroides caecimuris* strain I48, complete genome |
| Bacteroidaceae | gi|988570981|gb|KR364741.1| | *Bacteroides caecimuris* strain I48 16S ribosomal RNA gene, partial sequence |
| Bacteroidaceae | gi|1181557329|gb|KY950632.1| | *Bacteroides acidifaciens* strain V 16S ribosomal RNA gene, partial sequence |
| Bacteroidaceae | gi|1153695773|gb|KY703634.1| | *Anaerostipes* sp. strain KFT8 16S ribosomal RNA gene, partial sequence |
| Bacteroidaceae | gi|988570980|gb|KR364740.1| | *Bacteroides acidifaciens* strain JJM0207-2 16S ribosomal RNA gene, partial sequence |
| Bacteroidaceae | gi|728055098|gb|KM396275.1| | *Bacteroides ovatus* strain G19 16S ribosomal RNA gene, partial sequence |
| Bacteroidaceae | gi|723001884|dbj|AB908394.1| | *Bacteroides ovatus* gene for 16S ribosomal RNA, partial sequence, strain: EFEL003 |
| Bacteroidaceae | gi|676402736|gb|KM043747.1| | Bacterium P1C8 16S ribosomal RNA gene, partial sequence |
| Bacteroidaceae | gi|159159338|gb|EU136694.1| | *Bacteroides acidifaciens* strain JCM10556 16S ribosomal RNA gene, partial sequence |
| Bacteroidaceae | gi|636560121|ref|NR_116181.1| | *Bacteroides ovatus* strain JCM5824 16S ribosomal RNA gene, partial sequence<>*Bacteroides ovatus* strain JCM5824 16S ribosomal RNA gene, partial sequence |
| Bacteroidaceae | gi|636559244|ref|NR_115301.1| | *Bacteroides ovatus* strain CIP 103756 16S ribosomal RNA gene, partial sequence<>*Bacteroides ovatus* 16S ribosomal RNA gene, partial sequence |
| Bacteroidaceae | gi|83627372|dbj|AB222700.1| | *Bacteroides finegoldii* gene for 16S rRNA, partial sequence, strain: JCM 13346 |
| Ruminococcaceae | gi|34558694|gb|AY305307.1| | Butyrate-producing bacterium M21/2 16S ribosomal RNA gene, partial sequence |
| Ruminococcaceae | gi|1031487358|gb|KX150462.1| | *Faecalibacterium* CM04-06 16S ribosomal RNA gene, partial sequence |
| Ruminococcaceae | gi|1031486988|gb|KX146426.1| | *Faecalibacterium* AF52-21 16S ribosomal RNA gene, partial sequence |
| Ruminococcaceae | gi|685210693 |gb|KJ957877.1| | *Faecalibacterium prausnitzii* strain 78_10294632078_070 16S ribosomal RNA gene, partial sequence |

TABLE 6-continued

Responder/non-responder bacteria identified by 16S sequencing OTUs.

| Family | Subject Seq-ID | Source |
|---|---|---|
| Ruminococcaceae | gi|685210692|gb|KJ957876.1| | *Faecalibacterium prausnitzii* strain 67_10294632067_075 16S ribosomal RNA gene, partial sequence |
| Ruminococcaceae | gi|685210691|gb|KJ957875.1| | *Faecalibacterium prausnitzii* strain 63_10294632063_052 16S ribosomal RNA gene, partial sequence |
| Ruminococcaceae | gi|685210690|gb|KJ957874.1| | *Faecalibacterium prausnitzii* strain 59_10294632059_060 16S ribosomal RNA gene, partial sequence |
| Ruminococcaceae | gi|685210689|gb|KJ957873.1| | *Faecalibacterium prausnitzii* strain 56_10294632056_049 16S ribosomal RNA gene, partial sequence |
| Ruminococcaceae | gi|685210687|gb|KJ957871.1| | *Faecalibacterium prausnitzii* strain 51_10294632051_059 16S ribosomal RNA gene, partial sequence |
| Ruminococcaceae | gi|685210685|gb|KJ957869.1| | *Faecalibacterium prausnitzii* strain 45_10299630045_040 16S ribosomal RNA gene, partial sequence |
| Ruminococcaceae | gi|685210684|gb|KJ957868.1| | *Faecalibacterium prausnitzii* strain 31_10294632031_020 16S ribosomal RNA gene, partial sequence |
| Ruminococcaceae | gi|685210683|gb|KJ957867.1| | *Faecalibacterium prausnitzii* strain 29_10294632029_024 16S ribosomal RNA gene, partial sequence |
| Ruminococcaceae | gi|685210682|gb|KJ957866.1| | *Faecalibacterium prausnitzii* strain 28_10294632028_026 16S ribosomal RNA gene, partial sequence |
| Ruminococcaceae | gi|685210681|gb|KJ957865.1| | *Faecalibacterium prausnitzii* strain 27_10294632027_028 16S ribosomal RNA gene, partial sequence |
| Ruminococcaceae | gi|685210680|gb|KJ957864.1| | *Faecalibacterium prausnitzii* strain 25_10294632025_032 16S ribosomal RNA gene, partial sequence |
| Ruminococcaceae | gi|685210679|gb|KJ957863.1| | *Faecalibacterium prausnitzii* strain 24_10297420024_017 16S ribosomal RNA gene, partial sequence |
| Ruminococcaceae | gi|685210678|gb|KJ957862.1| | *Faecalibacterium prausnitzii* strain 24_10294632024_017 16S ribosomal RNA gene, partial sequence |
| Ruminococcaceae | gi|685210677|gb|KJ957861.1| | *Faecalibacterium prausnitzii* strain 23_10294632023_019 16S ribosomal RNA gene, partial sequence |
| Ruminococcaceae | gi|685210676|gb|KJ957860.1| | *Faecalibacterium prausnitzii* strain 22_10294632022_021 16S ribosomal RNA gene, partial sequence |
| Ruminococcaceae | gi|685210675|gb|KJ957859.1| | *Faecalibacterium prausnitzii* strain 20_10294632020_025 16S ribosomal RNA gene, partial sequence |
| Lachnospiraceae | gi|823630656|emb|LN850732.1| | *Eubacterium* sp. SB2 partial 16S rRNA gene, strain SB2 |
| Lachnospiraceae | gi|676402749|gb|KM043760.1| | Bacterium P1B3 16S ribosomal RNA gene, partial sequence |
| Lachnospiraceae | gi|343198924|ref|NR_044048.1| | *Coprococcus comes* strain ATCC 27758 16S ribosomal RNA gene, partial sequence<>*Coprococcus comes* strain ATCC 27758 16S ribosomal RNA gene, partial sequence |
| Lachnospiraceae | gi|34558699|gb|AY305312.1| | Butyrate-producing bacterium SL7/1 16S ribosomal RNA gene, partial sequence |
| Lachnospiraceae | gi|34558692|gb|AY305305.1| | Butyrate-producing bacterium A2-232 16S ribosomal RNA gene, partial sequence |
| Lachnospiraceae | gi|1139937221|emb|LT722679.1| | *Lactonifactor* sp. Marseille-P3743 partial 16S rRNA gene, strain Marseille-P3743 |
| Lachnospiraceae | gi|1008904204|emb|LT223592.1| | *Lactonifactor longoviformis* partial 16S rRNA gene, strain Marseille-P2234 |
| Lachnospiraceae | gi|133779806|gb|EF451053.1| | *Clostridiaceae* bacterium END-2 16S ribosomal RNA gene, partial sequence |
| Lachnospiraceae | gi|988571010|gb|KR364770.1| | *Muricomes intestini* strain 2PG-424-CC-1 16S ribosomal RNA gene, partial sequence |
| Lachnospiraceae | gi|1192786034|dbj|LC269264.1| | *Ruminococcus gauvreauii* gene for 16S ribosomal RNA, partial sequence, strain: JCM 14987 |
| Lachnospiraceae | gi|343205824|ref|NR_044265.1| | *Ruminococcus gauvreauii* strain CCRI-16110 16S ribosomal RNA gene, partial |

TABLE 6-continued

Responder/non-responder bacteria identified by 16S sequencing OTUs.

| Family | Subject Seq-ID | Source |
|---|---|---|
| | | sequence<>*Ruminococcus gauvreauii* strain CCRI-16110 16S ribosomal RNA gene, partial sequence |
| Lachnospiraceae | gi|631251356|ref|NR_112553.1| | [*Clostridium*] *glycyrrhizinilyticum* strain ZM35 16S ribosomal RNA gene, complete sequences<>*Clostridium glycyrrhizinilyticum* gene for 16S ribosomal RNA |
| Lachnospiraceae | gi|57283069|emb|AJ518873.1| | Uncultured bacterium clone p-2205-s959-3 16S ribosomal RNA gene, partial sequence<>*Lachnobacterium* sp. wal 14165 16S rRNA gene |
| Lachnospiraceae | gi|73427036|gb|DQ144122.1| | Butyrate-producing bacterium PH05YB03 16S ribosomal RNA gene, partial sequence |
| Lachnospiraceae | gi|1126366538|dbj|LC192831.1| | *Ruminococcus* sp. JCM 30896 gene for 16S ribosomal RNA, partial sequence, strain: EGH7<>*Ruminococcus* sp. JCM 30896 gene for 16S ribosomal RNA, partial sequence, strain: TSAH33 |
| Lachnospiraceae | gi|1004171141|gb|KT889289.1| | Bacterium 14(2016) 16S ribosomal RNA gene, partial sequence |
| Lachnospiraceae | gi|657357060|dbj|AB849410.1| | Lachnospiraceae bacterium CG22 gene for 16S ribosomal RNA, partial sequence |
| Lachnospiraceae | gi|33242862|gb|AY269188.1| | Human intestinal bacterium julong 601 16S ribosomal RNA gene, complete sequence |
| Lachnospiraceae | gi|90855248|emb|AM039822.1| | *Butyrivibrio fibrisolvens* 16S rRNA gene, strain Mz3 |
| Lachnospiraceae | gi|55818570|gb|AY804152.1| | *Eubacterium rectale* strain S2Ss2/2 16S ribosomal RNA gene, partial sequence |
| Enterobacteriaceae | gi|1151220730|gb|CP019012.1| | *Escherichia coli* strain Ecol_AZ161, complete genome |
| Enterobacteriaceae | gi|1151220730|gb|CP019012.1| | *Escherichia coli* strain Ecol_AZ161, complete genome |
| Enterobacteriaceae | gi|1151220730|gb|CP019012.1| | *Escherichia coli* strain Ecol_AZ161, complete genome |
| Enterobacteriaceae | gi|1160538609|gb|CP011124.1| | *Escherichia coli* strain USML2, complete genome |
| Enterobacteriaceae | gi|1154168274|gb|KY711200.1| | *Escherichia coli* strain AMuM12 16S ribosomal RNA gene, partial sequence |
| Enterobacteriaceae | gi|1154168267|gb|KY711193.1| | *Escherichia coli* strain AMuM2 16S ribosomal RNA gene, partial sequence |
| Enterobacteriaceae | gi|1039023268|gb|KU744859.1| | *Escherichia coli* strain SFSA62 16S ribosomal RNA gene, partial sequence |
| Enterobacteriaceae | gi|1015522073|gb|KU923357.1| | *Escherichia coli* strain USTRW17 16S ribosomal RNA gene, partial sequence |
| Enterobacteriaceae | gi|1015522072|gb|KU923356.1| | *Escherichia coli* strain USTRW16 16S ribosomal RNA gene, partial sequence |
| Enterobacteriaceae | gi|1015522068|gb|KU923352.1| | *Escherichia coli* strain USTRW12 16S ribosomal RNA gene, partial sequence |
| Enterobacteriaceae | gi|1154504417|gb|CP019777.1| | *Escherichia coli* NU14, complete genome |
| Enterobacteriaceae | gi|1154835240|emb|LT795502.1| | *Escherichia coli* strain KV7 genome assembly, chromosome: I |
| Enterobacteriaceae | gi|1150562860|gb|KY678505.1| | *Escherichia coli* strain WXL15 16S ribosomal RNA gene, partial sequence |
| Enterobacteriaceae | gi|1150562859|gb|KY678504.1| | *Escherichia coli* strain WXL13 16S ribosomal RNA gene, partial sequence |
| Enterobacteriaceae | gi|1150562858|gb|KY678503.1| | *Escherichia coli* strain WXL12 16S ribosomal RNA gene, partial sequence |
| Enterobacteriaceae | gi|1150562857|gb|KY678502.1| | *Escherichia coli* strain WXL11 16S ribosomal RNA gene, partial sequence |
| Enterobacteriaceae | gi|1150562856|gb|KY678501.1| | *Escherichia coli* strain WHD 16S ribosomal RNA gene, partial sequence |
| Enterobacteriaceae | gi|1150562855|gb|KY678500.1| | *Escherichia coli* strain XH2H 16S ribosomal RNA gene, partial sequence |
| Enterobacteriaceae | gi|1150562854|gb|KY678499.1| | *Escherichia coli* strain B22H 16S ribosomal RNA gene, partial sequence |
| Enterobacteriaceae | gi|1150562853|gb|KY678498.1| | *Escherichia coli* strain 2H 16S ribosomal RNA gene, partial sequence |
| Enterobacteriaceae | gi|1150562852|gb|KY678497.1| | *Escherichia coli* strain BDZH 16S ribosomal RNA gene, partial sequence |
| Enterobacteriaceae | gi|1153112403|gb|CP019953.1| | *Escherichia coli* M8, complete genome |
| Porphyromonadaceae | gi|159159329|gb|EU136685.1| | *Parabacteroides merdae* strain JCM9497 16S ribosomal RNA gene, partial sequence |

TABLE 6-continued

Responder/non-responder bacteria identified by 16S sequencing OTUs.

| Family | Subject Seq-ID | Source |
| --- | --- | --- |
| Porphyromonadaceae | gi|89191778|dbj|AB238929.1| | *Parabacteroides merdae* gene for 16S ribosomal RNA, partial sequence, strain: JCM 13405 |
| Porphyromonadaceae | gi|343200656|ref|NR_041343.1| | *Parabacteroides merdae* strain JCM 9497 16S ribosomal RNA gene, partial sequence<>*Parabacteroides merdae* gene for 16S ribosomal RNA, partial sequence, strain: JCM 9497 |
| Porphyromonadaceae | gi|343200777|ref|NR_041464.1| | *Parabacteroides johnsonii* strain M-165 16S ribosomal RNA gene, partial sequence<>*Parabacteroides johnsonii* gene for 16S ribosomal RNA, partial sequence |
| Porphyromonadaceae | gi|1181557323|gb|KY950626.1| | *Bacteroides* sp. strain P 16S ribosomal RNA gene, partial sequence |
| Porphyromonadaceae | gi|816399474|gb|GQ456205.2| | *Parabacteroides goldsteinii* strain BS-C3-2 16S ribosomal RNA gene, partial sequence |
| Porphyromonadaceae | gi|159159377|gb|EU136697.1| | *Parabacteroides goldsteinii* strain JCM13446 16S ribosomal RNA gene, partial sequence |
| Porphyromonadaceae | gi|343202832|ref|NR_043317.1| | *Parabacteroides goldsteinii* strain WAL 12034 16S ribosomal RNA gene, partial sequence<>*Parabacteroides goldsteinii* strain WAL 12034 16S ribosomal RNA gene, partial sequence |
| Porphyromonadaceae | gi|1046811522|gb|KX462878.1| | *Parabacteroides* sp. strain B3181 16S ribosomal RNA gene, partial sequence |
| Porphyromonadaceae | gi|1142726810|emb|LT725663.1| | *Parabacteroides* sp. Marseille-P3668 partial 16S rRNA gene, strain Marseille-P3668 |
| Porphyromonadaceae | gi|1024389103|emb|LT558809.1| | *Bacillus nealsonii* partial 16S rRNA gene, strain Marseille-P2085 |
| Porphyromonadaceae | gi|1008904221|emb|LT223609.1| | *Parabacteroides faecis* partial 16S rRNA gene, strain Marseille-IHU_AA00074 |
| Porphyromonadaceae | gi|1154838059|emb|LT598573.4| | *Parabacteroides* sp. Marseille-P3236 partial 16S rRNA gene, strain Marseille-P3136 |
| Porphyromonadaceae | gi|1139937223|emb|LT722681.1| | *Parabacteroides* sp. Marseille-P3763 partial 16S rRNA gene, strain Marseille-P3763 |
| Porphyromonadaceae | gi|10946530|gb|AY008308.1| | *Bacteroides* cf. *forsythus* oral clone BU063 16S ribosomal RNA gene, partial sequence |
| Porphyromonadaceae | gi|1061022501|gb|CP017038.1| | *Tannerella* sp. oral taxon BU063, complete genome |
| Porphyromonadaceae | gi|751868059|dbj|LC021528.1| | *Dysgonomonas alginatilytica* gene for 16S ribosomal RNA, partial sequence, strain: HUA-2 |
| Porphyromonadaceae | gi|677007119|gb|KJ888430.1| | *Dysgonomonas* sp. DT183 16S ribosomal RNA gene, partial sequence |
| Porphyromonadaceae | gi|173915|gb|M86695.1|BNRRR16S | *Bacteroides distasonis* 16S ribosomal RNA<>*Parabacteroides* sp. MC_17 partial 16S rRNA gene, strain DSM-20701, isolate MC_17 |
| Porphyromonadaceae | gi|1153695770|gb|KY703631.1| | *Parabacteroides* sp. strain CT06 16S ribosomal RNA gene, partial sequence |
| Bifidobacteriaceae | gi|1153683744|gb|KY705021.1| | *Bifidobacterium longum* subsp. *suis* strain VB-5/9 16S ribosomal RNA gene, partial sequence |
| Bifidobacteriaceae | gi|1153683742|gb|KY705019.1| | *Bifidobacterium breve* strain VB-TA1 16S ribosomal RNA gene, partial sequence |
| Bifidobacteriaceae | gi|1153683740|gb|KY705017.1| | *Bifidobacterium adolescentis* strain VB-ES42 16S ribosomal RNA gene, partial sequence |
| Bifidobacteriaceae | gi|1141357803|gb|KY448280.1| | *Bifidobacterium longum* strain CFR815k 16S ribosomal RNA gene, partial sequence |
| Bifidobacteriaceae | gi|1141357802|gb|KY448279.1| | *Bifidobacterium longum* strain CFR56 16S ribosomal RNA gene, partial sequence |
| Bifidobacteriaceae | gi|1141357801|gb|KY448278.1| | *Bifidobacterium longum* strain CFR50 16S ribosomal RNA gene, partial sequence |

TABLE 6-continued

Responder/non-responder bacteria identified by 16S sequencing OTUs.

| Family | Subject Seq-ID | Source |
| --- | --- | --- |
| Bifidobacteriaceae | gi|1141357800|gb|KY448277.1| | *Bifidobacterium longum* strain CFR24 16S ribosomal RNA gene, partial sequence |
| Bifidobacteriaceae | gi|1141357799|gb|KY448276.1| | *Bifidobacterium longum* strain CFR 20 16S ribosomal RNA gene, partial sequence |
| Bifidobacteriaceae | gi|1141357789|gb|KU297199.1| | *Bifidobacterium longum* strain 815j 16S ribosomal RNA gene, partial sequence |
| Bifidobacteriaceae | gi|1141357788|gb|KU297198.1| | *Bifidobacterium breve* strain 142 16S ribosomal RNA gene, partial sequence |
| Bifidobacteriaceae | gi|1143275817|gb|CP019596.1| | *Bifidobacterium breve* strain LMC520, complete genome |
| Bifidobacteriaceae | gi|1137292025|gb|KY523590.1| | *Bifidobacterium adolescentis* strain S52 16S ribosomal RNA gene, partial sequence |
| Bifidobacteriaceae | gi|1137292022|gb|KY523587.1| | *Bifidobacterium adolescentis* strain S42 16S ribosomal RNA gene, partial sequence |
| Bifidobacteriaceae | gi|1137292017|gb|KY523582.1| | *Bifidobacterium* sp. strain S35 16S ribosomal RNA gene, partial sequence |
| Bifidobacteriaceae | gi|1137291996|gb|KY523561.1| | *Bifidobacterium longum* strain S53 16S ribosomal RNA gene, partial sequence |
| Bifidobacteriaceae | gi|1137291995|gb|KY523560.1| | *Bifidobacterium adolescentis* strain S50 16S ribosomal RNA gene, partial sequence |
| Bifidobacteriaceae | gi|1137291993|gb|KY523558.1| | *Bifidobacterium adolescentis* strain S47 16S ribosomal RNA gene, partial sequence |
| Bifidobacteriaceae | gi|1137291991|gb|KY523556.1| | *Bifidobacterium longum* strain S34 16S ribosomal RNA gene, partial sequence |
| Bifidobacteriaceae | gi|1137647753|ref|NR_145535.1| | *Bifidobacterium longum* subsp. *suillum* strain Su 851 16S ribosomal RNA, partial sequence |
| Bifidobacteriaceae | gi|1024389105|emb|LT558811.1| | *Bifidobacterium adolescentis* partial 16S rRNA gene, strain Marseille-P830 |
| Bifidobacteriaceae | gi|1153683744|gb|KY705021.1| | *Bifidobacterium longum* subsp. *suis* strain VB-5/9 16S ribosomal RNA gene, partial sequence |
| Bifidobacteriaceae | gi|1153683742|gb|KY705019.1| | *Bifidobacterium breve* strain VB-TA1 16S ribosomal RNA gene, partial sequence |
| Bifidobacteriaceae | gi|1153683740|gb|KY705017.1| | *Bifidobacterium adolescentis* strain VB-ES42 16S ribosomal RNA gene, partial sequence |
| Bifidobacteriaceae | gi|1141357803|gb|KY448280.1| | *Bifidobacterium longum* strain CFR815k 16S ribosomal RNA gene, partial sequence |
| Bifidobacteriaceae | gi|1141357802|gb|KY448279.1| | *Bifidobacterium longum* strain CFR56 16S ribosomal RNA gene, partial sequence |
| Bifidobacteriaceae | gi|1141357801|gb|KY448278.1| | *Bifidobacterium longum* strain CFR50 16S ribosomal RNA gene, partial sequence |
| Bifidobacteriaceae | gi|1141357800|gb|KY448277.1| | *Bifidobacterium longum* strain CFR24 16S ribosomal RNA gene, partial sequence |
| Bifidobacteriaceae | gi|1141357799|gb|KY448276.1| | *Bifidobacterium longum* strain CFR 20 16S ribosomal RNA gene, partial sequence |
| Bifidobacteriaceae | gi|1141357789|gb|KU297199.1| | *Bifidobacterium longum* strain 815j 16S ribosomal RNA gene, partial sequence |
| Bifidobacteriaceae | gi|1141357788|gb|KU297198.1| | *Bifidobacterium breve* strain 142 16S ribosomal RNA gene, partial sequence |
| Bifidobacteriaceae | gi|1143275817|gb|CP019596.1| | *Bifidobacterium breve* strain LMC520, complete genome |
| Bifidobacteriaceae | gi|1137292025|gb|KY523590.1| | *Bifidobacterium adolescentis* strain S52 16S ribosomal RNA gene, partial sequence |
| Bifidobacteriaceae | gi|1137292022|gb|KY523587.1| | *Bifidobacterium adolescentis* strain S42 16S ribosomal RNA gene, partial sequence |
| Bifidobacteriaceae | gi|1137292017|gb|KY523582.1| | *Bifidobacterium* sp. strain S35 16S ribosomal RNA gene, partial sequence |
| Bifidobacteriaceae | gi|1137291996|gb|KY523561.1| | *Bifidobacterium longum* strain S53 16S ribosomal RNA gene, partial sequence |

TABLE 6-continued

Responder/non-responder bacteria identified by 16S sequencing OTUs.

| Family | Subject Seq-ID | Source |
| --- | --- | --- |
| Bifidobacteriaceae | gi|1137291995|gb|KY523560.1| | *Bifidobacterium adolescentis* strain S50 16S ribosomal RNA gene, partial sequence |
| Bifidobacteriaceae | gi|1137291993|gb|KY523558.1| | *Bifidobacterium adolescentis* strain S47 16S ribosomal RNA gene, partial sequence |
| Bifidobacteriaceae | gi|1137291991|gb|KY523556.1| | *Bifidobacterium longum* strain S34 16S ribosomal RNA gene, partial sequence |
| Bifidobacteriaceae | gi|1137647753|ref|NR_145535.1| | *Bifidobacterium longum* subsp. *suillum* strain Su 851 16S ribosomal RNA, partial sequence |
| Bifidobacteriaceae | gi|1024389105|emb|LT558811.1| | *Bifidobacterium adolescentis* partial 16S rRNA gene, strain Marseille-P830 |
| Prevotellaceae | gi|82618889|gb|DQ278861.1| | *Prevotella* sp. 152R-1a 16S ribosomal RNA gene, partial sequence |
| Prevotellaceae | gi|343198858|ref|NR_043894.1| | *Prevotella timonensis* strain 4401737 16S ribosomal RNA gene, partial sequence<>*Prevotella timonensis* strain 4401737 16S ribosomal RNA gene, partial sequence |
| Prevotellaceae | gi|343200677|ref|NR_041364.1| | *Prevotella stercorea* strain CB35 16S ribosomal RNA gene, partial sequence<>*Prevotella stercorea* gene for 16S ribosomal RNA, partial sequence, strain: CB35 |
| Prevotellaceae | gi|1139287453|emb|LT699557.1| | *Streptococcus anginosus* partial 16S rRNA gene, isolate R161T_24975 |
| Prevotellaceae | gi|166063928|dbj|AB298732.2| | *Prevotellaceae bacterium* WR041 gene for 16S rRNA, partial sequence |
| Prevotellaceae | gi|343200237|ref|NR_040924.1| | *Prevotella paludivivens* strain KB7 16S ribosomal RNA gene, partial sequence<>*Prevotella paludivivens* gene for 16S ribosomal RNA, partial sequence, strain: KB7 |
| Prevotellaceae | gi|343198484|ref|NR_041907.1| | *Prevotella marshii* strain E9.34 16S ribosomal RNA gene, partial sequence<>*Prevotella marshii* strain E9.34 16S ribosomal RNA gene, partial sequence |
| Prevotellaceae | gi|1139291348|emb|LT677943.1| | *Prevotella nigrescens* partial 16S rRNA gene, isolate 219N_3357 |
| Prevotellaceae | gi|1139291337|emb|LT677932.1| | *Prevotella nigrescens* partial 16S rRNA gene, isolate 219N_3346 |
| Prevotellaceae | gi|1139291306|emb|LT677901.1| | *Prevotella nigrescens* partial 16S rRNA gene, isolate 219N_3315 |
| Prevotellaceae | gi|1139290143|emb|LT676740.1| | *Prevotella nigrescens* partial 16S rRNA gene, isolate 492N_2154 |
| Prevotellaceae | gi|1139290140|emb|LT676737.1| | *Prevotella nigrescens* partial 16S rRNA gene, isolate 492N_2151 |
| Prevotellaceae | gi|1139289788|emb|LT676439.1| | *Prevotella nigrescens* partial 16S rRNA gene, isolate W731N_1853 |
| Prevotellaceae | gi|1139289722|emb|LT676373.1| | *Prevotella nigrescens* partial 16S rRNA gene, isolate W731N_1787 |
| Prevotellaceae | gi|1139288883|emb|LT675486.1| | *Prevotella nigrescens* partial 16S rRNA gene, isolate W731T_900 |
| Prevotellaceae | gi|1139288535|emb|LT675139.1| | *Prevotella nigrescen* partial 16S rRNA gene, isolate 256N_553 |
| Prevotellaceae | gi|1139287425|emb|LT699529.1| | *Prevotella nigrescens* partial 16S rRNA gene, isolate R161T_24947 |
| Prevotellaceae | gi|1139285456|emb|LT699586.1| | *Prevotella nigrescens* partial 16S rRNA gene, isolate R161T_25004 |
| Prevotellaceae | gi|1139284226|emb|LT698245.1| | *Prevotella nigrescens* partial 16S rRNA gene, isolate W066N_23663 |
| Prevotellaceae | gi|1139284222|emb|LT698241.1| | *Prevotella nigrescens* partial 16S rRNA gene, isolate W066N_23659 |
| Veillonellaceae | gi|1148994964|gb|CP019721.1| | *Veillonella parvula* strain UTDB1-3, complete genome |
| Veillonellaceae | gi|1148994964|gb|CP019721.1| | *Veillonella parvula* strain UTDB1-3, complete genome |
| Veillonellaceae | gi|1148994964|gb|CP019721.1| | *Veillonella parvula* strain UTDB1-3, complete genome |
| Veillonellaceae | gi|1139270738|emb|LT684451.1| | *Veillonella dispar* partial 16S rRNA gene, isolate 189N_9866 |
| Veillonellaceae | gi|17017249|gb|AF439645.1| | *Veillonella* sp. ADV 360.00 16S ribosomal RNA gene, partial sequence |

TABLE 6-continued

Responder/non-responder bacteria identified by 16S sequencing OTUs.

| Family | Subject Seq-ID | Source |
|---|---|---|
| Veillonellaceae | gi\|17017246\|gb\|AF439642.1\| | *Veillonella* sp. ADV 360.00 16S ribosomal RNA gene, partial sequence |
| Veillonellaceae | gi\|45861433\|gb\|AY571668.1\| | *Veillonella* sp. ADV 269.01 16S ribosomal RNA gene, partial sequence |
| Veillonellaceae | gi\|1175700537\|gb\|CP020566.1\| | *Veillonella atypica* strain OK5, complete genome |
| Veillonellaceae | gi\|1139289771\|emb\|LT676422.1\| | *Veillonella dispar* partial 16S rRNA gene, isolate W731N_1836 |
| Veillonellaceae | gi\|1139281643\|emb\|LT695664.1\| | *Veillonella dispar* partial 16S rRNA gene, isolate 468N_21082 |
| Veillonellaceae | gi\|1139281465\|emb\|LT695486.1\| | *Veillonella dispar* partial 16S rRNA gene, isolate 39T_20904 |
| Veillonellaceae | gi\|1139276978\|emb\|LT691051.1\| | *Veillonella dispar* partial 16S rRNA gene, isolate 210T_16467 |
| Veillonellaceae | gi\|1139272749\|emb\|LT686946.1\| | *Veillonella dispar* partial 16S rRNA gene, isolate W153N_12361 |
| Veillonellaceae | gi\|1139271787\|emb\|LT685808.1\| | *Veillonella dispar* partial 16S rRNA gene, isolate W297T_11223 |
| Veillonellaceae | gi\|1139269990\|emb\|LT684009.1\| | *Veillonella dispar* partial 16S rRNA gene, isolate 377N_9424 |
| Veillonellaceae | gi\|1139269916\|emb\|LT683633.1\| | *Veillonella dispar* partial 16S rRNA gene, isolate 482T_9048 |
| Veillonellaceae | gi\|1139269897\|emb\|LT683614.1\| | *Veillonella dispar* partial 16S rRNA gene, isolate 482T_9029 |
| Veillonellaceae | gi\|1005392159\|gb\|KU851244.1\| | *Veillonella atypica* strain TCD56.9 16S ribosomal RNA gene, partial sequence |
| Veillonellaceae | gi\|343201163\|ref\|NR_041879.1\| | *Veillonella dispar* strain ATCC 17748 16S ribosomal RNA gene, partial sequence<>*Veillonella dispar* 16S ribosomal RNA gene, partial sequence |
| Veillonellaceae | gi\|1139289571\|emb\|LT675824.1\| | *Veillonella dispar* partial 16S rRNA gene, isolate 467N_1238 |
| Veillonellaceae | gi\|1005392160\|gb\|KU851245.1\| | *Veillonella atypica* strain TCD60.3 16S ribosomal RNA gene, partial sequence |
| Veillonellaceae | gi\|1005392161\|gb\|KU851246.1\| | *Veillonella atypica* strain R39.8 16S ribosomal RNA gene, partial sequence |
| Lachnospiraceae | gi\|1158444432\|emb\|LT799971.1\| | *Clostridium* sp. Marseille-P2378 partial 16S rRNA gene, strain Marseille-P2378 |
| Lachnospiraceae | gi\|1008904189\|emb\|LT223578.1\| | *Ruminococcus* sp. Marseille-P328 partial 16S rRNA gene, strain Marseille-P328 |
| Lachnospiraceae | gi\|162949827\|gb\|EU305624.1\| | Clostridiaceae bacterium K10 16S ribosomal RNA gene, partial sequence |
| Lachnospiraceae | gi\|34558701\|gb\|AY305314.1\| | Butyrate-producing bacterium SM4/1 16S ribosomal RNA gene, partial sequence |
| Lachnospiraceae | gi\|34558696\|gb\|AY305309.1\| | Butyrate-producing bacterium M62/1 16S ribosomal RNA gene, partial sequence |
| Lachnospiraceae | gi\|1047487928\|gb\|KX356509.1\| | Lachnospiraceae bacterium KNHs209 clone 2574497994 16S ribosomal RNA gene, partial sequence |
| Lachnospiraceae | gi\|1047487919\|gb\|KX356507.1\| | Lachnospiraceae bacterium KNHs209 clone 2574499676 16S ribosomal RNA gene, partial sequence |
| Lachnospiraceae | gi\|1047487915\|gb\|KX356506.1\| | Lachnospiraceae bacterium KNHs209 clone 2574499865 16S ribosomal RNA gene, partial sequence |
| Lachnospiraceae | gi\|1154838044\|emb\|LT631543.2\| | *Blautia* sp. Marseille-P3441 partial 16S rRNA gene, strain Marseille-P3441 |
| Lachnospiraceae | gi\|1147668874\|gb\|KY621471.1\| | *Clostridium* sp. strain CS1GBYEI2 16S ribosomal RNA gene, partial sequence |
| Lachnospiraceae | gi\|1047487923\|gb\|KX356508.1\| | Lachnospiraceae bacterium KNHs209 clone 2574499031 16S ribosomal RNA gene, partial sequence |
| Lachnospiraceae | gi\|1047487911\|gb\|KX356505.1\| | Lachnospiraceae bacterium KNHs209 clone 2574501149 16S ribosomal RNA gene, partial sequence |
| Lachnospiraceae | gi\|1023747088\|gb\|KX009920.1\| | Lachnospiraceae bacterium DW22 16S ribosomal RNA gene, partial sequence |
| Lachnospiraceae | gi\|1023747086\|gb\|KX009918.1\| | Lachnospiraceae bacterium DW17 16S ribosomal RNA gene, partial sequence |
| Lachnospiraceae | gi\|1008904263\|emb\|LT223651.1\| | [*Clostridium*] *amygdalinum* partial 16S rRNA gene, strain Marseille-P2095 |
| Lachnospiraceae | gi\|1004171138\|gb\|KT889286.1\| | Bacterium 11(2016) 16S ribosomal RNA gene, partial sequence |
| Lachnospiraceae | gi\|1004171136\|gb\|KT889284.1\| | Bacterium 9(2016) 16S ribosomal RNA gene, partial sequence |

TABLE 6-continued

Responder/non-responder bacteria identified by 16S sequencing OTUs.

| Family | Subject Seq-ID | Source |
|---|---|---|
| Lachnospiraceae | gi|985742338|gb|KT633847.1| | [Clostridium] celerecrescens strain MCM B565 16S ribosomal RNA gene, partial sequence |
| Lachnospiraceae | gi|630257004|gb|KJ722511.1| | Clostridium sp. Nesulana3-1 16S ribosomal RNA gene, partial sequence |
| Lachnospiraceae | gi|630256999|gb|KJ722506.1| | Desulfotomaculum sp. Gec1-7ana4-1 16S ribosomal RNA gene, partial sequence |
| Lachnospiraceae | gi|34558709|gb|AY305322.1| | Butyrate-producing bacterium SR1/5 16S ribosomal RNA gene, partial sequence |
| Lachnospiraceae | gi|34558708|gb|AY305321.1| | Butyrate-producing bacterium SR1/1 16S ribosomal RNA gene, partial sequence |
| Lachnospiraceae | gi|73427042|gb|DQ144128.1| | Butyrate-producing bacterium PH07BW09 16S ribosomal RNA gene, partial sequence |
| Lachnospiraceae | gi|115607479|gb|DQ986224.1| | Clostridiales bacterium A2-162 16S ribosomal RNA gene, partial sequence |
| Lachnospiraceae | gi|1193829152|ref|NR_147395.1| | Blautia marasmi strain Marseille-P2377 16S ribosomal RNA, partial sequence |
| Lachnospiraceae | gi|1173534576|gb|CP015405.2| | Blautia sp. YL58, complete genome |
| Lachnospiraceae | gi|1153695771|gb|KY703632.1| | Blautia sp. strain KB1 16S ribosomal RNA gene, partial sequence |
| Lachnospiraceae | gi|1046552739|gb|KX594322.1| | Blautia coccoides strain Ga-1 16S ribosomal RNA gene, partial sequence |
| Lachnospiraceae | gi|1023747089|gb|KX009921.1| | Lachnospiraceae bacterium DW28 16S ribosomal RNA gene, partial sequence |
| Lachnospiraceae | gi|988571034|gb|KU196081.1| | Blautia coccoides strain DSM 29138 16S ribosomal RNA gene, partial sequence |
| Lachnospiraceae | gi|988570987|gb|KR364747.1| | Blautia sp. YL58 16S ribosomal RNA gene, partial sequence |
| Lachnospiraceae | gi|816399476|gb|GQ456208.2| | Blautia sp. A-C6-0 16S ribosomal RNA gene, partial sequence |
| Lachnospiraceae | gi|676402738|gb|KM043749.1| | Bacterium P1G4 16S ribosomal RNA gene, partial sequence |
| Lachnospiraceae | gi|122725186|gb|EF025906.1| | Clostridium coccoides strain 8F 16S ribosomal RNA gene, partial sequence |
| Lachnospiraceae | gi|133779805|gb|EF451052.1| | Ruminococcus sp. END-1 16S ribosomal RNA gene, partial sequence |
| Lachnospiraceae | gi|62865582|gb|AY937379.1| | Ruminococcus productus strain SECO-Mt75m3 16S ribosomal RNA gene, partial sequence |
| Lachnospiraceae | gi|55975496|gb|AY653234.1| | Ruminococcus sp. MLG080-3 16S ribosomal RNA gene, partial sequence |
| Lachnospiraceae | gi|1079701574|emb|LT623891.1| | Blautia sp. Marseille-P3201T partial 16S rRNA gene, strain Marseille-P3201T |
| Lachnospiraceae | gi|1004171139|gb|KT889287.1| | Bacterium 12(2016) 16S ribosomal RNA gene, partial sequence |
| Lachnospiraceae | gi|988570986|gb|KR364746.1| | Blautia caecimuris strain SJ18 16S ribosomal RNA gene, partial sequence |
| Verrucomicrobiaceae | gi|1173526690|gb|CP015409.2| | Akkermansia muciniphila strain YL44, complete genome |
| Verrucomicrobiaceae | gi|988570971|gb|KR364731.1| | Akkermansia muciniphila strain YL44 16S ribosomal RNA gene, partial sequence |
| Verrucomicrobiaceae | gi|343202494|ref|NR_042817.1| | Akkermansia muciniphila strain Muc 16S ribosomal RNA gene, complete sequence<>Akkermansia muciniphila strain Muc 16S ribosomal RNA gene, complete sequence |
| Verrucomicrobiaceae | gi|343200984|ref|NR_041671.1| | Haloferula rosea strain 06SJR1-1 16S ribosomal RNA gene, partial sequence<>Haloferula rosea gene for 16S rRNA, partial sequence, strain: 06SJR1-1 |
| Verrucomicrobiaceae | gi|343200983|ref|NR_041670.1| | Haloferula harenae strain YM23-227 16S ribosomal RNA gene, partial sequence<>Haloferula harenae gene for 16S rRNA, partial sequence, strain: YM23-227 |
| Verrucomicrobiaceae | gi|343200986|ref|NR_041673.1| | Haloferula helveola strain 05IJR53-1 16S ribosomal RNA gene, partial sequence<>Haloferula helveola gene for 16S rRNA, partial sequence, strain: 05IJR53-1 |
| Verrucomicrobiaceae | gi|152002650|dbj|AB331894.1| | Luteolibacter algae gene for 16S rRNA, partial sequence, strain: A5J-40 |
| Verrucomicrobiaceae | gi|343200937|ref|NR_041624.1| | Luteolibacter algae strain A5J-41-2 16S ribosomal RNA gene, partial |

TABLE 6-continued

Responder/non-responder bacteria identified by 16S sequencing OTUs.

| Family | Subject Seq-ID | Source |
|---|---|---|
| | | sequence<>*Luteolibacter algae* gene for 16S rRNA, partial sequence, strain: A5J-41-2 |
| Verrucomicrobiaceae | gi|163937810|dbj|AB372857.1| | *Haloferula sargassicola* gene for 16S rRNA, partial sequence, strain: MN1-1047 |
| Verrucomicrobiaceae | gi|343200987|ref|NR_041674.1| | *Haloferula sargassicola* strain MN1-1037 16S ribosomal RNA gene, partial sequence<>*Haloferula sargassicola* gene for 16S rRNA, partial sequence, strain: MN1-1037 |
| Verrucomicrobiaceae | gi|163929779|dbj|AB373024.1| | Verrucomicrobia bacterium MN 1-1006 gene for 16S rRNA, partial sequence |
| Verrucomicrobiaceae | gi|343200849|ref|NR_041536.1| | *Rubritalea squalenifaciens* strain HOact23 16S ribosomal RNA gene, partial sequence<>*Rubritalea squalenifaciens* gene for 16S rRNA, partial sequence |
| Verrucomicrobiaceae | gi|343200985|ref|NR_041672.1| | *Haloferula phyci* strain AK18-024 16S ribosomal RNA gene, partial sequence<>*Haloferula phyci* gene for 16S rRNA, partial sequence, strain: AK18-024 |
| Verrucomicrobiaceae | gi|343200943|ref|NR_041630.1| | *Rubritalea sabuli* strain YM29-052 16S ribosomal RNA gene, partial sequence<>*Rubritalea sabuli* gene for 16S rRNA, partial sequence |
| Verrucomicrobiaceae | gi|343200938|ref|NR_041625.1| | *Luteolibacter pohnpeiensis* strain A4T-83 16S ribosomal RNA gene, partial sequence<>*Luteolibacter pohnpeiensis* gene for 16S rRNA, partial sequence, strain: A4T-83 |
| Verrucomicrobiaceae | gi|760303835|gb|KP030837.1| | Verrucomicrobia bacterium PAORIC-16 16S ribosomal RNA gene, partial sequence |
| Verrucomicrobiaceae | gi|760303834|gb|KP030836.1| | Verrucomicrobia bacterium PAORIC-15 16S ribosomal RNA gene, partial sequence |
| Verrucomicrobiaceae | gi|152002643|dbj|AB331887.1| | *Persicirhabdus sediminis* gene for 16S rRNA, partial sequence, strain: YM21-151 |
| Verrucomicrobiaceae | gi|343200933|ref|NR_041620.1| | *Persicirhabdus sediminis* strain YM20-087 16S ribosomal RNA gene, partial sequence<>*Persicirhabdus sediminis* gene for 16S rRNA, partial sequence, strain: YM20-087 |
| Verrucomicrobiaceae | gi|164510703|emb|AJ966882.1| | *Prosthecobacter debontii* 16S rRNA gene (partial), 23 S rRNA gene (partial), tRNA-Ala gene, tRNA-Ile gene and ITS1, strain DSM 14044 |
| | gi|165929482|emb|AM932460.1| | Alpha proteobacterium Jbg30 partial 16S rRNA gene, isolate Jbg30 |
| | gi|74052580|gb|DQ167235.1| | *Brucella* sp. HJ114 16S ribosomal RNA gene, partial sequence |
| | gi|115529818|gb|DQ869302.1| | *Roseospira* sp. JL052 16S ribosomal RNA gene, partial sequence |
| | gi|1179766740|ref|NR_146690.1| | *Dongia soli* strain D78 16S ribosomal RNA, partial sequence |
| | gi|760303826|gb|KP030828.1| | Alpha proteobacterium SAORIC-614 16S ribosomal RNA gene, partial sequence |
| | gi|165929480|emb|AM932458.1| | Alpha proteobacterium Jbg28 partial 16S rRNA gene, isolate Jbg28 |
| | gi|343205857|ref|NR_044315.1| | *Insolitispirillum peregrinum* subsp. *integrum* strain LMG 5407 16S ribosomal RNA gene, partial sequence<>*Aquaspirillum peregrinum* subsp. *integrum* strain LMG 5407 16S ribosomal RNA gene, partial sequence |
| | gi|343205856|ref|NR_044314.1| | *Insolitispirillum peregrinum* strain LMG 4340 16S ribosomal RNA gene, partial sequence<>*Aquaspirillum peregrinum* subsp. *peregrinum* strain LMG 4340 16S ribosomal RNA gene, partial sequence |
| | gi|111185844|emb|AM180478.1| | *Rhodospirillum* sp. C2T-PP-R1 partial 16S rRNA gene, isolate C2T-PP-R1 |

TABLE 6-continued

Responder/non-responder bacteria identified by 16S sequencing OTUs.

| Family | Subject Seq-ID | Source |
|---|---|---|
| | gi\|729042038\|emb\|LN650457.1\| | *Novispirillum itersonii* partial 16S rRNA gene, isolate TOSS-106 |
| | gi\|156968444\|gb\|EF616604.1\| | Bacterium HTCC8037 16S ribosomal RNA gene, partial sequence |
| | gi\|148509101\|gb\|EF587969.1\| | Alpha proteobacterium UST061013-025 16S ribosomal RNA gene, partial sequence |
| | gi\|343200914\|ref\|NR_041601.1\| | *Tanticharoenia sakaeratensis* strain NBRC 103193 16S ribosomal RNA gene, partial sequences<>*Tanticharoenia sakaeratensis* gene for 16S ribosomal RNA, partial sequence, strain: NBRC 103193<>*Tanticharoenia sakaeratensis* gene for 16S ribosomal RNA, partial sequence, strain: NBRC 103194<>*Tanticharoenia sakaeratensis* gene for 16S ribosomal RNA, partial sequence, strain: NBRC 103195 |
| | gi\|157170576\|emb\|AM411930.1\| | Alpha proteobacterium P-20 partial 16S rRNA gene, strain P-20 |
| | gi\|157170575\|emb\|AM411929.1\| | Alpha proteobacterium P-4 partial 16S rRNA gene, strain P-4 |
| | gi\|37905460\|gb\|AY225460.1\| | Acetobacteraceae bacterium SASB-15 16S ribosomal RNA gene, partial sequence |
| | gi\|37905426\|gb\|AY225458.1\| | Acetobacteraceae bacterium SASB-2 16S ribosomal RNA gene, partial sequence<>Acetobacteraceae bacterium SASB-4 16S ribosomal RNA gene, partial sequence |
| | gi\|1018583283\|gb\|KU865461.1\| | *Candidatus Neoehrlichia arcana* isolate HT136 16S ribosomal RNA gene, partial sequence |
| | gi\|1015829900\|gb\|KT946836.1\| | *Gluconobacter oxydans* strain G-1 16S ribosomal RNA gene, partial sequence |
| | gi\|1005742402\|gb\|KT283053.1\| | *Acetobacter pasteurianus* strain DY-5 16S ribosomal RNA gene, partial sequence |
| Erysipelotrichaceae | gi\|988571035\|gb\|KU196082.1\| | *Erysipelatoclostridium ramosum* strain DSM 29355 16S ribosomal RNA gene, partial sequence |
| Erysipelotrichaceae | gi\|988570994\|gb\|KR364754.1\| | *Erysipelatoclostridium ramosum* strain SRB509-5-F-B 16S ribosomal RNA gene, partial sequence |
| Erysipelotrichaceae | gi\|631252045\|ref\|NR_113243.1\| | *Erysipelatoclostridium ramosum* strain JCM 1298 16S ribosomal RNA gene, partial sequences *Clostridium ramosum* gene for 16S ribosomal RNA, partial sequence, strain: JCM 1298<>*Clostridium ramosum* gene for 16S ribosomal RNA, partial sequence, strain: JCM 5235<>*Clostridium ramosum* gene for 16S ribosomal RNA, partial sequence, strain: JCM 5234 |
| Erysipelotrichaceae | gi\|645322231\|ref\|NR_119030.1\| | [*Clostridium*] *spiroforme* strain DSM 1552 16S ribosomal RNA gene, complete sequence |
| Erysipelotrichaceae | gi\|631253195\|ref\|NR_114393.1\| | [*Clostridium*] *spiroforme* strain JCM 1432 16S ribosomal RNA gene, partial sequence<>*Clostridium spiroforme* gene for 16S ribosomal RNA, partial sequence, strain: JCM 1432 |
| Erysipelotrichaceae | gi\|51512137\|gb\|AY699288.1\| | *Clostridium ramosum* isolate M91 16S ribosomal RNA gene, partial sequence |
| Erysipelotrichaceae | gi\|752910213\|emb\|LN713275.1\| | Clostridiaceae bacterium GM1 partial 16S rRNA gene, strain GM1 |
| Erysipelotrichaceae | gi\|1187200865\|gb\|KY992931.1\| | *Erysipelatoclostridium* sp. SNUG30099 16S ribosomal RNA gene, partial sequence |
| Erysipelotrichaceae | gi\|1187200864\|gb\|KY992930.1\| | *Erysipelatoclostridium* sp. SNUG30370 16S ribosomal RNA gene, partial sequence |
| Erysipelotrichaceae | gi\|988571005\|gb\|KR364765.1\| | *Longibaculum muris* strain MT10-315-CC-1.2-2 16S ribosomal RNA gene, partial sequence |

TABLE 6-continued

Responder/non-responder bacteria identified by 16S sequencing OTUs.

| Family | Subject Seq-ID | Source |
| --- | --- | --- |
| Erysipelotrichaceae | gi\|647404815\|emb\|LK021123.1\| | Bacterium LF-3 partial 16S rRNA gene, isolate LF-3 |
| Erysipelotrichaceae | gi\|1179666511\|dbj\|LC258136.1\| | *Sharpea azabuensis* gene for 16S ribosomal RNA, partial sequence, strain: JCM 14210 |
| Erysipelotrichaceae | gi\|121544027\|gb\|AY265465.2\| | Bovine rumen bacterium niuD2 16S ribosomal RNA gene, complete sequence |
| Erysipelotrichaceae | gi\|121544026\|gb\|AY265464.2\| | Bovine rumen bacterium niuC23 16S ribosomal RNA gene, complete sequence |
| Erysipelotrichaceae | gi\|121544025\|gb\|AY263508.2\| | Bovine rumen bacterium niuO28 16S ribosomal RNA gene, complete sequence |
| Erysipelotrichaceae | gi\|121544024\|gb\|AY263507.2\| | Bovine rumen bacterium niuO25 16S ribosomal RNA gene, complete sequence |
| Erysipelotrichaceae | gi\|121544023\|gb\|AY263506.2\| | Bovine rumen bacterium niuO17 16S ribosomal RNA gene, complete sequence |
| Erysipelotrichaceae | gi\|121544022\|gb\|AY263505.2\| | Bovine rumen bacterium SNU-NiuO16 16S ribosomal RNA gene, complete sequence |
| Erysipelotrichaceae | gi\|121544021\|gb\|AY263503.2\| | Bovine rumen bacterium niuO6 16S ribosomal RNA gene, complete sequence |
| Erysipelotrichaceae | gi\|121544020\|gb\|AY263502.2\| | Bovine rumen bacterium niuD4 16S ribosomal RNA gene, complete sequence |
| Coriobacteriaceae | gi\|1179666521\|dbj\|LC258146.1\| | *Collinsella aerofaciens* gene for 16S ribosomal RNA, partial sequence, strain: JCM 10808 |
| Coriobacteriaceae | gi\|1179666520\|dbj\|LC258145.1\| | *Collinsella aerofaciens* gene for 16S ribosomal RNA, partial sequence, strain: JCM 10803 |
| Coriobacteriaceae | gi\|1179666519\|dbj\|LC258144.1\| | *Collinsella aerofaciens* gene for 16S ribosomal RNA, partial sequence, strain: JCM 10800 |
| Coriobacteriaceae | gi\|1179666518\|dbj\|LC258143.1\| | *Collinsella aerofaciens* gene for 16S ribosomal RNA, partial sequence, strain: JCM 10799 |
| Coriobacteriaceae | gi\|1179666517\|dbj\|LC258142.1\| | *Collinsella aerofaciens* gene for 16S ribosomal RNA, partial sequence, strain: JCM 10798 |
| Coriobacteriaceae | gi\|1179666516\|dbj\|LC258141.1 | *Collinsella aerofaciens* gene for 16S ribosomal RNA, partial sequence, strain: JCM 10797 |
| Coriobacteriaceae | gi\|1179666515\|dbj\|LC258140.1\| | *Collinsella aerofaciens* gene for 16S ribosomal RNA, partial sequence, strain: JCM 10795 |
| Coriobacteriaceae | gi\|1179666514\|dbj\|LC258139.1\| | *Collinsella aerofaciens* gene for 16S ribosomal RNA, partial sequence, strain: JCM 10794 |
| Coriobacteriaceae | gi\|1179666513\|dbj\|LC258138.1\| | *Collinsella aerofaciens* gene for 16S ribosomal RNA, partial sequence, strain: JCM 10793 |
| Coriobacteriaceae | gi\|1024389107\|emb\|LT558813.1\| | *Collinsella aerofaciens* partial 16S rRNA gene, strain Marseille-P1069 |
| Coriobacteriaceae | gi\|1008904268\|emb\|LT223656.1\| | *Collinsella aerofaciens* partial 16S rRNA gene, strain Marseille-P1069 |
| Coriobacteriaceae | gi\|745628439\|gb\|KP233454.1\| | *Collinsella aerofaciens* strain D9-82 16S ribosomal RNA gene, partial sequence |
| Coriobacteriaceae | gi\|745628433\|gb\|KP233448.1\| | *Collinsella aerofaciens* strain D9-111 16S ribosomal RNA gene, partial sequence<>*Collinsella aerofaciens* strain D9-136 16S ribosomal RNA gene, partial sequence |
| Coriobacteriaceae | gi\|745628432\|gb\|KP233447.1\| | *Collinsella aerofaciens* strain D9-108 16S ribosomal RNA gene, partial sequence |
| Coriobacteriaceae | gi\|745628431\|gb\|KP233446.1\| | *Collinsella aerofaciens* strain D9-101 16S ribosomal RNA gene, partial sequence<>*Collinsella aerofaciens* strain D9-76 16S ribosomal RNA gene, partial sequence |
| Coriobacteriaceae | gi\|745628430\|gb\|KP233445.1\| | *Collinsella aerofaciens* strain D8-75 16S ribosomal RNA gene, partial sequence |
| Coriobacteriaceae | gi\|745628429\|gb\|KP233444.1\| | *Collinsella aerofaciens* strain D8-61 16S ribosomal RNA gene, partial sequence |
| Coriobacteriaceae | gi\|745628428\|gb\|KP233443.1\| | *Collinsella aerofaciens* strain D8-40 16S ribosomal RNA gene, partial sequence |
| Coriobacteriaceae | gi\|745628427\|gb\|KP233442.1\| | *Collinsella aerofaciens* strain D8-146 16S ribosomal RNA gene, partial sequence |

TABLE 6-continued

Responder/non-responder bacteria identified by 16S sequencing OTUs.

| Family | Subject Seq-ID | Source |
|---|---|---|
| Coriobacteriaceae | gi|745628426|gb|KP233441.1| | *Collinsella aerofaciens* strain D8-124 16S ribosomal RNA gene, partial sequence |
| | gi|1023747096|gb|KX009928.1| | Lachnospiraceae bacterium DW60 16S ribosomal RNA gene, partial sequence |
| | gi|743404488|emb|LN626356.1| | *Herbinix* sp. RK1P partial 16S rRNA gene, isolate RK1P |
| | gi|743404487|emb|LN626357.1| | *Herbinix* sp. SD1I partial 16S rRNA gene, isolate SD1I |
| | gi|743404486|emb|LN626358.1| | *Herbinix* sp. SD1G partial 16S rRNA gene, isolate SD1G |
| | gi|743404485|emb|LN626359.1| | *Herbinix* sp. SD1D partial 16S rRNA gene, isolate SD1D |
| | gi|1040567056|ref|NR_137405.1| | *Anaerobium acetethylicum* strain GluBS11 16S ribosomal RNA, partial sequence<>*Anaerobium acetethylicum* strain GluBS11 16S ribosomal RNA gene, partial sequence |
| | gi|1024974678|ref|NR_136763.1| | *Herbinix hemicellulosilytica* strain T3/55 16S ribosomal RNA, partial sequence<>*Herbinix hemicellulosilytica* partial 16S rRNA gene, isolate T3/55 |
| | gi|605097974|gb|KJ016028.1| | *Clostridium* sp. Pao32 16S ribosomal RNA gene, partial sequence |
| | gi|166063939|dbj|AB298768.2| | *Anaerotaenia torta* gene for 16S rRNA, partial sequence |
| | gi|343202586|ref|NR_042953.1| | *Anaerosporobacter mobilis* strain IMSNU 40011 16S ribosomal RNA gene, partial sequence |
| | gi|775444676|emb|LN794845.1| | *Lachnotalea glycerini* partial 16S rRNA gene, type strain DLD10T |
| | gi|664616078|emb|LK391571.1| | Lachnospiraceae bacterium V37_10_1 partial 16S rRNA gene, isolate V37_10_1 |
| | gi|664616076|emb|LK391569.1| | Lachnospiraceae bacterium V37_06_2 partial 16S rRNA gene, isolate V37_06_2 |
| | gi|664616071|emb|LK391564.1| | Lachnospiraceae bacterium V37_02_2 partial 16S rRNA gene, isolate V37_02_2 |
| | gi|160426828|gb|CP000885.1| | *Clostridium phytofermentans* ISDg, complete genome |
| | gi|751868028|dbj|LC020504.1| | *Clostridium* sp. TB5 gene for 16S ribosomal RNA, partial sequence |
| | gi|664616057|emb|LK391550.1| | Lachnospiraceae bacterium S37_06_2 partial 16S rRNA gene, isolate S37_06_2 |
| | gi|343198925|ref|NR_044049.1| | *Coprococcus entactus* strain ATCC 27759 16S ribosomal RNA gene, partial sequence<>*Coprococcus eutactus* strain ATCC 27759 16S ribosomal RNA gene, partial sequence |
| | gi|2258201|gb|U68616.1|UEU68616 | Unidentified eubacterium from the Amazon 16S ribosomal RNA gene, partial sequence |
| | gi|37993572|gb|AY350746.1| | Butyrate-producing bacterium ART55/1 16S ribosomal RNA gene, partial sequence |
| Ruminococcaceae | gi|820661309|emb|LN846907.1| | *Clostridium* sp. GD3 partial 16S rRNA gene, strain GD3 |
| Ruminococcaceae | gi|806475686|gb|KP114242.1| | *Intestinimonas* sp. FSAA-17 16S ribosomal RNA gene, partial sequence |
| Ruminococcaceae | gi|676402756|gb|KM043767.1| | Bacterium P1D11 16S ribosomal RNA gene, partial sequence |
| Ruminococcaceae | gi|1193829127|ref|NR_147370.1| | *Pseudoflavonifractor phocaeensis* strain Marseille-P3064 16S ribosomal RNA, partial sequence |
| Ruminococcaceae | gi|1173509597|gb|CP015406.2| | *Flavonifractor plautii* strain YL31, complete genome |
| Ruminococcaceae | gi|1150560357|dbj|LC175305.1| | *Clostridium* sp. 19-20 gene for 16S ribosomal RNA, partial sequence, isolate: 19-20 |
| Ruminococcaceae | gi|988571039|gb|KU196086.1| | *Flavonifractor plautii* strain DSM 29136 16S ribosomal RNA gene, partial sequence |
| Ruminococcaceae | gi|988571013|gb|KR364773.1| | *Flavonifractor plautii* strain YL31 16S ribosomal RNA gene, partial sequence |
| Ruminococcaceae | gi|988571012|gb|KR364772.1| | *Flavonifractor plautii* strain mOs-SRB-10A-2011 16S ribosomal RNA gene, partial sequence |

TABLE 6-continued

Responder/non-responder bacteria identified by 16S sequencing OTUs.

| Family | Subject Seq-ID | Source |
|---|---|---|
| Ruminococcaceae | gi|343198636|ref|NR_043142.1| | *Flavonifractor plautii* strain Prevot S1 16S ribosomal RNA gene, partial sequence<>*Eubacterium plautii* strain CCUG 28093 16S ribosomal RNA gene, partial sequence<>Uncultured bacterium clone CFT19A5 16S ribosomal RNA gene, partial sequence |
| Ruminococcaceae | gi|52355230|gb|AY730665.1| | *Clostridium orbiscindens* strain NML 01-A-077 16S ribosomal RNA gene, partial sequence |
| Ruminococcaceae | gi|52355229|gb|AY730664.1| | *Clostridium orbiscindens* strain NML 00-A-095 16S ribosomal RNA gene, partial sequence |
| Ruminococcaceae | gi|52355228|gb|AY730663.1| | *Clostridium orbiscindens* strain NML 00-A-082 16S ribosomal RNA gene, partial sequence |
| Ruminococcaceae | gi|52355227|gb|AY730662.1| | *Clostridium orbiscindens* strain NML 98-A-029 16S ribosomal RNA gene, partial sequence |
| Ruminococcaceae | gi|676402757|gb|KM043768.1| | Bacterium P2C2 16S ribosomal RNA gene, partial sequence |
| Ruminococcaceae | gi|219846080|ref|NR_025670.1| | *Pseudoflavonifractor capillosus* strain ATCC 29799 16S ribosomal RNA gene, partial sequence<>*Bacteroides capillosus* 16S ribosomal RNA gene, partial sequence |
| Ruminococcaceae | gi|676402750|gb|KM043761.1| | Bacterium P1C2 16S ribosomal RNA gene, partial sequence |
| Ruminococcaceae | gi|50982374|gb|AY654967.1| | Unidentified bacterium clone CCCM81 16S ribosomal RNA gene, partial sequence |
| Ruminococcaceae | gi|1193829132|ref|NR_147375.1| | *Colidextribacter massiliensis* strain Marseille-P3083 16S ribosomal RNA, partial sequence |
| Ruminococcaceae | gi|676402755|gb|KM043766.1| | Bacterium P2G6 16S ribosomal RNA gene, partial sequence |
| Lachnospiraceae | gi|775444730|emb|LN828944.1| | Ruminococcaceae bacterium GD1 partial 16S rRNA gene, strain GD1 |
| Lachnospiraceae | gi|676402759|gb|KM043770.1| | Bacterium P1A6 16S ribosomal RNA gene, partial sequence |
| Lachnospiraceae | gi|50982382|gb|AY654975.1| | Unidentified bacterium clone CDDN44 16S ribosomal RNA gene, partial sequence |
| Lachnospiraceae | gi|50982361|gb|AY654954.1| | Unidentified bacterium clone CCCM52 16S ribosomal RNA gene, partial sequence |
| Lachnospiraceae | gi|50982365|gb|AY654958.1| | Unidentified bacterium clone CCCM58 16S ribosomal RNA gene, partial sequence |
| Lachnospiraceae | gi|747220154|gb|KC331157.2| | Lachnospiraceae bacterium BTY6 16S ribosomal RNA gene, partial sequence |
| Lachnospiraceae | gi|50982356|gb|AY654949.1| | Unidentified bacterium clone CCCM15 16S ribosomal RNA gene, partial sequence |
| Lachnospiraceae | gi|1008904264|emb|LT223652.1| | [*Clostridium*] *lavalense* partial 16S rRNA gene, strain Marseille-P2117 |
| Lachnospiraceae | gi|50982373|gb|AY654966.1| | Unidentified bacterium clone CCCM79 16S ribosomal RNA gene, partial sequence |
| Lachnospiraceae | gi|1023747088|gb|KX009920.1| | Lachnospiraceae bacterium DW22 16S ribosomal RNA gene, partial sequence |
| Lachnospiraceae | gi|631251356|ref|NR_112553.1| | [*Clostridium*] *glycyrrhizinilyticum* strain ZM35 16S ribosomal RNA gene, complete sequence<>*Clostridium glycyrhizinilyticum* gene for 16S ribosomal RNA |
| Lachnospiraceae | gi|1193829163|ref|NR_147406.1| | *Mordavella massiliensis* strain Marseille-P3246 16S ribosomal RNA, partial sequence |
| Lachnospiraceae | gi|1173536882|gb|CP015399.2| | *Lachnoclostridium* sp. YL32, complete genome |
| Lachnospiraceae | gi|983963892|gb|KU569989.1| | *Clostridium* sp. V1 16S ribosomal RNA gene, partial sequence |
| Lachnospiraceae | gi|1008904250|emb|LT223638.1| | *Bacteroides xylanolyticus* partial 16S rRNA gene, strain Marseille-P2455 |

TABLE 6-continued

Responder/non-responder bacteria identified by 16S sequencing OTUs.

| Family | Subject Seq-ID | Source |
| --- | --- | --- |
| Lachnospiraceae | gi\|1005925626\|emb\|LT161895.1\| | *Clostridium* sp. Marseille-P2415T partial 16S rRNA gene, type strain Marseille-P2415T |
| Lachnospiraceae | gi\|988570995\|gb\|KR364755.1\| | *Clostridium* sp. MT10-315-CC-82 16S ribosomal RNA gene, partial sequence |
| Lachnospiraceae | gi\|988570990\|gb\|KR364750.1\| | [*Clostridium*] *clostridioforme* strain YL32 16S ribosomal RNA gene, partial sequence |
| Lachnospiraceae | gi\|985742343\|gb\|KT633852.1\| | *Bacteroides xylanolyticus* strain MCM B570 16S ribosomal RNA gene, partial sequence |
| Lachnospiraceae | gi\|985742341\|gb\|KT633850.1\| | *Bacteroides xylanolyticus* strain MCM B568 16S ribosomal RNA gene, partial sequence |
| Enterobacteriaceae | gi\|1158626387\|gb\|KX929840.1\| | *Klebsiella pneumoniae* strain GPKP 16S ribosomal RNA gene, partial sequence |
| Enterobacteriaceae | gi\|1158622117\|gb\|KX377574.1\| | *Enterobacter* sp. strain YM29 16S ribosomal RNA gene, partial sequence |
| Enterobacteriaceae | gi\|1158499421\|gb\|KY750246.1\| | *Klebsiella* sp. strain QIUP 1 16S ribosomal RNA gene, partial sequence |
| Enterobacteriaceae | gi\|1154259114\|gb\|KY595448.1\| | *Enterobacter cloacae* strain S12 16S ribosomal RNA gene, partial sequence |
| Enterobacteriaceae | gi\|1154259110\|gb\|KY595444.1\| | *Enterobacter hormaechei* strain M55B 16S ribosomal RNA gene, partial sequence |
| Enterobacteriaceae | gi\|1062337936\|gb\|KX817276.1\| | *Enterobacter cloacae* strain AA4 16S ribosomal RNA gene, partial sequence |
| Enterobacteriaceae | gi\|1062327603\|gb\|KX817271.1\| | *Enterobacter* sp. strain AA25 16S ribosomal RNA gene, partial sequence |
| Enterobacteriaceae | gi\|1062327580\|gb\|KX817248.1\| | *Enterobacter* sp. strain AA13 16S ribosomal RNA gene, partial sequence |
| Enterobacteriaceae | gi\|1039023274\|gb\|KU744864.1\| | *Enterobacter* sp. SFSA65 16S ribosomal RNA gene, partial sequence |
| Enterobacteriaceae | gi\|1015522084\|gb\|KU923368.1\| | *Enterobacter cloacae* strain UBGSS3 16S ribosomal RNA gene, partial sequence |
| Enterobacteriaceae | gi\|1015522081\|gb\|KU923365.1\| | *Enterobacter cancerogenus* strain TBGSS4 16S ribosomal RNA gene, partial sequence |
| Enterobacteriaceae | gi\|1015522079\|gb\|KU923363.1\| | *Bacillus andreesenii* strain TBGSS2 16S ribosomal RNA gene, partial sequence |
| Enterobacteriaceae | gi\|1015522063\|gb\|KU923347.1\| | *Erwinia persicina* strain USTRW7 16S ribosomal RNA gene, partial sequence |
| Enterobacteriaceae | gi\|1153684959\|gb\|KY706100.1\| | *Klebsiella pneumoniae* strain NGR/A/2016 16S ribosomal RNA gene, partial sequence |
| Enterobacteriaceae | gi\|1151099307\|gb\|KY684230.1\| | *Enterobacter* sp. strain FYP1101 16S ribosomal RNA gene, partial sequence |
| Enterobacteriaceae | gi\|1158824263\|gb\|CP018785.1\| | *Enterobacter cloacae* strain AA4, complete genome |
| Enterobacteriaceae | gi\|1151331582\|gb\|KY476172.1\| | *Pantoea* sp. strain FA1-263 16S ribosomal RNA gene, partial sequence |
| Enterobacteriaceae | gi\|1151331579\|gb\|KY476169.1\| | *Enterobacter* sp. strain FA1-153 16S ribosomal RNA gene, partial sequence |
| Enterobacteriaceae | gi\|1151124876\|gb\|KX709881.1\| | *Lelliottia* sp. strain FOL02 16S ribosomal RNA gene, partial sequence |
| Enterobacteriaceae | gi\|1150318051\|gb\|KY673185.1\| | *Enterobacter* sp. strain MF90 16S ribosomal RNA gene, partial sequence |
| Lactobacillaceae | gi\|770114072\|gb\|KP178095.1\| | *Lactobacillus ruminis* strain 1313_A06 16S ribosomal RNA gene, partial sequence |
| Lactobacillaceae | gi\|770114071\|gb\|KP178094.1\| | *Lactobacillus ruminis* strain 1292_G05 16S ribosomal RNA gene, partial sequence |
| Lactobacillaceae | gi\|756130194\|gb\|KP159619.1\| | *Lactobacillus ruminis* strain CCFM8418 16S ribosomal RNA gene, partial sequence |
| Lactobacillaceae | gi\|756130193\|gb\|KP159618.1\| | *Lactobacillus ruminis* strain CCFM8417 16S ribosomal RNA gene, partial sequence |
| Lactobacillaceae | gi\|723451374\|gb\|KM269714.1\| | *Lactobacillus ruminis* strain 1291(LBF2)H02 16S ribosomal RNA gene, partial sequence |
| Lactobacillaceae | gi\|343200924\|ref\|NR_041611.1\| | *Lactobacillus ruminis* strain NBRC 102161 16S ribosomal RNA gene, partial sequence<>*Lactobacillus ruminis* gene |

TABLE 6-continued

Responder/non-responder bacteria identified by 16S sequencing OTUs.

| Family | Subject Seq-ID | Source |
|---|---|---|
| | | for 16S rRNA, partial sequence, strain: NBRC 102161 |
| Lactobacillaceae | gi|1008904203|emb|LT223591.1| | *Lactobacillus ruminis* partial 16S rRNA gene, strain Marseille-P908 |
| Lactobacillaceae | gi|1185965445|dbj|LC259012.1| | *Lactobacillus* sp. C-1 gene for 16S ribosomal RNA, partial sequence |
| Lactobacillaceae | gi|1062982723|gb|KX826967.1| | *Lactobacillus ruminis* strain M1/34 16S ribosomal RNA gene, partial sequence |
| Lactobacillaceae | gi|723451366|gb|KM269706.1| | *Lactobacillus* sp. 1280(LBF2)G02 16S ribosomal RNA gene, partial sequence |
| Lactobacillaceae | gi|937352297|gb|KP317728.1| | *Lactobacillus salivarius* strain L64 16S ribosomal RNA gene, partial sequence |
| Lactobacillaceae | gi|937352294|gb|KP317725.1| | *Lactobacillus salivarius* strain L61 16S ribosomal RNA gene, partial sequence |
| Lactobacillaceae | gi|937352288|gb|KP317719.1| | *Lactobacillus salivarius* strain L52 16S ribosomal RNA gene, partial sequence |
| Lactobacillaceae | gi|937352253|gb|KP317685.1| | *Lactobacillus salivarius* strain L14 16S ribosomal RNA gene, partial sequence |
| Lactobacillaceae | gi|937352252|gb|KP317684.1| | *Lactobacillus salivarius* strain L13 16S ribosomal RNA gene, partial sequence |
| Lactobacillaceae | gi|937352251|gb|KP317683.1| | *Lactobacillus salivarius* strain L12 16S ribosomal RNA gene, partial sequence |
| Lactobacillaceae | gi|937352249|gb|KP317681.1| | *Lactobacillus salivarius* strain L8 16S ribosomal RNA gene, partial sequence |
| Lactobacillaceae | gi|937352247|gb|KP317679.1| | *Lactobacillus salivarius* strain L6 16S ribosomal RNA gene, partial sequence |
| Lactobacillaceae | gi|937352246|gb|KP317678.1| | *Lactobacillus salivarius* strain L5 16S ribosomal RNA gene, partial sequence |
| Lactobacillaceae | gi|1024252056|gb|KU163336.1| | *Lactobacillus* sp. YANG-11 16S ribosomal RNA gene, partial sequence |

REFERENCES

The following references, some of which are cited above by number, as herein incorporated by reference in theior entireties.

1A. J. G. Caporaso et al., Ultra-high-throughput microbial community analysis on the Illumina HiSeq and MiSeq platforms. The ISME journal 6, 1621-1624 (2012). 1. S. L. Topalian et al., Safety, activity, and immune correlates of anti-PD-1 antibody in cancer. The New England journal of medicine 366, 2443-2454 (2012).

2A. C. Robert et al., Pembrolizumab versus Ipilimumab in Advanced Melanoma. The New England journal of medicine 372, 2521-2532 (2015).

3A. A. Sivan et al., Commensal *Bifidobacterium* promotes antitumor immunity and facilitates anti-PD-L1 efficacy. Science 350, 1084-1089 (2015).

4A. R. Daillere et al., *Enterococcus hirae* and *Barnesiella intestinihominis* Facilitate Cyclophosphamide-Induced Therapeutic Immunomodulatory Effects. Immunity 45, 931-943 (2016).

5A. N. Iida et al., Commensal bacteria control cancer response to therapy by modulating the tumor microenvironment. Science (New York, N.Y.) 342, 967-970 (2013).

6A. K. Atarashi et al., Induction of colonic regulatory T cells by indigenous *Clostridium* species. Science (New York, N.Y.) 331, 337-341 (2011).

7A. J. L. Round, S. K. Mazmanian, Inducible Foxp3+ regulatory T-cell development by a commensal bacterium of the intestinal microbiota. Proceedings of the National Academy of Sciences of the United States of America 107, 12204-12209 (2010).

8A. N. Geva-Zatorsky et al., Mining the Human Gut Microbiota for Immunomodulatory Organisms. Cell 168, 928-943 e911 (2017).

9A. J. G. Caporaso et al., Ultra-high-throughput microbial community analysis on the Illumina HiSeq and MiSeq platforms. The ISME journal 6, 1621-1624 (2012).

10A. J. G. Caporaso et al., Global patterns of 16S rRNA diversity at a depth of millions of sequences per sample. Proceedings of the National Academy of Sciences of the United States of America 108 Suppl 1, 4516-4522 (2011).

11A. J. G. Caporaso et al., QIIME allows analysis of high-throughput community sequencing data. Nat Methods 7, 335-336 (2010).

12A. D. McDonald et al., An improved Greengenes taxonomy with explicit ranks for ecological and evolutionary analyses of bacteria and archaea. ISME J 6, 610-618 (2012).

13A. J. G. Caporaso et al., PyNAST: a flexible tool for aligning sequences to a template alignment. Bioinformatics 26, 266-267 (2010).

14A. Q. Wang, G. M. Garrity, J. M. Tiedje, J. R. Cole, Naive Bayesian classifier for rapid assignment of rRNA sequences into the new bacterial taxonomy. Appl Environ Microbiol 73, 5261-5267 (2007).

15A. N. Segata et al., Metagenomic microbial community profiling using unique clade-specific marker genes. Nat Methods 9, 811-814 (2012).

16A. C. Human Microbiome Project, A framework for human microbiome research. Nature 486, 215-221 (2012).

17A. M. C. Collado, M. Derrien, E. Isolauri, W. M. de Vos, S. Salminen, Intestinal integrity and *Akkermansia muciniphila*, a mucin-degrading member of the intestinal microbiota present in infants, adults, and the elderly. Applied and environmental microbiology 73, 7767-7770 (2007).

18A. J. Junick, M. Blaut, Quantification of human fecal *bifidobacterium* species by use of quantitative real-time PCR analysis targeting the groEL gene. Applied and environmental microbiology 78, 2613-2622 (2012).

19A. E. Malinen, A. Kassinen, T. Rinttila, A. Palva, Comparison of real-time PCR with SYBR Green I or 5'-nuclease assays and dot-blot hybridization with rDNA-targeted oligonucleotide probes in quantification of selected faecal bacteria. Microbiology (Reading, England) 149, 269-277 (2003).

20A. T. Matsuki, K. Watanabe, R. Tanaka, H. Oyaizu, Rapid identification of human intestinal bifidobacteria by 16S rRNA-targeted species- and group-specific primers. FEMS microbiology letters 167, 113-121 (1998).

21A. A. Kassinen et al., The fecal microbiota of irritable bowel syndrome patients differs significantly from that of healthy subjects. Gastroenterology 133, 24-33 (2007).

22A. I. U. Rathnayake, M. Hargreaves, F. Huygens, Genotyping of *Enterococcus faecalis* and *Enterococcus faecium* isolates by use of a set of eight single nucleotide polymorphisms. Journal of clinical microbiology 49, 367-372 (2011).

23A. T. Rinttila, A. Kassinen, E. Malinen, L. Krogius, A. Palva, Development of an extensive set of 16S rDNA-targeted primers for quantification of pathogenic and indigenous bacteria in faecal samples by real-time PCR. Journal of applied microbiology 97, 1166-1177 (2004).

24A. Z. Sun et al., Locked nucleic acid pentamers as universal PCR primers for genomic DNA amplification. PloS one 3, e3701 (2008).

25A. K. Matsuda et al., Establishment of an analytical system for the human fecal microbiota, based on reverse transcription-quantitative PCR targeting of multicopy rRNA molecules. Applied and environmental microbiology 75, 1961-1969 (2009).

26A. P. Louis, S. I. McCrae, C. Charrier, H. J. Flint, Organization of butyrate synthetic genes in human colonic bacteria: phylogenetic conservation and horizontal gene transfer. FEMS microbiology letters 269, 240-247 (2007).

27A. X. W. Huijsdens et al., Quantification of bacteria adherent to gastrointestinal mucosa by real-time PCR. Journal of clinical microbiology 40, 4423-4427 (2002).

28A. J. Tong, C. Liu, P. Summanen, H. Xu, S. M. Finegold, Application of quantitative real-time PCR for rapid identification of *Bacteroides fragilis* group and related organisms in human wound samples. Anaerobe 17, 64-68 (2011).

29A. H. Yampara-Iquise, G. Zheng, J. E. Jones, C. A. Carson, Use of a *Bacteroides* thetaiotaomicron-specific alpha-1-6, mannanase quantitative PCR to detect human faecal pollution in water. Journal of applied microbiology 105, 1686-1693 (2008).

30A. S. J. Song et al., Cohabiting family members share microbiota with one another and with their dogs. Elife 2, e00458 (2013).

31A. C. G. Buffie et al., Profound alterations of intestinal microbiota following a single dose of clindamycin results in sustained susceptibility to *Clostridium difficile*-induced colitis. Infect Immun 80, 62-73 (2012).

32A. S. Andrews, FastQC: A quality control application for high throughput sequence data. Babraham Institute. Project page: http://www.bioinformatics.babraham.ac.uk/projects/fastqc, (2016).

33A. N. L. Bray, H. Pimentel, P. Melsted, L. Pachter, Near-optimal probabilistic RNA-seq quantification. Nature biotechnology 34, 525-527 (2016).

34A. C. Soneson, M. I. Love, M. D. Robinson, Differential analyses for RNA-seq: transcript-level estimates improve gene-level inferences. F1000Res 4, 1521 (2015).

35A. H. Li, Aligning sequence reads, clone sequences and assembly contigs with BWA-MEM. arXiv:1303.3997v2 [q-bio.GN], (2013).

36A. A. Tarasov, A. J. Vilella, E. Cuppen, I. J. Nijman, P. Prins, Sambamba: fast processing of NGS alignment formats. Bioinformatics 31, 2032-2034 (2015).

37A. G. A. Van der Auwera et al., From FastQ data to high confidence variant calls: the Genome Analysis Toolkit best practices pipeline. Curr Protoc Bioinformatics 43, 11 10 11-33 (2013).

38A. K. Cibulskis et al., Sensitive detection of somatic point mutations in impure and heterogeneous cancer samples. Nature biotechnology 31, 213-219 (2013).

39A. C. Genomes Project et al., A global reference for human genetic variation. Nature 526, 68-74 (2015).

40A. W. Fu et al., Analysis of 6,515 exomes reveals the recent origin of most human protein-coding variants. Nature 493, 216-220 (2013).

41A. M. Lek et al., Analysis of protein-coding genetic variation in 60,706 humans. Nature 536, 285-291 (2016).

42. K. Wang, M. Li, H. Hakonarson, ANNOVAR: functional annotation of genetic variants from high-throughput sequencing data. Nucleic Acids Res 38, e164 (2010).

43A. C. Blank et al., PD-L1/B7H-1 inhibits the effector phase of tumor rejection by T cell receptor (TCR) transgenic CD8+ T cells. Cancer research 64, 1140-1145 (2004).

44A. Y. Benjamini, Y. Hochberg, Controlling the False Discovery Rate—a Practical and Powerful Approach to Multiple Testing. J Roy Stat Soc B Met 57, 289-300 (1995).

1B. S. L. Topalian et al., Safety, activity, and immune correlates of anti-PD-1 antibody in cancer. The New England journal of medicine 366, 2443 (Jun. 28, 2012).

2B. C. Robert et al., Pembrolizumab versus Ipilimumab in Advanced Melanoma. The New England journal of medicine 372, 2521 (Jun. 25, 2015).

3B. A. Sivan et al., Commensal *Bifidobacterium* promotes antitumor immunity and facilitates anti-PD-L1 efficacy. Science (New York, N.Y.) 350, 1084 (Nov. 27, 2015).

4B. Y. Taur et al., The effects of intestinal tract microbiota diversity on mortality following allogeneic hematopoietic stem cell transplantation. Blood 124, 1174 (Aug. 14, 2014).

5B. R. Daillere et al., *Enterococcus hirae* and *Barnesiella intestinihominis* Facilitate Cyclophosphamide-Induced Therapeutic Immunomodulatory Effects. Immunity 45, 931 (Oct. 18, 2016).

6B. N. Iida et al., Commensal bacteria control cancer response to therapy by modulating the tumor microenvironment. Science (New York, N.Y.) 342, 967 (Nov. 22, 2013).

7B. K. Atarashi et al., Induction of colonic regulatory T cells by indigenous *Clostridium* species. Science (New York, N.Y.) 331, 337 (Jan. 21, 2011).

8B. J. L. Round, S. K. Mazmanian, Inducible Foxp3+ regulatory T-cell development by a commensal bacterium of the intestinal microbiota. Proceedings of the National Academy of Sciences of the United States of America 107, 12204 (Jul. 6, 2010).

9B. N. Geva-Zatorsky et al., Mining the Human Gut Microbiota for Immunomodulatory Organisms. Cell 168, 928 (Feb. 23, 2017).

We claim:

1. A method of treating a subject suffering from cancer with an immune checkpoint inhibitor, the method comprising:
   (a) obtaining a stool sample from the subject;
   (b) characterizing the gut microflora of the subject by having the stool sample tested to determine levels of one or more beneficial bacteria selected from *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum*, and one or both non-beneficial bacteria selected from the species *Ruminococcus obeum* and *Roseburia intestinalis*;
   (c) calculating a ratio of beneficial bacteria to non-beneficial bacteria in the gut of the subject; and
   (d) administering to the subject (i) an immune checkpoint inhibitor intravenously to the subject if the ratio is above 1.5, or (ii) an immune checkpoint inhibitor intravenously and a bacterial formulation comprising one or more beneficial bacteria selected from *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum* orally or rectally to the subject if the ratio is below 1.5.

2. The method of claim 1, wherein at least 50% of the bacteria in the bacterial formulation are *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum*.

3. The method of claim 1, wherein at least 90% of the bacteria in the bacterial formulation are *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum*.

4. The method of claim 1, wherein the bacterial formulation comprises at least $5 \times 10^6$ CFU of bacteria.

5. The method of claim 1, wherein the bacterial formulation is administered to the subject in two or more doses.

6. The method of claim 5, wherein the administration of the two or more doses are separated by at least 1 week.

7. The method of claim 1, further comprising administering to the subject an antibiotic capable of killing the non-beneficial bacteria prior to the administration of the bacterial formulation.

8. The method of claim 7, wherein the antibiotic is administered to the subject at least 1 day before the bacterial formulation is administered to the subject.

9. The method of claim 1, wherein the immune checkpoint inhibitor is a protein or polypeptide that binds to an immune checkpoint protein.

10. The method of claim 9, wherein the immune checkpoint protein is CTLA4, PD-1, PD-L1, PD-L2, A2AR, B7-H3, B7-H4, BTLA, KIR, LAG3, TIM-3 or VISTA.

11. The method of claim 10, wherein the immune checkpoint protein is PD-1 or PD-L1.

12. The method of claim 1, wherein the immune checkpoint inhibitor is an antibody or antigen binding fragment thereof that binds to an immune checkpoint protein.

13. The method of claim 1, wherein the immune checkpoint inhibitor is nivolumab, pembrolizumab, pidilizumab, AMP-224, AMP-514, STI-A1110, TSR-042, RG-7446, BMS-936559, BMS-936558, MK-3475, CT 011, MPDL3280A, MEDI-4736, MSB-0020718C, AUR-012 and STI-A1010.

14. A method of treating a subject with cancer, wherein the subject has a ratio of beneficial bacteria to non-beneficial bacteria of less than 1.5, wherein the one or more beneficial bacteria are selected from *Enterococcus faecium, Collinsella aerofaciens, Bifidobacterium adolescentis, Klebsiella pneumoniae, Veillonella parvula, Parabacteroides merdae, Lactobacillus* sp. and *Bifidobacterium longum*, and wherein the non-beneficial bacteria are one or both of *Ruminococcus obeum* and *Roseburia intestinalis*, comprising intravenously administering to the subject a cancer immunotherapy comprising an immune checkpoint inhibitor and orally or rectally administering to the subject a bacterial formulation comprising one or more of *Enterococcus faecium, Collinsella aerofaciens, Bifidobacterium adolescentis, Klebsiella pneumoniae, Veillonella parvula, Parabacteroides merdae, Lactobacillus* sp. and/or *Bifidobacterium longum* bacteria.

* * * * *